(12) United States Patent
Weymouth-Wilson et al.

(10) Patent No.: US 11,517,577 B2
(45) Date of Patent: Dec. 6, 2022

(54) FLUORINATED BILE ACID DERIVATIVES

(71) Applicants: NZP UK LIMITED, Bristol (GB); THE UNIVERSITY OF SOUTHAMPTON, Southampton (GB)

(72) Inventors: Alexander Charles Weymouth-Wilson, Shinfield (GB); Gemma Packer, Shinfield (GB); Bruno Jan Pol Linclau, Eastleigh (GB); Dannielle Kydd-Sinclair, Reading (GB); Kimberly Ann Watson, Reading (GB)

(73) Assignees: NZP UK LIMITED, Bristol (GB); THE UNIVERSITY OF SOUTHAMPTON, Southampton (GB)

( * ) Notice: Subject to any disclaimer, the term of this patent is extended or adjusted under 35 U.S.C. 154(b) by 0 days.

(21) Appl. No.: 17/262,915

(22) PCT Filed: Jul. 30, 2019

(86) PCT No.: PCT/GB2019/052127
§ 371 (c)(1),
(2) Date: Jan. 25, 2021

(87) PCT Pub. No.: WO2020/025942
PCT Pub. Date: Feb. 6, 2020

(65) Prior Publication Data
US 2021/0299148 A1 Sep. 30, 2021

(30) Foreign Application Priority Data
Jul. 30, 2018 (GB) .................................. 1812382.8

(51) Int. Cl.
| A61K 31/64 | (2006.01) |
| A61P 1/16 | (2006.01) |
| A61K 31/575 | (2006.01) |
| C07J 41/00 | (2006.01) |

(52) U.S. Cl.
CPC ............ *A61K 31/64* (2013.01); *A61K 31/575* (2013.01); *A61P 1/16* (2018.01); *C07J 41/0055* (2013.01); *C07J 41/0061* (2013.01)

(58) Field of Classification Search
CPC ... A61K 31/575; A61K 31/64; C07J 41/0055; C07J 41/0061; A61P 1/16
See application file for complete search history.

(56) References Cited

U.S. PATENT DOCUMENTS
5,175,320 A 12/1992 Pellicciar et al.

FOREIGN PATENT DOCUMENTS
| CN | 106518946 A | 3/2017 |
| EP | 3290429 A1 | 3/2018 |
| WO | 97/44043 A1 | 11/1997 |
| WO | 03/039480 A2 | 5/2003 |
| WO | 2010/014836 A2 | 2/2010 |
| WO | 2014/160441 A1 | 10/2014 |
| WO | 2016/073767 A1 | 5/2016 |
| WO | 2016/145216 A1 | 9/2016 |
| WO | 2016/173493 A1 | 11/2016 |
| WO | 2016/173496 A1 | 11/2016 |

OTHER PUBLICATIONS

Clerici et al. "3α-6α-Dihydroxy-7α-fluoro-5β-cholanoate (UPF-680), physicochemical and physiological properties of a new fluorinated bile acid that prevents 17α-ethynyl-estradiol-induced cholestasis in rats" Toxicology and Applied Pharmacology, 2006, 214, pp. 199-208.
Macchiarulo et al. "Molecular Field Analysis and 3D-Quantitative Structure-Activity Relationship Study (MFA 3D-QSAR) Unveil Novel Features of Bile Acid Recognition at TGR5" J. Chem. Inf. Model., 2008, 48, pp. 1792-1801.
Alemi, F. et al. "The TGR5 receptor mediates bile acid—induced itch and analgesia" The Journal of Clinical Investigation, 2013, 123(4), pp. 1513-1530.
Ananthanarayanan et al. "Ligand-dependent Activation of the Farnesoid X-receptor Directs Arginine Methylation of Histone H3 by CARM1" Journal of Biological Chemistry, 2004, 279(52), pp. 54348-54357.
Bellentani "The epidemiology of non-alcoholic fatty liver disease" Liver International, 2017, 37, pp. 81-84.
Cave et al. "Nuclear receptors and nonalcoholic fatty liver disease" Biochim Biophys Acta, 2016, 1859(9), pp. 1083-1099.

(Continued)

*Primary Examiner* — Barbara P Badio
(74) *Attorney, Agent, or Firm* — Morgan, Lewis & Bockius, LLP

(57) ABSTRACT

The invention relates to compounds of general formula (I):

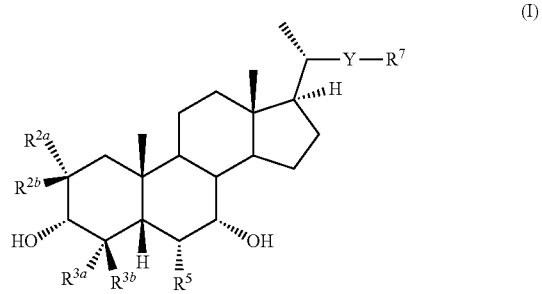

wherein $R^{2a}$, $R^{2b}$, $R^{3a}$, $R^{3b}$, $R^5$, Y and $R^7$ are as defined herein are selective agonists at the FXR receptor and are useful for the treatment or prevention of diseases and conditions including nonalcoholic steatohepatitis (NASH); primary biliary cirrhosis; primary sclerosing cholangitis; biliary atresia; cholestatic liver disease; hepatitis C infection; alcoholic liver disease; fibrosis; and liver damage arising from fibrosis.

17 Claims, 4 Drawing Sheets

(56) References Cited

OTHER PUBLICATIONS

Chang et al. "Dissection of the LXXLL Nuclear Receptor-Coactivator Interaction Motif Using Combinatorial Peptide Libraries: Discovery of Peptide Antagonists of Estrogen Receptors α and β" Molecular and Cellular Biology, 1999, 19(12), pp. 8226-8239.
Chiang "Bile Acid Metabolism and Signalling" Comprehensive Physiology, 2013, 3(3), pp. 1191-1212.
Cipriani et al. "FXR activation reverses insulin resistance and lipid abnormalities and protects against liver steatosis in Zucker (fa/fa) obese rats" Journal of Lipid Research, 2010, 51, pp. 771-784.
Copple et al. "Pharmacology of Bile Acid Receptors: Evolution of Bile Acids from Simple Detergents to Complex Signaling Molecules", Pharmacological Research, 2016, 104, pp. 9-21.
Cushman et al. "Cosalane Analogs with Enhanced Potencies as Inhibitors of HIV-1 Protease and Integrase" J. Med. Chem., 1995, 38, pp. 443-452.
Cusi "Role of Obesity and Lipotoxicity in the Development of Nonalcoholic Steatohepatitis: Pathophysiology and Clinical Implications", Gastroenterology, 2012, 142, pp. 711-725.
Deuschle et al. "FXR Controls the Tumor Suppressor NDRG2 and FXR Agonists Reduce Liver Tumor Growth and Metastasis in an Orthotopic Mouse Xenograft Model" PLoS ONE, 2012, 7(10), e43044.
Dyson et al. "Non-alcoholic fatty liver disease: a practical approach to diagnosis and staging" Frontline Gastroenterology, 2014, 5, pp. 211-218.
Evans et al. "Nuclear Receptors, RXR and the Big Bang" Cell, 2014, 157(1), pp. 255-266.
Goodwin et al. "A Regulatory Cascade of the Nuclear Receptors FXR, SHP-1, and LRH-1 Represses Bile Acid Biosynthesis" Molecular Cell, 2000, 6(3), pp. 517-526.
Haas et al. "Pathophysiology and Mechanisms of Nonalcoholic Fatty Liver Disease" Annual Review of Physiology, 2016, 78, pp. 181-205.
Henao-mejia et al. "Inflammasome-mediated dysbiosis regulates progression of NAFLD and obesity" Nature, 2012, 482(7384), pp. 179-185.
Honorio et al. "Hologram QSAR Studies on Farnesoid X Receptor Activators" Letters in Drug Design & Discovery, 2006, 3(4), pp. 261-271.
Huber et al. "Generation of multiple farnesoid-X-receptor isoforms through the use of alternative promoters" Gene, 2002, 290(1-2), pp. 35-43.
Inagaki et al. "Regulation of antibacterial defense in the small intestine by the nuclear bile acid receptor" PNAS, 2006, 103(10), pp. 3920-3925.
Jiang et al. "Farnesoid X receptor inhibits gankyrin in mouse livers and prevents development of liver cancer" Hepatology, 2013, 57(3), pp. 1098-1106.
Kast et al. "Farnesoid X-activated Receptor Induces Apolipoprotein C-II Transcription: a Molecular Mechanism Linking Plasma Triglyceride Levels to Bile Acids" Molecular endocrinology, 2001, 15(10), pp. 1720-1728.
Kong et al. "Farnesoid X Receptor Deficiency Induces Nonalcoholic Steatohepatitis in Low-Density Lipoprotein Receptor-Knockout Mice Fed a High-Fat Diet" Journal of Pharmacology and Experimental Therapeutics, 2009, 328(1), pp. 116-122.
Landrier et al. "The nuclear receptor for bile acids, FXR, transactivates human organic solute transporter-αand -β genes" Am. J. Physiol. Gastrointest. Liver Physiol., 2006, 290, pp. G476-G485.
Ma et al. "Farnesoid X receptor is essential for normal glucose homeostasis" Journal of Clinical Investigation, 2006, 116(4), p. 1102-1109.
Ma et al. "Synthetic FXR Agonist GW4064 Prevents Diet-Induced Hepatic Steatosis and Insulin Resistance" Pharmaceutical Research, 2013, 30, pp. 1447-1457.

Maloney et al. "Identification of a Chemical Tool for the Orphan Nuclear Receptor FXR" Journal of Medicinal Chemistry, 2000, 43(16), pp. 2971-2974.
Min et al. "Increased hepatic synthesis and dysregulation of cholesterol metabolism is associated with the severity of nonalcoholic fatty liver disease" Cell Metabolism, 2012, 15, pp. 665-674.
Mouzaki et al. "Intestinal Microbiota in Patients With Nonalcoholic Fatty Liver Disease" Hepatology, 2013, 1, pp. 120-127.
Mudaliar et al. "Efficacy and Safety of the Farnesoid X Receptor Agonist Obeticholic Acid in Patients With Type 2 Diabetes and Nonalcoholic Fatty Liver Disease" Gastroenterology, 2013, 145(3), pp. 574-582.
Neuschwander-Tetri "Farnesoid X Receptor Agonists: What They Are and How They Might Be Used in Treating Liver Disease" Current Gastroenterology Reports, 2012, 14(1), pp. 55-62.
Neuschwander-Tetri et al. "Farnesoid X nuclear receptor ligand obeticholic acid for non-cirrhotic, non-alcoholic steatohepatitis (FLINT): a multicentre, randomised, placebo-controlled trial" The Lancet, 2015, 385(9972), pp. 956-965.
Pacana et al. "Recent advances in understanding/management of non-alcoholic steatohepatitis" F1000 Prime Reports, 2015, 7(28), pp. 1-8.
Paulekuhn et al. "Trends in Active Pharmaceutical Ingredient Salt Selection based on Analysis of the Orange Book Database" J. Med. Chem., 2007, 50, pp. 6665-6672.
Pfaffl "A new mathematical model for relative quantification in real-time RT-PCR" Nucleic Acids Research, 2001, 29(9), pp. 16-21.
Roda et al. "Metabolism, pharmacokinetics, and activity of a new 6-fluoro analogue of ursodeoxycholic acid in rats and hamsters" Gastroenterology, 1995, 108(4), pp. 1204-1214.
Sato et al. "Novel Potent and Selective Bile Acid Derivatives as TGR5 Agonists: Biological Screening, Structure-Activity Relationships, and Molecular Modeling Studies" J Med. Chem., 2008, 51(15), pp. 4831-4849.
Sievänen et al., "1H, 13C, 19F NMR, and ESI mass spectral characterization of two geminal difluorosteroids" Magnetic Resonance in Chemistry, 2008, 46(4), pp. 392-397.
Uekawa et al. "Short-step Synthesis of Chenodiol from Stigmasterol" Biosci. Biotechnol. Biochem., 2004, 68, pp. 1332-1337.
Vaquero et al. "Differential activation of the human farnesoid X receptor depends on the pattern of expressed isoforms and the bile acid pool composition" Biochemical Pharmacology, 2013, 86(7), pp. 926-939.
Wang et al. "Farnesoid X receptor antagonizes NF-κB in hepatic inflammatory response" Hepatology, 2008, 48(5), pp. 1632-1643.
Watanabe et al. "Bile acids lower triglyceride levels via a pathway involving FXR, SHP, and SREBP-1c" Journal of Clinical Investigation, 2004, 113(10), pp. 1408-1418.
Watanabe et al. "Lowering bile acid pool size with a synthetic farnesoid X receptor (FXR) agonist induces obesity and diabetes through reduced energy expenditure" Journal of Biological Chemistry, 2011, 286(30), pp. 26913-26920.
Xiao et al. "Synthesis and Biological Evaluation of a Series of Bile Acid Derivatives as FXR Agonists for Treatment of NASH" Med. Chem. Lett., 2017, 8, pp. 1246-1251.
Yang et al. "Effects of nuclear receptor FXR on the regulation of liver lipid metabolism in patients with non-alcoholic fatty liver disease" Hepatology International, 2010, 4(4), pp. 741-748.
Zhang et al. "Peroxisome proliferator-activated regulates triglyceride metabolism by activation of the nuclear receptor FXR" Genes & Development, 2004, 18, pp. 157-169.
Zhang et al. "Activation of the nuclear receptor FXR improves hyperglycemia and hyperlipidemia in diabetic mice" PNAS, 2006, 103(4), pp. 1006-1011.
Zhang et al. "Natural Structural Variants of the Nuclear Receptor Farnesoid X Receptor Affect Transcriptional Activation" Journal of Biological Chemistry, 2003, 278(1), pp. 104-110.
International Search Report and Written Opinion issued in corresponding International Patent Application No. PCT/GB2019/052127 dated Oct. 9, 2019.

FLUORINATED BILE ACID DERIVATIVES

CROSS-REFERENCE TO RELATED APPLICATIONS

This application claims the benefit of International Application No. PCT/GB2019/052127, filed Jul. 30, 2019, which claims the benefit of GB Patent Application No. 1812382.8 filed Jul. 30, 2018, the entire contents of which are hereby incorporated by reference herein in their entireties.

FIELD OF THE INVENTION

The present invention relates to compounds which are derivatives of bile acids and which can be used for the treatment of liver disease. In particular, the invention relates to compounds which are selective agonists of the Farnesoid X receptor and which are therefore of use for the treatment of diseases such as non-alcoholic steatohepatitis (NASH) and primary biliary cholangitis. The invention also relates to pharmaceutical compositions comprising the compounds of the invention.

BACKGROUND OF THE INVENTION

Non-alcoholic fatty liver disease (NAFLD) is one of the most prominent causes of chronic liver disease worldwide and is fast becoming the primary indication for liver transplantation (Bellentani, 2017). NAFLD describes a spectrum of physiological conditions ranging from simple, lipid accumulation in the liver (steatosis), to non-alcoholic steatohepatitis (NASH), which is characterized by both lobular inflammation and hepatocellular injury (Haas, Francque and Staels, 2016). In the west, NAFLD is considered to be a significant public health burden, affecting an estimated 30% of the population in the UK (Dyson, Anstee and McPherson, 2014). The increasing prevalence of NAFLD mirrors the increasing prevalence of obesity and type 2 diabetes, and NAFLD is considered to be a hepatic manifestation of metabolic syndrome (Cave et al., 2016).

Of those with NAFLD, at least 10-20% go on to develop NASH, which is accompanied by the predisposition of patients to both hepatic and extrahepatic complications such as fibrosis, cirrhosis, hepatocellular carcinoma (HCC) and cardiovascular disease. Although poorly understood, the pathological progression of steatosis to NASH, is considered to consist of multiple 'hits', with lipotoxicity, oxidative stress and endoplasmic reticulum stress, sensitizing the liver to additional insults mediated by the innate immune defence systems and leading to cytokine-induced cellular damage (Pacana and Sanyal, 2015). One 'hit' involves hepatic de novo lipogenesis, which is activated by hyperinsulinemia and carbohydrate rich diets. In addition, as a result of insulin resistance, lipolysis in dysfunctional adipocytes is not deactivated, resulting in the leakage of free fatty acids (FFAs) into circulation. These FFAs accumulate in ectopic tissues, such as the liver, where they are stored as triglycerides. However excessive accumulation of FFAs, beyond the threshold of triglyceride storage, ultimately leads to lipotoxicity due to triglyceride-derived toxic metabolites. Moreover, decreased triglyceride clearance and reduced very low density lipoprotein (VLDL) export contributes to the accumulation of fat in the liver. These events are counteracted by the mitochondria and peroxisomes which attempt to oxidise the fatty acids, but it eventually leads to the impairment of these organelles, resulting in the overproduction of reactive oxygen species (ROS) and damage associated molecular pattern molecules (DAMPs). In the second 'hit', lipid peroxidation and activation of inflammatory cytokines by FFAs and ROS, trigger inflammation and apoptosis, and can activate natural immune defence systems via Toll-like receptors, further perpetuating NASH progression by exacerbating insulin resistance and initiating fibrogenesis (Cusi, 2012). Furthermore, recent evidence has implicated the liver-gut axis in the progression of the disease. An altered composition of the gut microbiota and increased gut permeability has been seen in NAFLD patients, and inflammasome-mediated dysbiosis is also thought to drive NASH progression (Henao-mejia et al., 2012; Mouzaki et al., 2013). Collectively, the lipotoxic hepatic events, in addition to the indirect effects of inflammatory mediators from adipose tissues, the intestines and immune system, highlight the complex, multifactorial, cross-system nature of this metabolic disorder and importantly, reflect multiple potential therapeutic targets of NASH (Haas, Francque and Staels, 2016).

Currently, there are no effective medical therapies for NASH treatment or prevention. Most often, weight loss and improved insulin sensitivity through dietary and lifestyle changes are recommended, but as many patients are unable to initiate or maintain these changes, a pharmacological long term solution is needed (Neuschwander-Tetri et al., 2015). Research has focussed on the potential molecular targets for the treatment of NASH, including several nuclear hormone receptors of the NR1 subfamily. These receptors, in particular the Farnesoid X Receptor (FXR), are attractive targets due to their underlying roles in several pathways which contribute to the aetiology of the disease.

As with all nuclear receptors, the Farnesoid X Receptor (FXR) acts as a ligand activated transcription factor which modulates the cellular machinery responsible for epigenetic changes that control transcription. There are two genes which encode FXR; FXRα (NR1H4), which is highly conserved in many species, and FXRβ (NR1H5), which exists as a pseudogene in humans. The FXRα gene encodes four different isoforms which arise due to a combination of different promoter usage and alternative mRNA splicing. Although all four isoforms have a highly conserved ligand binding domain, suggesting that FXR ligands will bind to any isoform in a nonselective manner, there appears to be differential expression, whereby 2 isoforms are predominantly expressed in hepatocytes and cells with an active steroid metabolism, and the others are predominantly expressed in the colon, intestines and other cells involved in enterohepatic circulation (Huber et al., 2002; Vaquero et al., 2013). Moreover, some FXR target genes are more responsive to certain isoforms than others, and the overall pattern of isoform expression is thought to have profound effects in the sensitivity and transcriptional response of specific tissues to FXR ligands (Zhang, Kast-woelbern and Edwards, 2003; Vaquero et al., 2013).

FXR represents a typical nuclear receptor in both its structural organisation and activation. In brief, FXR comprises of an N-terminal DNA binding domain (DBD), made up of two $Zn^{2+}$ fingers responsible for recognising and binding to a consensus hormone response element, connected via a variable hinge region to a C-terminal ligand binding domain (LBD), which exists as a hydrophobic pocket required for the identification and lodging of small molecule ligands (Chiang, 2013). Similarly to other nuclear receptors, FXR binds to DNA as a heterodimer with obliged partner, Retinoid X Receptor (RXR). In the absence of a ligand, FXR is inactive. Generally, the FXR/RXR heterodimer sits pre-bound to the AGGTCA inverted repeat response element of its target genes in complex with corepressor peptides (Neuschwander-Tetri, 2012). Upon activation by ligand binding, the receptor undergoes a conformational change, whereby the corepressor complexes are released, exposing binding sites for a LXXLL coactivation motif in a hydrophobic groove of the ligand binding pocket (Copple and Li, 2016). A 'charge clamp' is formed by hydrogen bonds between the LBD surface and both ends of the coactivator proteins which are recruited to the site. Ultimately, this causes a change in chromatin structure of target genes, allowing access of general transcription factors and RNA polymerase to their promoters, and thus initiating their transcription (Ananthanarayanan et al., 2004).

The classic, endogenous ligands for FXR are bile acids. Bile acids are steroid acids which are found in the bile of mammals and include compounds such as cholic acid, chenodeoxycholic acid, lithocholic acid and deoxycholic acid, all of which are found in humans.

The following shows the general numbering system for steroids and the numbering of the carbon atoms in chenodeoxycholic acid.

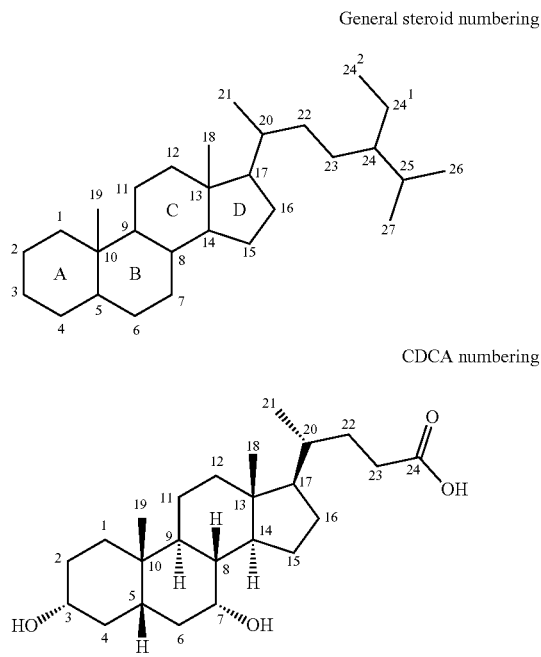

General steroid numbering

CDCA numbering

FXR serves as the master regulator of bile acid metabolism. A primary role of FXR is in facilitating the nutrient and energy transfer along the gut-liver-adipose axis in both the fed and fasting states (Evans and Mangelsdorf, 2014). Following a postprandial stimulus, bile acids enable lipid absorption, as well as activating FXR-mediated signal transduction pathways. This promotes nutrient uptake from the intestines and acts to stimulate energy metabolism in the liver, via the action of FXR target gene fibroblast growth factor 19 (FGF19). In addition to intestinal FGF19, the expression of the FXR transcriptional target, short heterodimer partner (SHP) in the liver, leads to the down regulation of de novo bile acid synthesis, tightly controlling the enterohepatic bile acid pool according to metabolic needs. Studies of NASH patients have shown a reduction in the expression of both FXR and bile acid biosynthetic enzymes, cholesterol 7 alpha hydroxylase (CYP7A1) and sterol 27 hydroxylase (CYP27A1), proportional to the severity of the disease; and NAFLD patients also display an impaired response to hepatic FGF19 (Yang, Shen and Sun, 2010; Min et al., 2013; Cave et al., 2016).

More recently, FXR has emerged as a key player in lipid, glucose and cholesterol homeostasis, modulating genes involved in hepatic lipogenesis, VLDL synthesis, insulin sensitivity, and in part due to interplay with other nuclear receptors, gluconeogenesis and glycogenesis (Kast et al., 2001; Watanabe et al., 2004; Ma et al., 2006; Zhang et al., 2006). Acting via SHP signalling cascades, FXR downregulates sterol regulatory element binding protein (SREBP1) to decrease fatty acid synthesis, while upregulating Peroxisome proliferator-activated receptor alpha (PPARα) to increase the catabolism of fatty acids by mitochondrial β-oxidation, thus reducing hepatic fatty acid accumulation. FXR also acts to increase expression levels of apolipoprotein C2 (APOC2) and VLDL receptor which are responsible for the hydrolysis and clearance of VLDLs. Studies using FXR deficient mice have demonstrated phenotypic similarities to human NASH patients, including significantly increased hepatic triglyceride levels, elevated circulating FFAs and hepatic steatosis (Maloney et al., 2000; Zhang et al., 2004). Furthermore, FXR activation by natural and synthetic agonists has been able to ameliorate plasma triglyceride levels in rodents (Kast et al., 2001). By lowering levels of triglycerides and FFAs, it is thought that FXR activation can also increase insulin sensitivity in both the liver and peripheral tissues, as seen in FXR null mice which displayed mild glucose intolerance and dampened insulin signalling in both the liver and muscle (Ma et al., 2006). Consistent with this finding, insulin sensitivity was improved by semi-synthetic FXR agonist, Obeticholic acid (OCA), in both human subjects with NASH, and in an animal obesity model (Cipriani et al., 2010; Mudaliar et al., 2013). Likewise, FXR, largely via FGF19 signalling, has been proposed to play an important role in glucose homeostasis; lowering plasma glucose concentrations, reducing the expression and activity of three key gluconeogenic enzymes, Phosphoenol-pyruvate carboxykinase (PEPCK), Fructose-1, 6-bis phosphatase (FBP1) and glucose-6-phosphatase (G6Pase), and inhibiting cAMP regulatory-element binding protein (CREB) and downstream PPAR gamma coactivator 1-alpha (PGC1α) to promote glucose storage as glycogen (Zhang et al., 2006). However, conflicting results from animal models suggest that FXR involvement may only be one part of a complex network of receptors and pathways (Watanabe et al., 2011).

Notably, FXR has been implicated in the suppression of hepatic inflammation, where it is involved in a sophisticated pathway which leads to the negative regulation of specific Nuclear Factor kappa B (NF-κB) target genes and proinflammatory cytokines (Wang et al., 2008). Moreover, although the underlying mechanisms are still poorly understood, FXR is thought to have an important role in enteroprotection and in maintaining the intestinal barrier to gut microbiota (Inagaki et al., 2006). FXR knockout mice fed a high-fat diet, displayed intestinal bacterial overgrowth and elevated levels of proinflammatory and pro-fibrogenic mediators, such as Tumour Necrosis Factor alpha (TNFα), Tissue Inhibitor of Metalloproteinases (TIMP) and Transforming Growth Factor beta (TGFβ-1) (Kong et al., 2009). Furthermore, preclinical evidence suggests that engagement by FXR agonists inhibited NFκB expression to improve the inflammatory microenvironment and fibrosis, in primary hepatocytes and in mouse models of NASH (Kong et al., 2009; Ma et al., 2013).

Further supporting its role in NASH, and particularly HCC, FXR has been shown to regulate the expression of tumour suppressor genes, and FXR agonists were shown to reduce the tumour growth and metastasis in a mouse liver xenograft tumour model (Deuschle et al., 2012; Jiang et al., 2013). Accordingly, this evidence, in addition to its central role in the gut-liver-adipose axis, in maintaining intestinal barrier integrity, in inhibiting inflammation, as well in regulating bile acid, glucose and lipid metabolism, supports the idea that FXR dysregulation contributes to the development of NASH, and thus confirms FXR as an ideal target for NASH therapeutics.

A number of FXR agonists are known, including various non-steroidal compounds. More recently, bile acid analogues with FXR agonist activity have been developed. These include obeticholic acid (OCA; INT-747), which is described in WO 02/072598 and EP1568706. Analogues of OCA and medical uses and processes for the preparation of OCA and analogues are described in WO 2005/092925, WO 2005/089316, WO 2006/122977, WO 2007095174, WO 2008/002573, WO 2008/091540, WO 2010/014836, WO 2010/059853, WO 2010/059859, WO 2013/192097, WO 2014/066819, WO 2015/085474, WO 2014/184271, WO 2016/127019, WO 2016/144946, WO 2016/164413, WO 2016/176208, WO 2016/205475, WO 2017/019524, WO 2017/027396, WO 2017/053428, WO 2017/053826, WO 2017/062763, WO 2017/079062, WO 2017/111979 and WO 2017/156024 (all Intercept Pharmaceuticals, Inc).

Further 6-alkyl bile acid analogues with modified side chains are described in WO 2016/073767, WO 2016/086115, WO 2016/086134, WO 2016/086169, WO 2016/086218, WO 2016/130809, WO 2016/161003, WO2017/147137, WO 2017/147159 and WO 2017/147174 (all Enanta Pharmaceuticals, Inc).

Other documents relating to similar compounds include CN105646634, WO 2016/173524, WO 2016/173397, CN105348365, US 2014/0206657.

Our earlier applications WO 2016/079518, WO 2016/079518, WO 2016/079519, WO 2016/079520, WO 2017/199036, WO 2017/199039 and WO 2017/199033 relate to methods of preparing these bile acid analogues and to intermediates in their synthesis.

One of the problems with the bile acid analogues described in the prior art is that, in addition to their activity as FXR agonists, they are also modulators of the G protein-coupled receptor TGR5. This is a member of the rhodopsin-like superfamily of G-protein coupled receptors and has an important role in the bile acid signalling network. For example, one of the adverse effects which has been associated with the use of OCA is pruritus and this is thought to arise from OCA activation of off-target receptors such as TGR5 (Alemi et al., 2013).

Xiao et al., 2017 relates to the synthesis and biological evaluation of OCA and a series of derivatives of OCA as FXR agonists. In the derivatives, the carboxylic acid group was replaced with various alternatives. The authors noted that all tested compounds showed low to moderate TGR5 potency and the best selectivity obtained was a 30 fold selectivity for FXR, which was achieved with a tetrazole derivative. The compound with the highest liver:plasma concentration ratio was Compound 18, which had a $CH_2CH_2C(O)NH$—$S(O)_2CH_3$ side chain.

The present invention relates to novel compounds which maintain FXR agonist activity and which have enhanced selectivity for FXR over TGR5.

Furthermore, bile acid derivatives which are fluorinated at the 2- and/or 4-positions and which have aryl sulfonamide or sulfonylurea side chains have increased agonist activity at the FXR receptor compared with known bile acid derivatives. The inventors speculate that this increased agonist activity is due to the molecules binding into both the canonical and allosteric pockets of FXR ligand binding domain. However, the effectiveness of the compounds of the invention is not affected by the correctness or otherwise of this speculation.

SUMMARY OF THE INVENTION

Therefore, in the present invention there is provided a compound of general formula (I):

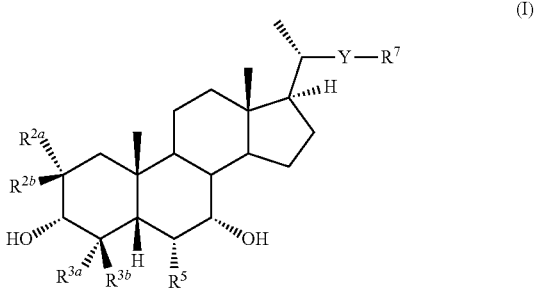

wherein
each of $R^{2a}$, $R^{2b}$, $R^{3a}$ and $R^{3b}$ is independently H or F, provided that at least one of $R^{2b}$ and $R^{3b}$ is F;
$R^5$ is $CR^{6a}R^{6b}R^8$, $OR^8$, $SR^8$ or $NR^{6a}R^8$;
   each $R^{6a}$, $R^{6b}$ and $R^8$ is independently H or methyl
Y is a bond, or a $C_{1-4}$ alkylene or a $C_{2-4}$ alkenylene linker group either of which is optionally substituted with one or more $R^{10}$;
   wherein each $R^{10}$ is independently halo or OH;
$R^7$ is selected from $C(O)NR^{17}S(O)_2R^{15}$, $NR^{17}C(O)NR^{18}S(O)_2R^{15}$, $NR^{17}C(S)NR^{18}S(O)_2R^{15}$ and $NR^{17}C(NR^{20})NR^{18}S(O)_2R^{15}$;
   $R^{15}$ is a 5- to 10-membered aryl or heteroaryl ring optionally substituted with one or more substituents selected from $C_{1-6}$ alkyl, $C_{1-6}$ haloalkyl, halo, $O(C_{1-6}$ alkyl) and $O(C_{1-6}$ haloalkyl);
   each $R^{17}$ and $R^{18}$ is independently H or methyl;
   $R^{20}$ is H, methyl or CN;
or a salt or isotopic variant thereof.

Some fluorinated bile acid derivatives are known. For example, Roda et al, 1995, Honorio et al, 2006, U.S. Pat. No. 5,175,320 and WO 97/44043 all relate to 6-fluoro analogues of ursodeoxycholic acid, while WO 2014/160441 describes a 6,6-difluoro bile acid analogue. Sato et al, 2008 relates to 7-fluoro lithocholic acid derivatives and Sievanen et al, 2008, and Cushman et al, 1995, respectively disclose 3,3-difluoro cholan-24-oic acid and its methyl ester. EP 3290429 discloses bile acid derivatives which are said to be useful for treating FXR-mediated diseases. The compounds disclosed include some 4-fluoro bile acid derivatives. Clerici et al, 2006 and Macchiarulo et al, 2008 both relate to 3α-6α-dihydroxy-7α-fluoro-5β-cholanoate, which is said to be useful for treating liver disease. WO2016/154216 relates to 3- and 7-fluorinated derivatives of UDCA for use in the treatment of neurodegenerative disorders. WO2016/173493 relates bile acid derivatives which have modified side chains and which are modulators of FXR and/or TGR5. US 2018/0148470 relates to 4β-fluorinated bile acid derivatives which are said to be useful for the treatment of FXR-mediated diseases. However, there is no teaching in the prior art of the compounds of general formula (I).

The compounds of general formula (I) are selective FXR agonists and are therefore of use in the treatment of diseases and conditions such as non-alcoholic steatohepatitis (NASH); primary biliary cirrhosis (PBC); primary sclerosing cholangitis; biliary atresia; cholestatic liver disease; hepatitis C infection; alcoholic liver disease; fibrosis; and liver damage arising from fibrosis.

While not wishing to be bound by this theory, the present inventors have speculated that the presence of the fluorine in the ring alters the hydrogen-bonding capacity of the 3α hydroxy group and therefore affects the activity and selectivity of the compound at the FXR and TGR5 receptors. Furthermore, it appears that compounds having a fluoro at the 2- or 4-position of the steroid ring system may have increased metabolic stability.

The inventors have also discovered that the nature of the side chain group (—Y—$R^7$) has a significant impact on the FXR agonist activity as demonstrated in the examples below.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

In the present specification, references to "pharmaceutical use" refer to use for administration to a human or an animal, in particular a human or a mammal, for example a domesticated or livestock mammal, for the treatment or prophylaxis of a disease or medical condition. The term "pharmaceutical composition" refers to a composition which is suitable for pharmaceutical use and "pharmaceutically acceptable" refers to an agent which is suitable for use in a pharmaceutical composition. Other similar terms should be construed accordingly.

In the context of the present specification, the term "plurality" refers to two or more.

All publications, including but not limited to patents and patent applications, cited in this specification are herein incorporated by reference as if each individual publication were specifically and individually indicated to be incorporated by reference herein as though fully set forth.

DETAILED DESCRIPTION OF THE INVENTION

In the present application, the term "$C_{1-6}$" alkyl refers to a straight or branched fully saturated hydrocarbon group having from 1 to 6 carbon atoms. The term encompasses methyl, ethyl, n-propyl, isopropyl, n-butyl, isobutyl, s-butyl and t-butyl. Other alkyl groups, for example $C_{1-4}$ alkyl, $C_{1-3}$ alkyl, or $C_{1-2}$ alkyl are as defined above but contain different numbers of carbon atoms.

The term "alkylene" refers to a straight or branched fully saturated hydrocarbon chain. Suitably alkylene is $C_{1-4}$ alkylene, $C_{1-3}$ alkylene, or $C_{1-2}$ alkylene. Examples of alkylene groups include —$CH_2$—, —$CH_2CH_2$—, —CH($CH_3$)—$CH_2$—, —$CH_2CH(CH_3)$—, —$CH_2CH_2CH_2$— and —$CH_2CH(CH_2CH_3)$—.

The term "alkenylene" refers to a straight or branched hydrocarbon chain containing at least one carbon-carbon double bond. Suitably alkenylene is $C_{2-4}$ alkenylene, or $C_{2-3}$ alkenylene. Examples of alkenylene groups include —CH=CH—, —CH=C($CH_3$)—, —$CH_2$CH=CH—, —CH=CH$CH_2$—, —$CH_2CH_2$CH=CH— and —$CH_2$CH=C($CH_3$)—.

The terms "aryl" and "aromatic" refer to a cyclic group with aromatic character having from 6 to 14 ring carbon atoms (unless otherwise specified, for example 6 to 10 ring carbon atoms) and containing up to three rings. Where an aryl group contains more than one ring, not all rings must be aromatic in character. Examples include phenyl, naphthyl and anthracenyl as well as partially saturated systems such as tetrahydronaphthyl, indanyl and indenyl. A further example of an aryl group is 1,2,3,4-tetrahydronaphthalene.

The terms "heteroaryl" and "heteroaromatic" refer to a cyclic group with aromatic character having from 5 to 14 ring atoms (unless otherwise specified, for example 5 to 10 ring atoms), at least one of which is a heteroatom selected from N, O and S, and containing up to three rings. Where a heteroaryl group contains more than one ring, not all rings must be aromatic in character. Examples of heteroaryl groups include pyridine, pyrimidine, indole, benzofuran, benzimidazole and indolene. Further examples of heteroaryl groups include quinoline and isoquinoline.

The term "halogen" refers to fluorine, chlorine, bromine or iodine and the term "halo" to fluoro, chloro, bromo or iodo groups.

The term "$C_{1-6}$ haloalkyl" refers to a straight or branched alkyl group as defined above having from 1 to 6 carbon atoms and substituted with one or more halo atoms, up to perhalo substitution. Examples include trifluoromethyl, chloroethyl and 1,1-difluoroethyl. Other haloalkyl groups, for example $C_{1-5}$ haloalkyl, $C_{1-4}$ haloalkyl, $C_{1-3}$ haloalkyl or $C_{1-2}$ haloalkyl are as defined above but contain different numbers of carbon atoms.

The term "side chain" refers to the —Y—$R^7$ moiety. In UDCA, —$YR^7$ is —$CH_2CH_2$—C(O)OH and references to a variant side chain refer to —$YR^7$ moieties other than this.

The term "isotopic variant" refers to isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as $^2$H (deuterium), $^3$H, $^{11}$C, $^{13}$C, $^{14}$C, $^{18}$F, $^{123}$I or $^{125}$I (e.g. $^3$H, $^{11}$C, $^{14}$C, $^{18}$F, $^{123}$I or $^{125}$I), which may be naturally occurring or non-naturally occurring isotopes.

Salts of the compounds of general formula (I) are suitably pharmaceutically acceptable salts. However, salts which are not pharmaceutically acceptable may also be used, for example in compounds which are intermediates in the preparation of compounds of general formula (I) or when carrying out reactions to prepare compounds of general formula (I) with alternative side chains.

Appropriate salts of the compounds described herein include basic addition salts such as sodium, potassium, calcium, aluminium, zinc, magnesium and other metal salts as well as choline, diethanolamine, ethanolamine, ethyl diamine, meglumine and other well-known basic addition salts as summarised in Paulekuhn et al., *J. Med. Chem.* 2007, 50, 6665-6672 and/or known to those skilled in the art.

As discussed above, in the compounds of general formula (I), each of $R^{2a}$, $R^{2b}$, $R^{3a}$ and $R^{3b}$ is independently H or F, provided that at least one of $R^{2b}$ and $R^{3b}$ is F.

In some compounds of general formula (I), $R^{3b}$ is F and each of $R^{2a}$, $R^{2b}$ and $R^{3a}$ is H or F. In other compounds of general formula (I), $R^{2b}$ is F and each of $R^{2a}$, $R^{3a}$ and $R^{3b}$ is H or F.

Some suitable compounds of the present invention are monofluorinated.

In some monofluorinated compounds, $R^{3b}$ is F and each of $R^{3a}$, $R^{2a}$ and $R^{2b}$ is H, i.e. the compound of general formula (I) has a 4β-fluoro substituent.

In other monofluorinated compounds, $R^{2b}$ is F and each of $R^{2a}$, $R^{3a}$ and $R^{3b}$ is H, i.e. the compound of general formula (I) has a 2β-fluoro substituent.

Some suitable compounds of general formula (I) are difluorinated. In some suitable difluorinated compounds of general formula (I), $R^{3b}$ is F, $R^{3a}$ is H, one of $R^{2a}$ and $R^{2b}$ is F and the other of $R^{2a}$ and $R^{2b}$ is H, i.e. the compound of general formula (I) has a 2-fluoro substituent and a 4β-fluoro substituent.

In other suitable difluorinated compounds of general formula (I), $R^{3a}$ and $R^{3b}$ are both F and $R^{2a}$ and $R^{2b}$ are both H, such that the compound of general formula (I) is a 4,4-difluoro substituted compound.

The compound of general formula (I) may be a trifluorinated compound, in which three of $R^{2a}$, $R^{2b}$, $R^{3a}$ and $R^{3b}$ are F and the other is H, or a tetrafluorinated compound in which all of $R^{2a}$, $R^{2b}$, $R^{3a}$ and $R^{3b}$ are F.

In the compounds of general formula (I), suitably $R^{6a}$ and $R^{6b}$ are both hydrogen and/or $R^8$ is methyl.

In some suitable compounds, $R^5$ is ethyl, OH or methoxy, particularly ethyl or methoxy and especially ethyl.

In some more suitable compounds, $R^5$ is methoxy.

In particularly suitable compounds, $R^5$ is ethyl.

In some suitable compounds of general formula (I), Y is a bond.

In other suitable compounds of general formula (I), Y is a $C_{1-4}$ alkylene or a $C_{2-4}$ alkenylene linker group either of which is optionally substituted with one or more $R^{10}$ as defined above.

More suitably in these compounds, Y is a $C_{1-4}$, $C_{1-3}$ or $C_{1-2}$ alkylene linker group which is optionally substituted with one or more groups $R^{10}$ as defined above.

In some compounds of general formula (I), Y is unsubstituted.

In other compounds of general formula (I), Y is substituted by one or more substituents $R^{10}$.

In some cases, $R^{10}$ is halo.

In other cases, $R^{10}$ is OH.

Examples of suitable linkers Y include a bond, —CH$_2$—, —CH$_2$CH$_2$—, —CH(OH)—CH$_2$—, —CH═CH— or —CH═C(CH$_3$)—, in particular, a bond, —CH$_2$—, —CH$_2$CH$_2$—, —CH═CH— or —CH═C(CH$_3$)—, especially —CH$_2$—, —CH$_2$CH$_2$—, —CH═CH— or —CH═C(CH$_3$)—.

More suitably, Y is a bond, or a $C_{1-3}$ alkylene linker group which is optionally substituted with one or more OH groups. Still more suitably, Y is a $C_{1-3}$ alkylene linker group which is optionally substituted with one or more OH groups.

In some particularly suitable compounds, Y is an unsubstituted $C_{1-3}$ alkylene linker.

In particularly suitable compounds of general formula (I), Y is —CH$_2$— or —CH$_2$—CH$_2$—, especially —CH$_2$—CH$_2$—.

In the compounds of the present invention, $R^7$ is more suitably C(O)NR$^{17}$S(O)$_2$R$^{15}$ or NR$^{17}$C(O)NR$^{18}$S(O)$_2$R$^{15}$, wherein $R^{15}$, $R^{17}$ and $R^{18}$ are as defined above for general formula (I).

More suitably, each of $R^{17}$ and $R^{18}$ (if present) is H.

In some suitable compounds of general formula (I), $R^{15}$ is selected from phenyl and 5- or 6-membered heteroaryl, for example pyridyl, pyrimidinyl or pyrrolyl, any of which may be unsubstituted or substituted with one or more substituents as defined above, especially 1 to 3 substituents, more usually 1 or 2 substituents and particularly 1 substituent. More suitably, $R^{15}$ is phenyl or a 6-membered heteroaryl group, either of which is unsubstituted or substituted with one or more substituents as defined above, especially 1 to 3 substituents, more usually 1 or 2 substituents and particularly 1 substituent.

Particularly suitable substituents for $R^{15}$ moieties are selected from fluoro, $C_{1-4}$ alkyl, $C_{1-4}$ fluoroalkyl, O($C_{1-4}$ alkyl) and O($C_{1-4}$ fluoroalkyl).

Examples of $R^{15}$ groups in the compounds of general formula (I) include phenyl which is unsubstituted or is substituted with a single substituent selected from fluoro, $C_{1-4}$ alkyl, $C_{1-4}$ fluoroalkyl, O($C_{1-4}$ alkyl) and O($C_{1-4}$ fluoroalkyl), especially fluoro, methyl, ethyl, n-propyl, i-propyl, n-butyl, s-butyl, t-butyl, trifluoromethyl, methoxy and trifluoromethoxy.

When $R^7$ is NR$^{17}$C(O)NR$^{18}$S(O)$_2$R$^{15}$ and $R^{15}$ is phenyl with a single substituent, the substituent may be at any position on the ring but is most suitably a m- or p-substituent, especially a p-substituent. In particular, when $R^7$ is NR$^{17}$C(O)NR$^{18}$S(O)$_2$R$^{15}$ and $R^{15}$ is phenyl substituted with CF$_3$, it is preferred that the CF$_3$ substituent is at the m- or p-position.

Examples of compounds of general formula (I) include:

N,N'-(3α,7α-dihydroxyl-4β-fluoro-6α-ethyl-24-nor-5β-cholan-23-yl)-p-toluene sulfonyl urea (Compound 1);

N,N'-(3α,7α-dihydroxyl-4β-fluoro-6α-ethyl-24-nor-5β-cholan-23-yl)-benzene sulfonyl urea (Compound 2);

N,N'-(3α,7α-dihydroxyl-4β-fluoro-6α-ethyl-24-nor-5β-cholan-23-yl)-4-(tert-butyl) benzene sulfonyl urea (Compound 3);

N,N'-(3α,7α-dihydroxyl-4β-fluoro-6α-ethyl-24-nor-5β-cholan-23-yl)-m-toluene sulfonyl urea (Compound 4);

N,N'-(3α,7α-dihydroxyl-4β-fluoro-6α-ethyl-24-nor-5β-cholan-23-yl)-o-toluene sulfonyl urea (Compound 5);

N,N'-(3α,7α-dihydroxyl-4β-fluoro-6α-ethyl-24-nor-5β-cholan-23-yl)-p-fluorobenzene sulfonyl urea (Compound 6);

N,N'-(3α,7α-dihydroxyl-4β-fluoro-6α-ethyl-24-nor-5β-cholan-23-yl)-m-fluorobenzene sulfonyl urea (Compound 7);

N,N'-(3α,7α-dihydroxyl-4β-fluoro-6α-ethyl-24-nor-5β-cholan-23-yl)-o-fluorobenzene sulfonyl urea (Compound 8);

N,N'-(3α,7α-dihydroxyl-4β-fluoro-6α-ethyl-24-nor-5β-cholan-23-yl)-p-(trifluoromethyl)benzene sulfonyl urea (Compound 9);

N,N'-(3α,7α-dihydroxyl-4β-fluoro-6α-ethyl-24-nor-5β-cholan-23-yl)-m-(trifluoromethyl)benzene sulfonyl urea (Compound 10);

N,N'-(3α,7α-dihydroxyl-4β-fluoro-6α-ethyl-24-nor-5β-cholan-23-yl)-o-(trifluoromethyl)benzene sulfonyl urea (Compound 11);

N,N'-(3α,7α-dihydroxyl-4β-fluoro-6α-ethyl-24-nor-5β-cholan-23-yl)-4-(trifluoromethoxy)benzene sulfonyl urea (Compound 12);

N,N'-(3α,7α-dihydroxyl-4β-fluoro-6α-ethyl-24-nor-5β-cholan-23-yl)-p-methoxybenzene sulfonyl urea (Compound 13);

N-(3α,7α-dihydroxyl-4β-fluoro-6α-ethyl-5β-cholan-24-oyl)-p-trifluoromethoxy benzene sulfonamide (Compound 14);

N-(3α,7α-dihydroxyl-4β-fluoro-6α-ethyl-5β-cholan-24-oyl)-p-fluorobenzene sulfonamide (Compound 15);
N-(3α,7α-dihydroxyl-4β-fluoro-6α-ethyl-5β-cholan-24-oyl)-3-fluorophenyl sulfonamide (Compound 16);
N-(3α,7α-dihydroxyl-4β-fluoro-6α-ethyl-5β-cholan-24-oyl)-2-fluorophenyl sulfonamide (Compound 17);
N-(3α,7α-dihydroxyl-4β-fluoro-6α-ethyl-5β-cholan-24-oyl)-4-trifluoromethylphenyl sulfonamide (Compound 18);
N-(3α,7α-dihydroxyl-4β-fluoro-6α-ethyl-5β-cholan-24-oyl)-3-trifluoromethylphenyl sulfonamide (Compound 19);
N-(3α,7α-dihydroxyl-4β-fluoro-6α-ethyl-5β-cholan-24-oyl)-2-trifluoromethylphenyl sulfonamide (Compound 20);
N,N'-(3α,7α-dihydroxyl-4,4-difluoro-6α-ethyl-24-nor-5β-cholan-23-yl)-benzene sulfonyl urea (Compound 21)
N-(3α,7α-dihydroxyl-4,4-difluoro-6α-ethyl-5β-cholan-24-oyl)-benzene sulfonamide (Compound 22);
and salts and isotopic variants thereof.

A compound of general formula (I) in which $R^7$ is $NHC(O)N(R^{18})S(O)_2R^{15}$ can be prepared by deprotecting a compound of general formula (II):

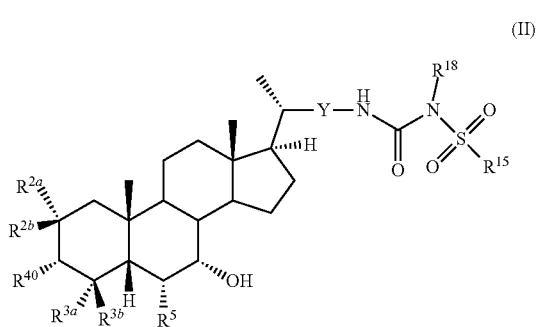

wherein Y, $R^{2a}$, $R^{2b}$, $R^{3a}$, $R^{3b}$ and $R^5$ are as defined for general formula (I) and $R^{40}$ is a protected OH group.

Suitably, the protecting group is one which can be removed by treatment with a base. Examples of protected OH groups of this type include $R^{41}C(O)O$, where $R^{41}$ is $C_{1-6}$ alkyl or benzyl, especially methyl. Silyl ether protecting groups may also be used. Other suitable protecting groups for OH are well known to those of skill in the art (see Wuts, P G M and Greene, T W (2006)).

A compound of general formula (II) may be prepared from a compound of general formula (III):

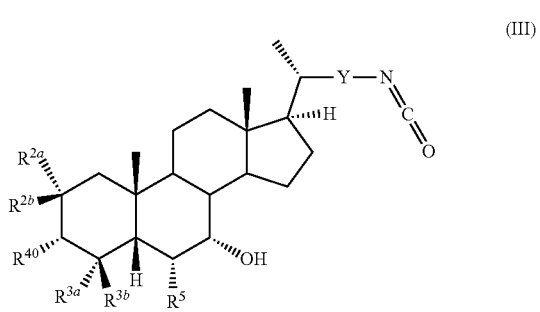

wherein Y, $R^{2a}$, $R^{2b}$, $R^{3a}$, $R^{3b}$ and $R^5$ are as defined for general formula (I) and $R^{40}$ is as defined for general formula (II);

by reaction with a sulfonamide of general formula (IV):

wherein $R^{15}$ and $R^{18}$ are as defined for general formula (I)

in the presence of a catalyst such as 1,8-diazabicyclo[5.4.0]undec-7-ene (DBU) and suitably in an organic solvent such as toluene.

Sulfonamides of general formula (IV) are known and are readily available or may be prepared by known methods.

A compound of general formula (III) may be prepared by heating a compound of general formula (V):

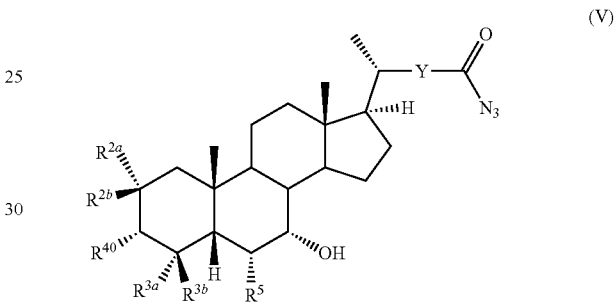

wherein Y, $R^{2a}$, $R^{2b}$, $R^{3a}$, $R^{3b}$ and $R^5$ are as defined for general formula (I) and $R^{40}$ is as defined for general formula (II);

in an inert atmosphere, for example under argon.

Suitably, the compound of general formula (V) is heated to about 100 to 150° C., typically about 125° C.

A compound of general formula (V) may be prepared from a compound of general formula (VI):

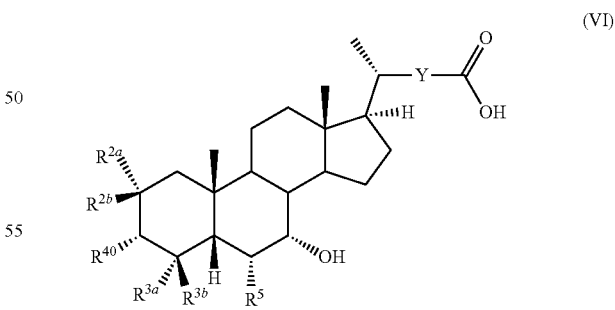

wherein Y, $R^{2a}$, $R^{2b}$, $R^{3a}$, $R^{3b}$ and $R^5$ are as defined for general formula (I) and $R^{40}$ is as defined for general formula (II);

by reaction with diphenylphosphoryl azide under basic conditions, for example in the presence of triethylamine.

The reaction is suitably carried out in an inert atmosphere, for example under argon.

A compound of general formula (VI) may be prepared by protecting a compound of general formula (VII):

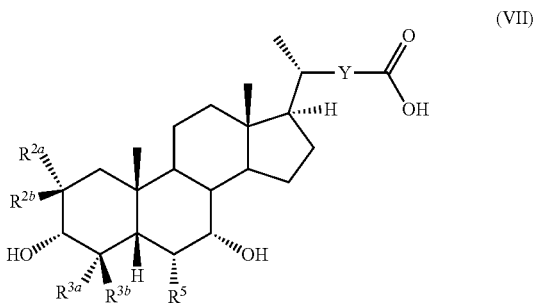

(VII)

wherein Y, $R^{2a}$, $R^{2b}$, $R^{3a}$, $R^{3b}$ and $R^5$ are as defined for general formula (I).

For example, when the protected OH group $R^{40}$ is acetoxy, the compound of general formula (VII) may be reacted with acetic anhydride under mildly basic conditions, for example in the presence of sodium bicarbonate.

The reaction is suitably carried out in an inert atmosphere, for example under argon.

A compound of general formula (VII) may be prepared by hydrolysis of a compound of general formula (VIII):

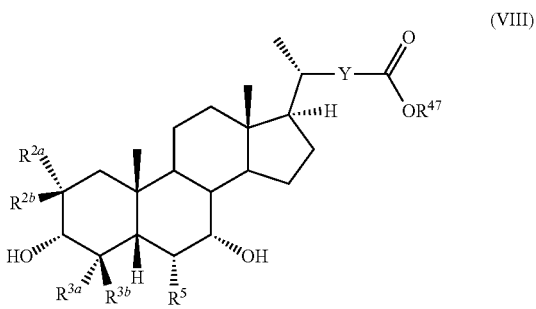

(VIII)

wherein Y, $R^{2a}$, $R^{2b}$, $R^{3a}$, $R^{3b}$ and $R^5$ are as defined for general formula (I) and $R^{47}$ is $C_{1-6}$ alkyl or benzyl.

The hydrolysis may be base catalysed hydrolysis, using, for example an alkali metal hydroxide such as sodium or lithium hydroxide. Suitably, the reaction is conducted in an alcoholic solvent such as methanol.

A compound of general formula (VIII) in which $R^{3b}$ is F may be prepared by reducing an appropriate compound of general formula (XX):

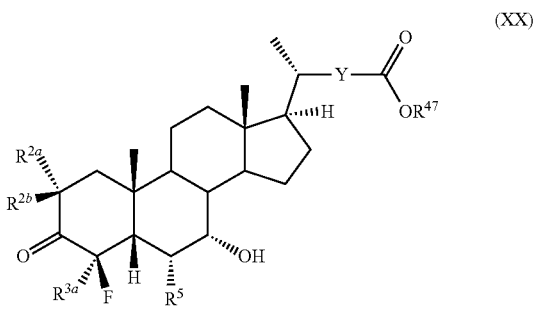

(XX)

wherein Y, $R^{2a}$, $R^{2b}$, $R^{3a}$, $R^{3b}$ and $R^5$ are as defined for general formula (I) and $R^{47}$ is as defined for general formula (VIII).

Suitable reducing agents include hydrides, for example sodium borohydride. The reaction is suitably carried out under an inert atmosphere such as argon and in an organic solvent such as tetrahydrofuran.

Methods for the preparation of a compound of general formula (XX) and a compound of general formula (VIII) in which $R^{2b}$ is F are discussed below.

In an alternative procedure, a compound of general formula (I) in which $R^7$ is $NHC(O)N(R^{18})S(O)_2R^{15}$ may be prepared by deprotecting a compound of general formula (XII):

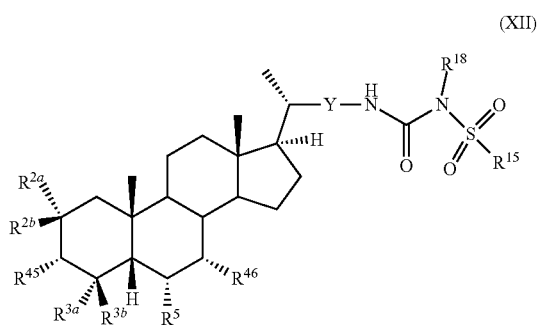

(XII)

wherein Y, $R^{2a}$, $R^{2b}$, $R^{3a}$, $R^{3b}$ and $R^5$ are as defined for general formula (I) and each of $R^{45}$ and $R^{46}$ is independently a protected OH group.

Suitably, each of $R^{45}$ and $R^{46}$ is independently a silyl ether, for example tert-butyldimethylsilyloxy or trimethylsilyloxy. When $R^{45}$ and $R^{46}$ are silyl ethers, they may be the same or different, and deprotection can be achieved by treatment with a reagent such as tetrabutylammonium fluoride (TBAF). Alternative protecting groups may also be used, for example a group $R^{41}C(O)O$ as in general formula (II) above. Other protecting groups are well known in the art (see Wuts, P G M and Greene, T W (2006)).

A compound of general formula (XII) may be prepared from a compound of general formula (XIII):

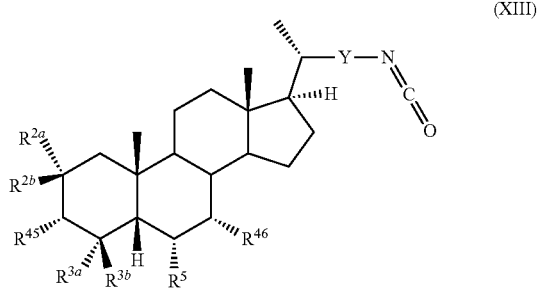

(XIII)

wherein Y, $R^{2a}$, $R^{2b}$, $R^{3a}$, $R^{3b}$ and $R^5$ are as defined for general formula (I) and $R^{45}$ and $R^{46}$ are as defined for general formula (XII);

by reaction with a sulfonamide of general formula (IV) as defined above in the presence of a catalyst such as 1,8-diazabicyclo[5.4.0]undec-7-ene (DBU) and suitably in an organic solvent such as toluene.

A compound of general formula (XIII) may be prepared by heating a compound of general formula (XIV):

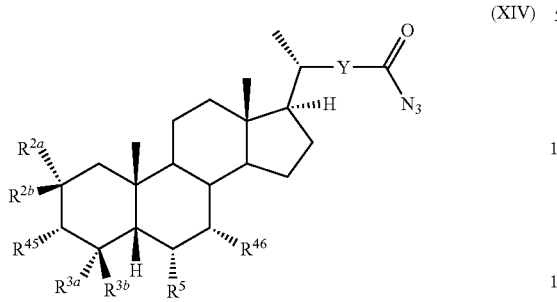

(XIV)

wherein Y, $R^{2a}$, $R^{2b}$, $R^{3a}$, $R^{3b}$ and $R^5$ are as defined for general formula (I) and $R^{45}$ and $R^{46}$ are as defined for general formula (XII);
in an inert atmosphere, for example under argon.

A compound of general formula (XIV) may be prepared from a compound of general formula (XV):

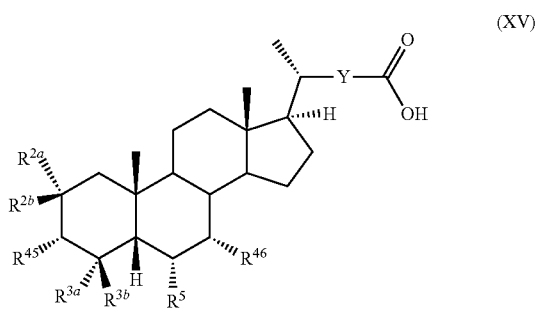

(XV)

wherein Y, $R^{2a}$, $R^{2b}$, $R^{3a}$, $R^{3b}$ and $R^5$ are as defined for general formula (I) and $R^{45}$ and $R^{46}$ are as defined for general formula (XII);
by reaction with diphenylphosphoryl azide under basic conditions, for example in the presence of triethylamine.

A compound of general formula (XV) may be prepared by hydrolysing a compound of general formula (XVI):

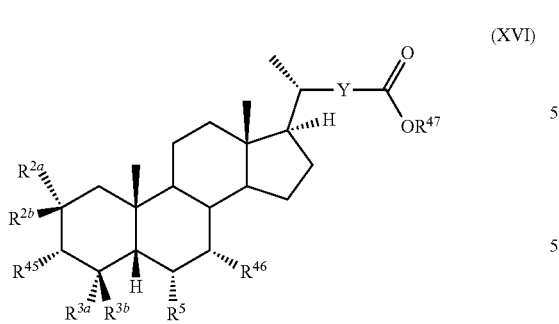

(XVI)

wherein Y, $R^{2a}$, $R^{2b}$, $R^{3a}$, $R^{3b}$ and $R^5$ are as defined for general formula (I), $R^{45}$ and $R^{46}$ are as defined for general formula (XII) and $R^{47}$ is as defined for general formula (VIII).

Suitably, hydrolysis is carried out under basic conditions, for example by treatment with an alkali metal hydroxide, such as sodium or lithium hydroxide. Suitably the reaction is carried out in an alcoholic solvent.

A compound of general formula (XVI) may be prepared by protecting a compound of general formula (XVII):

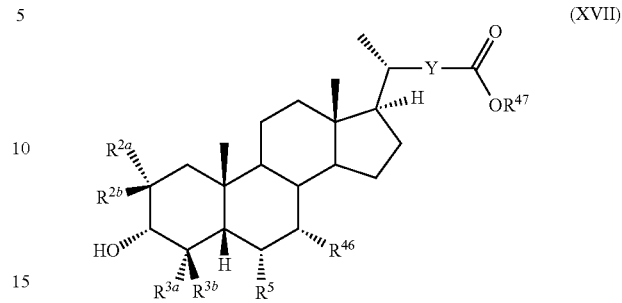

(XVII)

wherein Y, $R^{2a}$, $R^{2b}$, $R^{3a}$, $R^{3b}$ and $R^5$ are as defined for general formula (I), $R^{46}$ is as defined for general formula (XII) and $R^{47}$ is as defined for general formula (VIII).

When the protected OH group $R^{45}$ is a silyl ether, the protection may be achieved by reacting the compound of general formula (XVII) with a compound of general formula (XVIII):

$(R^{50})_3Si—R^{48}$ (XVIII)

wherein $R^{48}$ is a leaving group, typically a halide, for example fluoride, chloride or bromide, or a sulfonyl group such as triflyl, tosyl or mesyl; and wherein each $R^{50}$ is independently, for example, $C_{1-6}$ alkyl or phenyl such that the group $R^{45}$ in the compound of general formula (XVI) will be $(R^{50})_3Si—O$.

The reaction maybe carried out under an inert atmosphere in the presence of a base such as 2,6-lutidine and at a temperature of about −5 to 5° C., typically about 0° C. Suitable solvents include organic solvents such as dichloromethane.

A compound of general formula (XVII) may be prepared by reducing a compound of general formula (XIX):

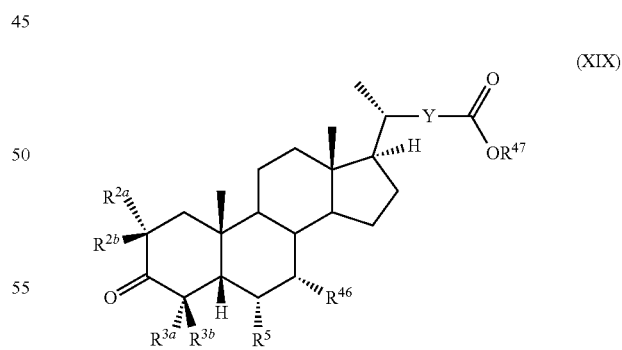

(XIX)

wherein Y, $R^{2a}$, $R^{2b}$, $R^{3a}$, $R^{3b}$ and $R^5$ are as defined for general formula (I), $R^{46}$ is as defined for general formula (XII) and $R^{47}$ is as defined for general formula (VIII).

Suitable reducing agents include hydrides, for example sodium borohydride. The reduction is suitably carried out in an inert atmosphere, for example argon, at a temperature of about 15 to 25° C., typically room temperature, and in a solvent such as tetrahydrofuran.

A compound of general formula (XIX) in which $R^{3b}$ is F may be prepared by protecting a compound of general formula (XX):

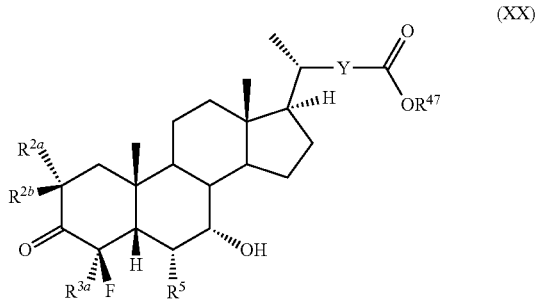

(XX)

wherein Y, $R^{2a}$, $R^{2a}$, $R^{3a}$, $R^{3b}$ and $R^5$ are as defined for general formula (I) and $R^{47}$ is as defined for general formula (VIII).

When the protected OH group $R^{46}$ is a silyl ether, the protection may be achieved by reaction with an appropriate silyl halide or sulfonate (e.g. triflate, mesylate or tosylate) in the presence of a base such as n-butyl lithium. For example, when $R^{46}$ is trimethylsilyloxy, the compound of general formula (XX) may be reacted with trimethylsilyl chloride.

A compound of general formula (I) in which $R^7$ is $C(O)N(R^{17})S(O)_2R^{15}$ may be prepared by deprotecting a compound of general formula (XXII):

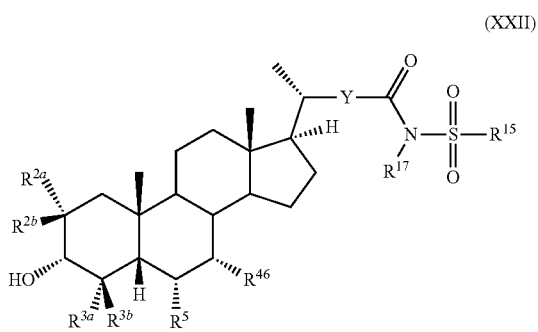

(XXII)

wherein Y, $R^{2a}$, $R^{2b}$, $R^{3a}$, $R^{3b}$, $R^5$, $R^{15}$ and $R^{17}$ are as defined for general formula (I) and $R^{46}$ is as defined for general formula (XII).

When the protected OH group $R^{46}$ is a silyl ether, it may be deprotected by treatment with a base such as TBAF. The reaction is suitably carried out under an inert atmosphere such as argon and in a dry organic solvent such as tetrahydrofuran.

A compound of general formula (XXII) may be prepared from a compound of general formula (XXIII):

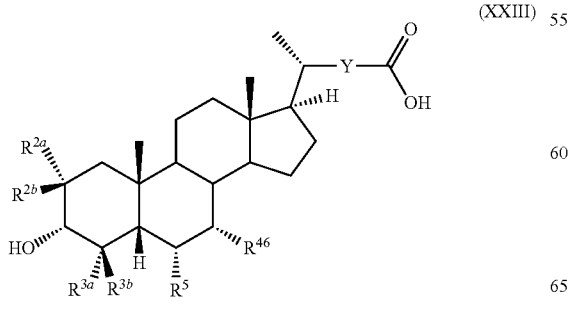

(XXIII)

wherein Y, $R^{2a}$, $R^{2b}$, $R^{3a}$, $R^{3b}$ and $R^5$ are as defined for general formula (I) and $R^{46}$ is as defined for general formula (XII);

by reaction with a sulfonamide of general formula (XXIV):

(XXIV)

wherein $R^{15}$ and $R^{17}$ are as defined for general formula (I);

in the presence of a coupling agent such as 1-ethyl-3(3-dimethylaminopropyl)carbodiimide (EDCI) and a base such as dimethylaminopyridine.

A compound of general formula (XXIII) may be prepared by hydrolysis of a compound of general formula (XVII), suitably under basic conditions, for example by treatment with an alkali metal hydroxide, such as sodium or lithium hydroxide. Suitably the reaction is carried out in an alcoholic solvent.

For compounds of general formula (I) in which $R^{2b}$ is F, $R^{3a}$ and $R^{3b}$ are H and $R^7$ is $C(O)N(R^{17})S(O)_2R^{15}$, a similar route may be used, starting from a compound of general formula (VII) in which $R^{2b}$ is F and $R^{3a}$ and $R^{3b}$ are H.

As discussed above, the compound of general formula (XVII) may be prepared from a compound of general formula (XX) via a compound of general formula (XIX).

The compound of general formula (XX) may be a compound of general formula (XXa), (XXb), (XXc), (XXd) or (XXe):

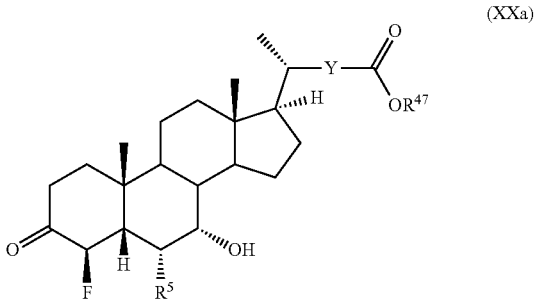

(XXa)

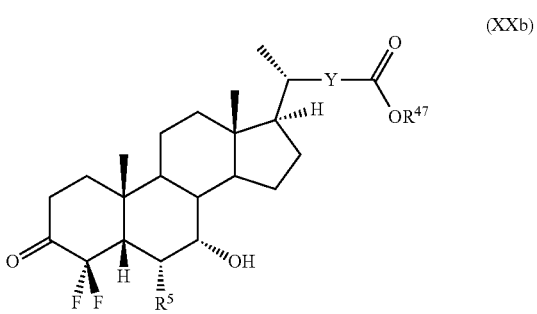

(XXb)

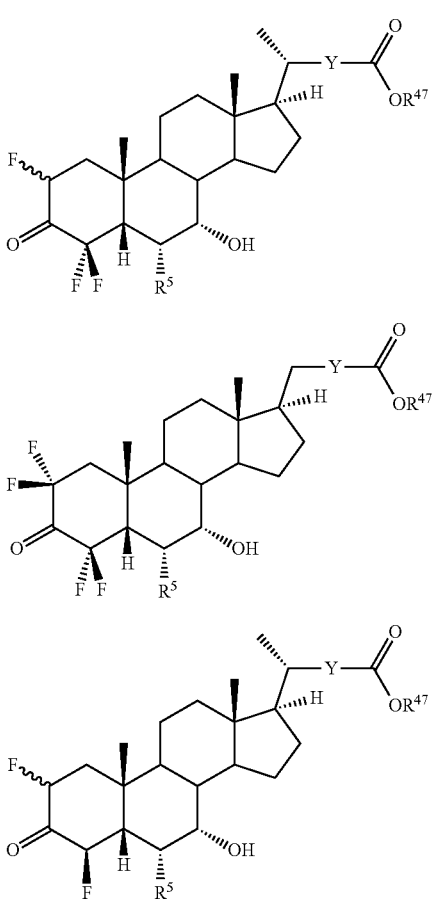

wherein Y and $R^5$ are as defined for general formula (I) and $R^{47}$ is as defined for general formula (VIII).

A compound of general formula (XXa) can be prepared from a compound of general formula (XXX):

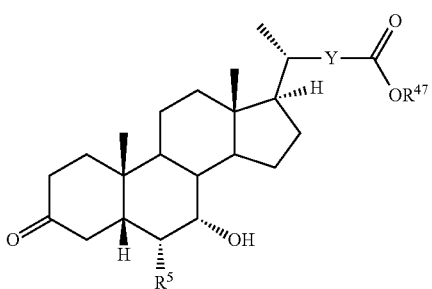

wherein Y and $R^5$ are as defined for general formula (I) and $R^{47}$ is as defined for general formula (VIII);

by a process comprising:

(i) treatment with a strong base, such as n-BuLi or lithium diisopropylamide (LDA), and a trialkylsilyl halide, for example trimethylsilyl chloride, followed by (ii) electrophilic fluorination of the product of step (i), for example with SELECTFLUOR® (1-chloromethyl-4-fluoro-1,4-diazoniabicyclo[2.2.2]octane bis(tetrafluoroborate), which has the structure:

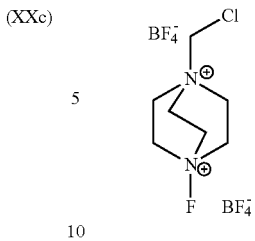

When using SELECTFLUOR®, the reaction is suitably carried out at a temperature of 15 to 25° C., typically at room temperature, in a polar organic solvent such as acetonitrile.

Suitable bases include lithium diisopropylamide (LDA) and n-butyl lithium, which are typically used in combination with trimethylsilyl chloride.

A compound of general formula (XXb) can be prepared from a compound of general formula (XXa) by further fluorination, typically by a similar method to that described above for the compound of general formula (XXa), i.e. by a process comprising:

(i) treatment with a strong base, such as n-BuLi or LDA, and a trialkylsilyl halide, for example trimethylsilyl chloride, followed by (ii) electrophilic fluorination of the product of step (i), for example with SELECTFLUOR®.

A compound of general formula (XXc) can be prepared from a compound of general formula (XXb) by treatment with a strong base, typically LDA used in combination with a trialkylsilyl halide such as trimethylsilyl chloride, followed by fluorination with SELECTFLUOR®.

A compound of general formula (XXd) can be prepared from a compound of general formula (XXc) by further fluorination, typically with SELECTFLUOR® and a weak base such as triethylamine.

A compound of general formula (XXe) can be prepared from a compound of general formula (XXa) by reaction with a compound of formula (XXXI);

wherein each $R^{13}$ is independently selected from $C_{1-6}$ alkyl and phenyl and $R^{51}$ is halo, for example chloro; in the preesence of a strong base such as lithium diisopropylamide followed by fluorination, typically with SELECTFLUOR®.

A compound of general formula (XXX) may be prepared from a compound of general formula (XXXII):

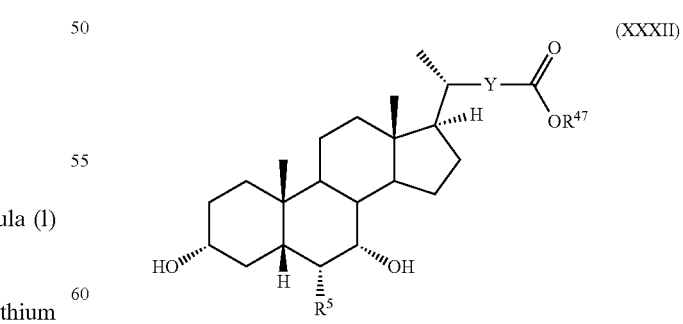

wherein Y and $R^5$ are as defined for general formula (I) and $R^{47}$ is as defined for general formula (VIII);

by oxidation, typically with an agent such as (2,2,6,6-tetramethylpiperidin-1-yl)oxidanyl (TEMPO) or (diacetoxyiodo)benzene (BAIB).

A compound of general formula (XXXII) may be prepared by esterification of a carboxylic acid of general formula (XXXIII):

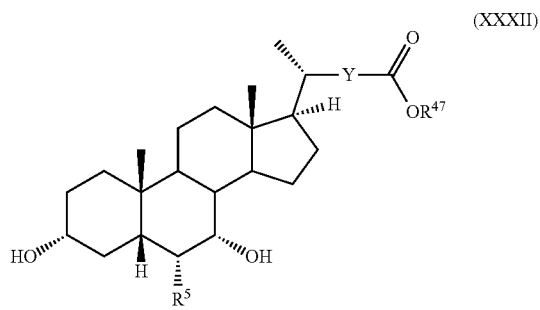

(XXXII)

wherein Y and $R^5$ are as defined for general formula (I);

by reaction with an alcohol of formula $R^{47}$—OH in the presence of an acid, for example p-toluene sulfonic acid or methane sulfonic acid.

Compounds of general formula (XXXIII) are known. The compound of general formula (XXXIII) in which $R^5$ is ethyl and Y is —$CH_2CH_2$— is obeticholic acid (see WO 02/072598).

Our earlier applications WO 2016/079518, WO 2016/079518, WO 2016/079519, WO 2016/079520, WO 2017/199036 and WO 2017/199033 describe methods for preparing compounds of general formula (XXXIII) according to Scheme 1, wherein Y is as defined for general formula (I).

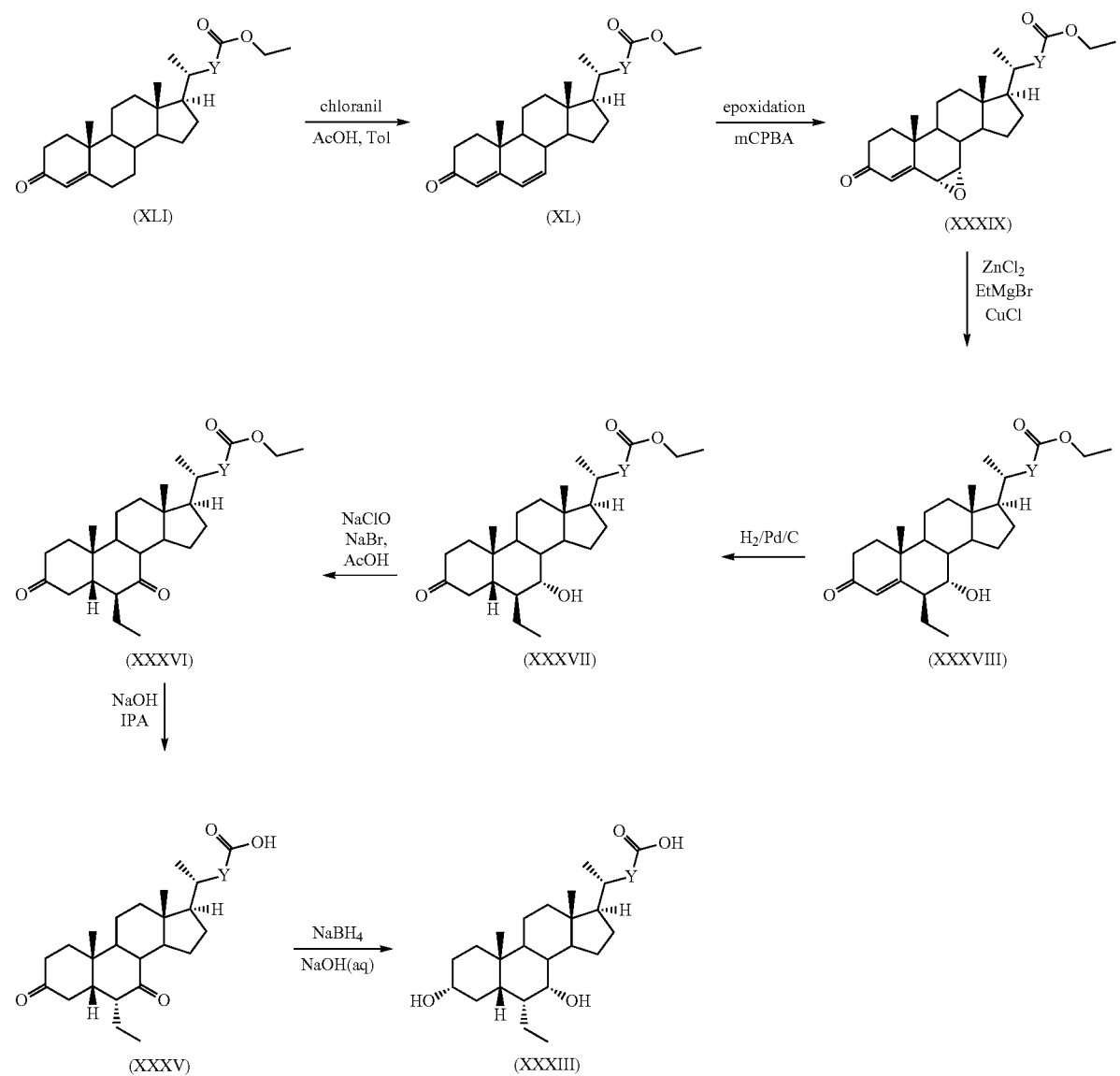

Scheme 1

Some compounds of general formulae (XL) and (XLI) are known and for example Uekawa et al (2004) describe the synthesis of (22E)-3-oxo-4,22-choladien-24-oic acid ethyl ester from stigmasterol:

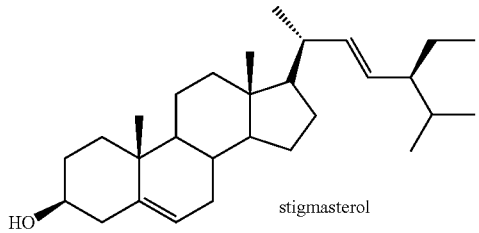

followed by its conversion to (22E)-3-oxo-4,6,22-cholatrien-24-oic acid ethyl ester:

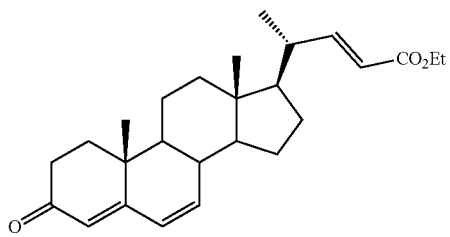 [SMILES: CCOC(=O)/C=C/[C@@H](C)[C@H]1CCC2C3C=CC4=CC(=O)CC[C@]4(C)C3CC[C@@]21C]

Uekawa et al then go on to describe the conversion of this compound to (6α, 7α, 22E)-6,7-epoxy-3-oxo-4,22-choladien-24-oic acid ethyl ester.

Other compounds of general formulae (XL) and (XLI) may be prepared by analogous methods from phytosterols similar to stigmasterol.

Stigmasterol and other phytosterols are plant sterols and are readily available or may be prepared by known routes.

A compound of general formula (VIII) in which $R^{2b}$ is F and $R^{2a}$, $R^{3a}$ and $R^{3b}$ are all H may be prepared by reduction of a compound of general formula (XLV):

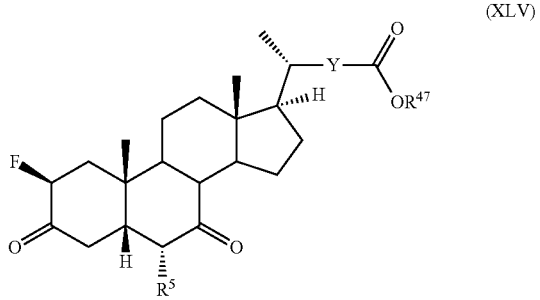

wherein Y and $R^5$ are as defined for general formula (I) and $R^{47}$ is as defined for general formula (VIII).

Suitable reducing agents include hydrides, for example sodium borohydride, and the reaction is carried out under an inert atmosphere such as argon.

The product is obtained as a mixture with the 3β-hydroxy isomer.

A compound of general formula (XLV) may be prepared by esterification of a compound of general formula (XLVI):

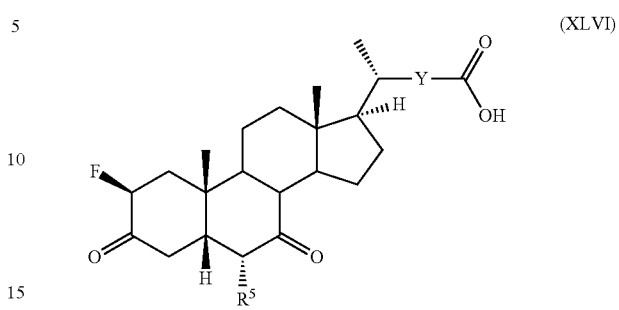

wherein Y and $R^5$ are as defined for general formula (I).

Suitably, esterification is carried out by reaction with a halide, for example an iodide, of the alkyl or benzyl group $R^{47}$ in the presence of a base such as caesium carbonate and in an alcoholic solvent such as methanol.

A compound of general formula (XLVI) may be prepared by epimerisation of a compound of general formula (XLVII):

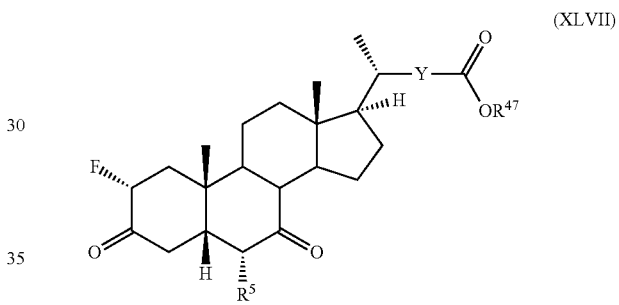

wherein Y and $R^5$ are as defined for general formula (I) and $R^{47}$ is as defined for general formula (VIII).

The epimerisation may be conducted by treating the compound of general formula (XLVII) with a strong base, for example sodium hydroxide and this results in hydrolysis of the $OR^{47}$ moiety to OH. The resulting product is a 60:40 mixture of the compound of general formulae (XLVI) and its 2α isomer. This mixture is then used without further separation in the re-esterification step described above as the ester of general formula (XLV) is significantly easier to separate from its 2α isomer than the carboxylic acid (XLVI).

A compound of general formula (XLVII) may be prepared by oxidation of a compound of general formula (XLVIII):

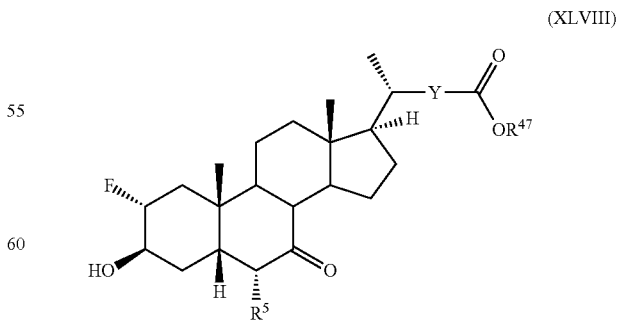

wherein Y and $R^5$ are as defined for general formula (I) and $R^{47}$ is as defined for general formula (VIII). Suitable oxidising agents include Dess-Martin periodinane.

A compound of general formula (XLVIII) may be prepared from a compound of general formula (XLIX):

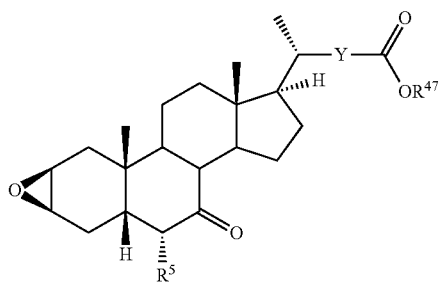

(XLIX)

wherein Y and $R^5$ are as defined for general formula (I) and $R^{47}$ is as defined for general formula (VIII);
by reaction with HF.pyridine (70%) complex under an inert atmosphere such as argon. Suitably, the reaction is conducted in a halogenated solvent such as dichloromethane and at reduced temperature, for example −10 to 10° C., typically about 0° C.

A compound of general formula (XLIX) may be prepared from a compound of general formula (L):

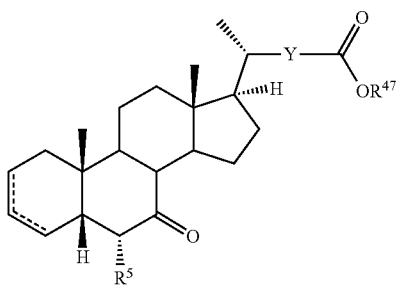

(L)

wherein Y and $R^5$ are as defined for general formula (I) and $R^{47}$ is as defined for general formula (VIII) and the dashed line indicates that one of the bonds is a single bond and the other is a double bond;
by oxidation, for example using m-perchlorobenzoic acid in a halogenated organic solvent such as dichloromethane. Suitably, the reaction is conducted at a temperature of 15 to 25° C., typically at room temperature.

A compound of general formula (L) may be prepared from a compound of general formula (LI):

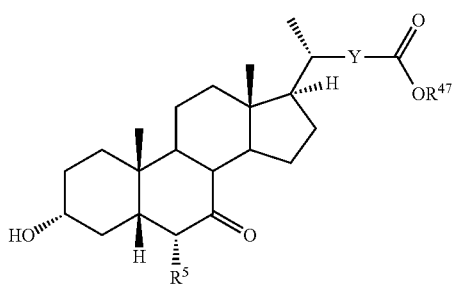

(LI)

wherein Y and $R^5$ are as defined for general formula (I) and $R^{47}$ is as defined for general formula (VIII);

by dehydration, using a suitable dehydrating agent such as triflic anhydride in the presence of a base such as dimethylaminopyridine. Suitably, the reaction is conducted in a halogenated organic solvent such as dichloromethane at a temperature of 15 to 25° C., typically at room temperature.

A compound of general formula (LI) may be prepared by reaction of a compound of general formula (LII):

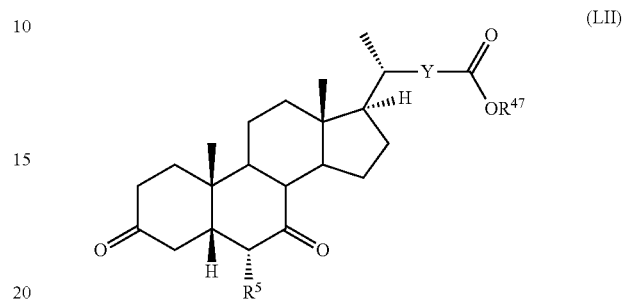

(LII)

wherein Y and $R^5$ are as defined for general formula (I) and $R^{47}$ is as defined for general formula (VIII); with a reducing agent such as L-SELECTRIDE®(lithium tri-sec-butylborohydride), followed by treatment with hydrogen peroxide.

Suitably, the reaction with L-SELECTRIDE® is conducted under an inert atmosphere such as argon and at reduced temperature, typically −78° C. The reaction with hydrogen peroxide is suitably carried out at a temperature of about 0° C.

A compound of general formula (LII) may be prepared by esterification a compound of general formula (LIII):

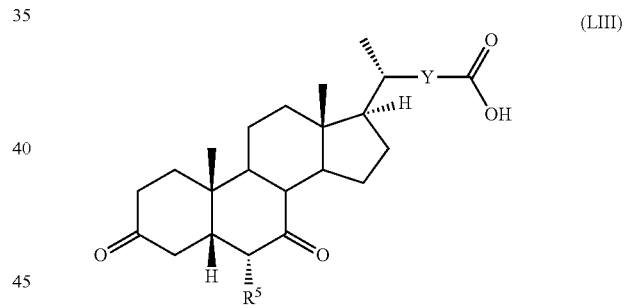

(LIII)

wherein Y and $R^5$ are as defined for general formula (I).

Suitably, esterification takes place by reaction with an alcohol $R^{47}$—OH in the presence of an acid comprising a leaving group, for example p-toluenesulfonic acid. The reaction may be conducted at a temperature of about 20 to 40° C., for example about 30° C.

Compounds of general formula (LIII) are known and may be prepared by methods known to those of skill in the art, for example as taught in WO 2016/079518, WO 2016/079518, WO 2016/079519, WO 2016/079520, WO 2017/199036 and WO 2017/199033.

The compounds of general formula (I) are FXR agonists and are therefore useful in the treatment or prophylaxis of FXR mediated diseases and conditions.

Therefore, in a further aspect of the invention there is provided a compound of general formula (I) for use in medicine.

The compound may be used in human or veterinary medicine, suitably for the treatment of a mammal, particularly a human.

Compounds of general formula (I) are of particular use in the treatment or prevention of metabolic syndrome including nonalcoholic steatohepatitis (NASH); primary biliary cirrhosis; primary sclerosing cholangitis; biliary atresia; cholestatic liver disease; hepatitis C infection; alcoholic liver disease; fibrosis; and liver damage arising from fibrosis.

The invention also provides the use of a compound of general formula (I) in the preparation of an agent for the treatment or prevention of nonalcoholic steatohepatitis (NASH); primary biliary cirrhosis; primary sclerosing cholangitis; biliary atresia; cholestatic liver disease; hepatitis C infection; alcoholic liver disease; fibrosis; or liver damage arising from fibrosis.

There is also provided a method for the treatment or prevention of nonalcoholic steatohepatitis (NASH); primary biliary cirrhosis; primary sclerosing cholangitis; biliary atresia; cholestatic liver disease; hepatitis C infection; alcoholic liver disease; fibrosis; or liver damage arising from fibrosis, the method comprising administering to a patient in need of such treatment an effective amount of a compound of general formula (I).

Fibrosis includes fibrosis of the liver, kidneys and intestines.

Liver fibrosis may be associated with NASH, alcoholic liver disease or non-alcoholic fatty liver disease. Alternatively, the liver fibrosis may be associated with an infection such as hepatitis, especially hepatitis B or hepatitis C or a parasitic liver disease. Other causes of liver fibrosis include damage induced by congenital disorders such as Wilson's disease, Gaucher's disease, glycogen storage disorders haemochromatosis, Zellweger syndrome and congenital hepatic fibrosis. Liver fibrosis can also be induced by drugs such as chlorpromazine, tolbutamide, methotrexate, isoniazid and methyldopa.

Fibrosis of the kidneys may be associated with a disease such as diabetic nephropathy, hypertensive nephrosclerosis, glomerulonephritis, interstitial nephritis, glomerulopathy associated with transplant and polycystic kidney disease.

Intestinal fibrosis may be associated with a bowel disorder.

Bowel disorders include irritable bowel syndrome, Crohn's disease and ulcerative colitis.

Compounds of general formula (I) are suitably provided in a pharmaceutical composition and in a further aspect of the invention there is provided a pharmaceutical composition comprising a compound of general formula (I) and a pharmaceutically acceptable excipient or carrier.

The particular excipients or carriers used will depend upon the selected route of administration and must be must be acceptable in the sense of being compatible with the other ingredients of the formulation and not deleterious to the recipient.

The compositions of the invention may also include one or more additional active ingredients suitable for treating one or more of the diseases and conditions listed above.

The formulations include those suitable for oral, rectal, nasal, bronchial (inhaled), topical (including eye drops, buccal and sublingual), vaginal or parenteral (including subcutaneous, intramuscular, intravenous and intradermal) administration and may be prepared by any methods well known in the art of pharmacy.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) into conjunction or association with a pharmaceutically or veterinarily acceptable excipient or carrier.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) or (II) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Parenteral formulations will generally be sterile.

FIGURES

In the figures, * represents p values<0.05,  represents p values<0.01 and * represents p values<0.001.

EXAMPLES

Figure 1:
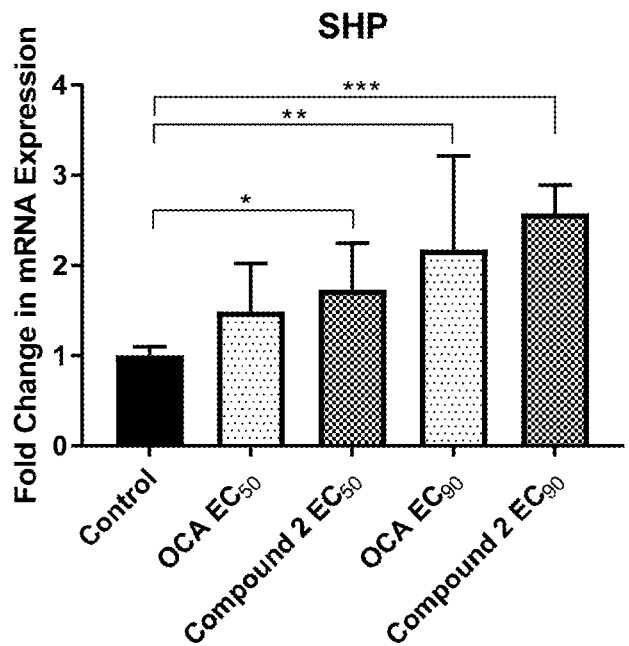
FIG. 1 shows the change in SHP expression after 24 hours incubation of the human hepatoma cell line Huh7 with control, OCA (at $EC_{50}$ and $EC_{90}$) and Compound 2 (at $EC_{50}$ and $EC_{90}$).

In the Examples, the following abbreviations are used.

$Ac_2O$ Acetic anhydride
DBU 1,8-Diazabicyclo[5.4.0]undec-7-ene
DMAP Dimethylaminopyridine
EDCI 1-Ethyl-3-(3-dimethylaminopropyl)carbodiimide
Equiv Equivalents
$Et_3N$ Triethylamine
EtOAc Ethyl acetate
IPA Isopropyl alcohol
h Hours
HDCA Hyodeoxycholic acid
HPLC High performance liquid chromatography
LDA Lithium diisopropylamide
MeOH Methanol
n-BuLi n-Butyl lithium
OCA Obeticholic acid
PE Petroleum ether
PTFE Polytetrafluoroethylene
pTSA p-Toluenesulfonic acid
RT Room temperature
sat Saturated
TBAF Tetrabutylammonium fluoride
TBDMS-OTf Tert-butyldimethylsilyltrifluoromethane sulfonate
TEMPO (2,2,6,6-Tetramethylpiperidin-1-yl)oxidanyl
THF Tetrahydrofuran
TMS-Cl Trimethylsilylchloride
TMS-OTf Trimethylsilyl trifluorotrifluoromethane sulfonate
TLC Thin layer chromatography Example 1—Synthesis of 3α-hydroxyl-4β-fluoro-6α-ethyl-7α-hydroxyl-5β-cholanic Acid Analogues with Sulfonylurea-Substituted Side Chains A. Methyl 6α-ethyl-3α,7α-dihydroxyl-5β-cholan-24-oate

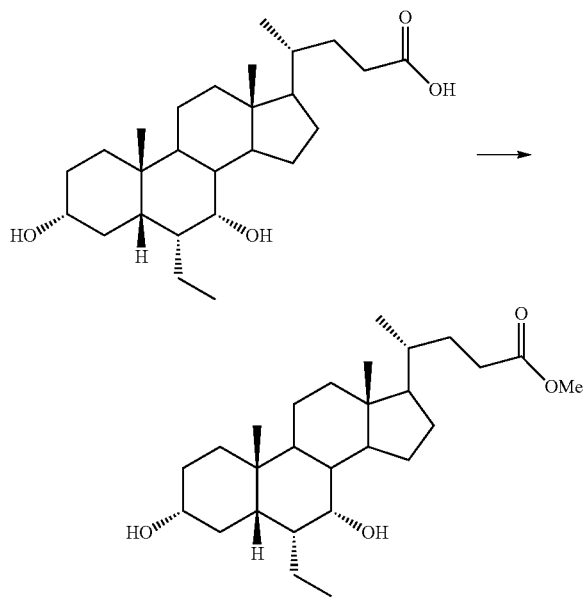

To a solution of OCA (23.5 g, 55.87 mmol) in MeOH (540 mL) at RT was added para-toluenesulfonic acid (1.02 mg, 5.59 mmol, ~0.1 equiv.) and sonicated at 30° C. for 3 h. Upon completion the reaction mixture was concentrated in vacuo. The residue was dissolved in chloroform (500 mL) and washed with saturated $NaHCO_3$ (500 mL), $H_2O$ (500 mL) and brine (500 mL), dried over $MgSO_4$, filtered and concentrated in vacuo to yield the title compound as a white solid in quantitative yield. The resulting solid was used without further purification.

$^1$H NMR (400 MHz, $CDCl_3$): δ 3.70 (1H, s), 3.67 (3H, s,), 3.44-3.37 (1H, m), 2.40-2.32 (1H, m), 2.26-2.18 (1H, m), 1.96 (1H, dt, J=12.0, 2.6 Hz), 1.92-1.76 (6H, m), 1.69-1.59 (3H, m), 1.58-1.12 (14H, m), 1.00 (1H, td, 14.2, 3.3 Hz), 0.93 (3H, d, J=6.3 Hz), 0.90 (3H, s), 0.90 (3H, t, J=7.4 Hz), 0.66 (3H, s) ppm.

LRMS ($ESI^+$) m/z: 452.4 $[M+NH_4]^+$, 100%.

B. Methyl 6α-ethyl-7α-hydroxyl-3-oxo-5β-cholan-24-oate

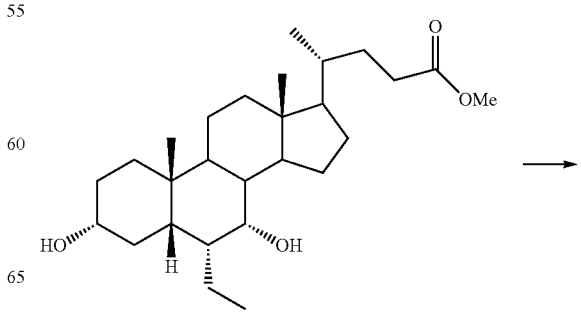

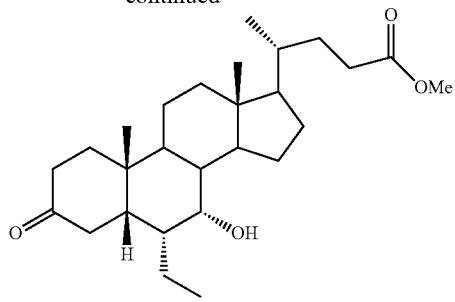

To a stirred solution of methyl 6α-ethyl-3α,7α-dihydroxyl-5β-cholan-24-oate from Step A (9.53 g, 21.9 mmol) in H₂O (22 mL) and tert-butanol (88 mL) at RT was added KBr (5.22 g, 43.9 mmol, ~2.0 equiv.), KHCO₃ (22.0 g, 219 mmol, ~10 equiv.) and TEMPO (4.45 g, 28.5 mmol, ~1.3 equiv.). The reaction mixture was cooled to 0° C. and received NaClO (28 mL, 32.9 mmol, ~1.5 equiv.) dropwise at a rate of 4 mL per hour over 7 hours. Upon completion the reaction was quenched by the slow addition of 1:1 saturated Na₂S₂O₃ (250 mL) and diluted with EtOAc (200 mL). The organic phase was removed followed by back extraction of the aqueous phase with EtOAc (3×150 mL). Organic phases combined, dried over MgSO₄, filtered and concentrated in vacuo to afford 14.2 g of crude material as an orange oil. The resultant oil was purified via column chromatography (gradient elution of acetone in PE 40-60, 0-20%) to yield the title compound as a white solid (8.48 g, 89%).

¹H NMR (400 MHz, CDCl₃): δ 3.78 (1H, d, J=2.2 Hz), 3.67 (3H, s), 3.07 (1H, dd, J=15.2, 13.5 Hz), 2.46-2.33 (2H, m), 2.29-1.91 (7H, m), 1.84-1.77 (1H, m). 1.74-1.15 (18H, m), 1.00 (3H, s), 0.94 (3H, d, J=6.5 Hz), 0.91 (3H, t, J=7.4 Hz), 0.70 (3H, s) ppm.

LRMS (ESI⁺) m/z: 450.3 [M+NH₄]⁺, 100%.

C. Methyl 6α-ethyl-4β-fluoro-7α-hydroxyl-3-oxo-5β-cholan-24-oate

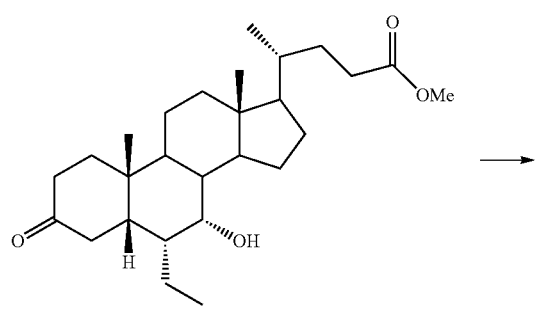

To a stirred, pre-cooled solution of diisopropylamine (0.78 mL, 5.54 mmol, ~12 equiv.) in dry THF (6.9 mL) at −78° C. was added n-BuLi in hexanes (1.44 mL, 2.31 mmol, ~5.0 equiv.) dropwise over 0.25 h under argon. After addition, trimethylsilylchloride (0.29 mL, 2.31 mmol, ~5.0 equiv.) was added and stirred for 1 h. A solution of methyl 6α-ethyl-7α-hydroxyl-3-oxo-5β-cholan-24-oate from Step B (200 mg, 0.46 mmol) in dry THF (3 mL) and triethylamine (1.16 mL, 8.32 mmol, ~18 equiv.) were then added. After addition the reaction was gradually allowed to warm to −20° C. and stirred for 2 h. Upon completion the reaction was quenched via the dropwise addition of saturated NaHCO₃ (5 mL) and warmed to RT for 2 h. The organic phase was removed and the aqueous phase back extracted with EtOAc (3×10 mL). Organic phases were combined, washed with brine (30 mL), dried over MgSO₄, filtered and concentrated in vacuo to afford 271 mg of crude material as a yellow residue.

To a stirred solution of the resultant crude material in MeCN (13 Ml) was added SELECTFLUOR® and the mixture was stirred for 16 h. Upon completion the reaction mixture was concentrated in vacuo. The residue was dissolved in EtOAC (20 mL) and acidified with 2M HCl (30 mL). The organic phase was removed and the aqueous phase back extracted with EtOAc (3×15 mL). Organic phases were combined, washed with brine (100 mL), dried over MgSO₄, filtered and concentrated in vacuo to afford 196 mg of crude material as a green solid. Purification by HPLC using hexane/acetone (90/10) as the eluent yielded an inseparable mix of the title compound and methyl-2β-fluoro-3-oxo-6α-ethyl-7α-hydroxyl-5β-cholan-24-oate as a colourless oil (79 mg, 0.18 mmol, 37% title compound, considering 1% methyl-2β-fluoro-3-oxo-6α-ethyl-7α-hydroxyl-5β-cholan-24-oate contamination by ¹H NMR).

¹H NMR (400 MHz, CDCl₃): δ 5.94 (1H, dd, J=46.5, 10.9 Hz), 3.88 (1H, s), 3.65 (3H, s), 2.49 (1H, td, J=14.6, 5.0 Hz), 2.38-2.09 (4H, m), 2.01-1.30 (18H, m), 1.25-1.14 (3H, m), 1.04 (3H, s), 0.93-0.89 (6H, m), 0.68 (3H, s) ppm.

¹⁹F NMR (¹H non-decoupled, 376 MHz, CDCl₃): −194.3 (1F, dd, J=46.8, 13.9 Hz) ppm.

LRMS (ESI⁺) m/z: 468.4 [M+NH₄]⁺, 100%.

D. Methyl 6α-ethyl-4β-fluoro-(3α,7α)-dihydroxyl-5β-cholan-24-oate

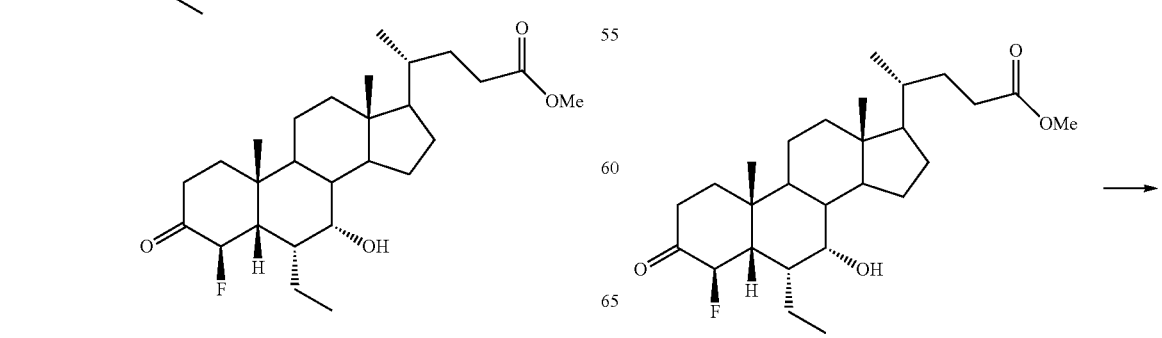

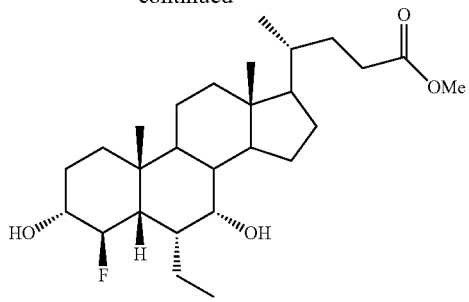

To a stirred solution of methyl 6α-ethyl-4β-fluoro-7α-hydroxyl-3-oxo-5β-cholan-24-oate from Step C (75 mg, 0.17 mmol) in dry THF (6.7 mL) at RT was added NaBH₄ (19 mg, 0.50 mmol, ~3.0 equiv.) and stirred for 16 h under argon. Upon completion the reaction was quenched via the dropwise addition of H₂O (8 mL) and diluted with EtOAc (10 mL). The organic phase was removed and the aqueous phase back extracted with EtOAc (3×50 mL). Organic phases were combined, washed with H₂O (100 mL), dried over MgSO₄, filtered and concentrated in vacuo to afford 77 mg of crude material as a white residue. Purification by HPLC using hexane/acetone (90/10) as the eluent yielded the title compound as a colourless oil (55 mg, 0.12 mmol, 74%).

$^1$H NMR (400 MHz, CDCl₃): δ 5.31 (1H, ddd, J=50.0, 10.4, 8.9 Hz), 3.82 (1H, s), 3.67 (3H, s), 3.57-3.50 (1H, m), 2.36 (1H, ddd, J=15.4, 10.1, 5.7 Hz), 2.27-2.18 (1H, m), 1.96-1.92 (2H, m), 1.83-1.07 (23H, m), 0.97 (3H, s), 0.94-0.92 (6H, m), 0.66 (3H, s) ppm.

$^{19}$F NMR ($^1$H non-decoupled, 376 MHz, CDCl₃): δ−189.0 (1F, d, J=50.3 Hz) ppm.

LRMS (ESI⁺) m/z: 470.4 [M+NH₄]⁺, 100%.

E. 3α, 7α-Dihydroxyl-4β-fluoro-6α-ethyl-5β-cholanic Acid

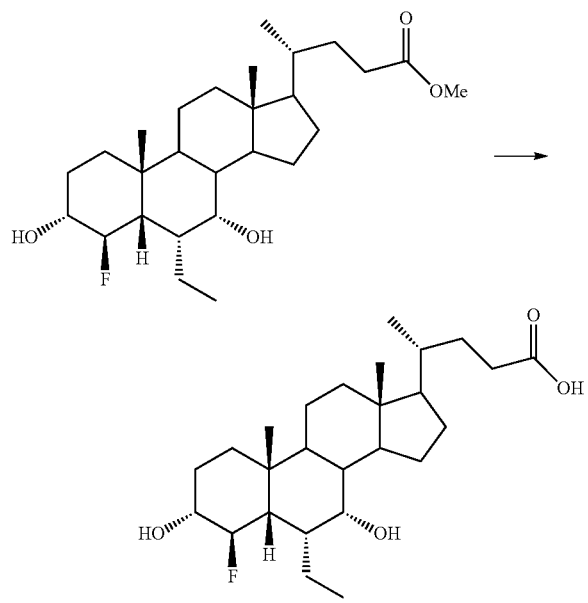

To a stirred solution of methyl 6α-ethyl-4β-fluoro-(3α, 7α)-dihydroxyl-5β-cholan-24-oate (58 mg, 0.13 mmol) in MeOH (5 mL) at RT was added NaOH (250 mg, 5% solution) and stirred for 18 h. Upon completion the reaction mixture was concentrated in vacuo and the residue acidified to pH 2 with 1M HCl and diluted with EtOAc (20 mL). The organic phase was removed and the aqueous phase back extracted with EtOAc (3×50 mL). Organic phases were combined, washed with brine (100 mL), dried over MgSO₄, filtered and concentrated in vacuo to afford 76 mg of crude material as a yellow oil. Purification by HPLC using hexane/acetone (70/30) as the eluent yielded the title compound as a colourless oil (41 mg, 0.09 mmol, 72%).

$^1$H NMR (400 MHz, CDCl₃): δ 5.31 (1H, dt, J=49.9, 9.5 Hz), 3.83 (1H, s), 3.60-3.50 (1H, m), 2.36 (1H, ddd, J=15.5, 10.4, 5.3 Hz), 2.26 (1H, ddd, J=15.8, 9.5, 6.6 Hz), 1.97-1.91 (2H, m), 1.85-1.08 (21H, m), 0.97 (3H, s), 0.95-0.91 (6H, m), 0.67 (3H, s) ppm.

$^{19}$F NMR ($^1$H non-decoupled, 376 MHz, CDCl₃): δ−188.7 (1F, d, J=48.6 Hz) ppm.

LRMS (ESI⁺) m/z: 456.2, [M+NH₄]⁺, 100%.

Synthesis of Compounds with Sulfonylurea-Substituted Side Chains

The methods below are illustrated for 4β-fluoro derivatives but could also be used for 2β-fluorinated, 4,4-difluorinated or 2,4-difluoroinated compounds.

F. 3α-Acetoxy-4β-fluoro-6α-ethyl-7α-hydroxyl-5β-cholanic Acid

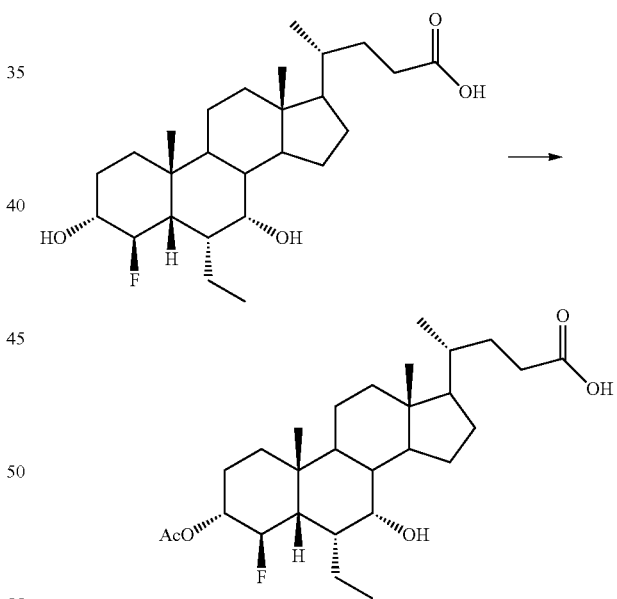

To a stirred solution of 3α, 7α-dihydroxyl-4β-fluoro-6α-ethyl-5β-cholanic acid from Step E (2.08 g, 4.74 mmol) in dry THF (160 mL) at RT under argon was added NaHCO₃ (2.04 g, 23.7 mmol, ~5.0 equiv.) and Ac₂O (2.29 mL, 23.7 mmol, ~5.0 equiv.) dropwise over 5 mins. After addition, the reaction mixture was heated at 70° C. for 16 h. Upon completion, the reaction mixture was cooled to RT and quenched by the dropwise addition of H₂O (100 mL), acidified with 1M HCl (20 mL) and diluted with EtOAc (100 mL). The organic phase was removed and the aqueous phase back extracted with EtOAc (3×150 mL). Organic phases were combined, washed with brine (400 mL), dried over MgSO$_4$, filtered and concentrated in vacuo to yield a yellow oil. The resultant oil was purified via column chromatography (gradient elution of MeOH in CH$_2$Cl$_2$, 0-3%) to yield the title compound as a white solid (660 mg, 29%).

$^1$H NMR (400 MHz, CDCl$_3$): δ 5.47 (1H, dt, J=49.4, 9.4 Hz), 4.78 (1H, dddd, J=14.1, 11.9, 9.3, 5.0 Hz), 3.84 (1H, s), 2.41 (1H, ddd, J=15.5, 10.2, 5.3 Hz), 2.27 (1H, ddd, J=15.8, 9.7, 6.6 Hz), 2.06 (3H, s), 1.97-1.89 (2H, m), 1.86-1.80 (3H, m), 1.70-1.14 (19H, m), 0.99 (3H, s), 0.94 (3H, d, J=6.2 Hz), 0.92 (3H, t, J=7.1 Hz), 0.67 (3H, s) ppm.

$^{19}$F NMR ($^1$H non-decoupled, 376 MHz, CDCl$_3$): δ−188.6 (1F, dt, J=50.3, 12.1 Hz) ppm.

LRMS (ESI$^+$) m/z: 498.2, [M+NH$_4$]$^+$, 100%.

G. 3α-Acetoxy-4β-fluoro-6α-ethyl-7α-hydroxyl-5β-cholan-24-oyl azide

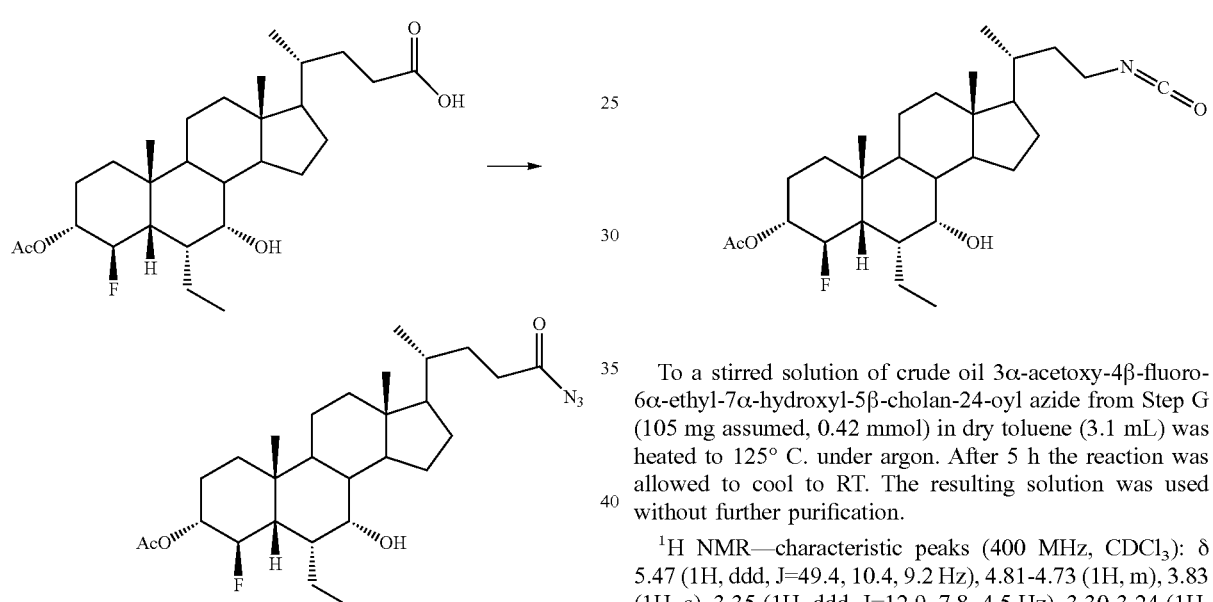

To a stirred solution of 3α-acetoxy-4β-fluoro-6α-ethyl-7α-hydroxyl-5β-cholanic acid from Step F (200 mg, 0.42 mmol) in dry THF (4 mL) at RT was added Et$_3$N (0.12 mL, 0.83 mmol, ~2.0 equiv.) dropwise under argon. After addition the reaction mixture was cooled to 0° C. and diphenylphosphoryl azide (0.13 mL, 0.62 mmol, ~1.5 equiv.) added dropwise. After addition the reaction mixture was stirred for 3 h behind a blast shield. Upon completion the reaction was quenched with brine (5 mL) and diluted with CH$_2$Cl$_2$ (5 mL). The organic phase was removed and the aqueous phase back extracted with CH$_2$Cl$_2$ (3×5 mL). Organic phases combined, dried over MgSO$_4$, filtered and concentrated in vacuo at 0° C. to yield a yellow oil. The resulting oil was used without further purification.

$^1$H NMR—characteristic peaks (400 MHz, CDCl$_3$): δ 5.47 (1H, ddd, J=49.4, 10.4, 9.2 Hz), 4.82-4.74 (1H, m), 3.83 (1H, s), 2.38 (1H, ddd, J=15.8, 10.0, 5.3 Hz), 2.29-2.23 (1H, m), 2.06 (3H, s), 0.98 (3H, s), 0.920 (3H, d, J=6.5 Hz), 0.919 (3H, t, J=7.2 Hz), 0.67 (3H, s) ppm.

$^{19}$F NMR ($^1$H non-decoupled, 376 MHz, CDCl$_3$): δ−186.8 (1F, dt, J=50.3 Hz) ppm.

H. 3α-Acetoxy-4β-fluoro-6α-ethyl-7α-hydroxyl-24-nor-5β-cholan-23-yl isocyanate

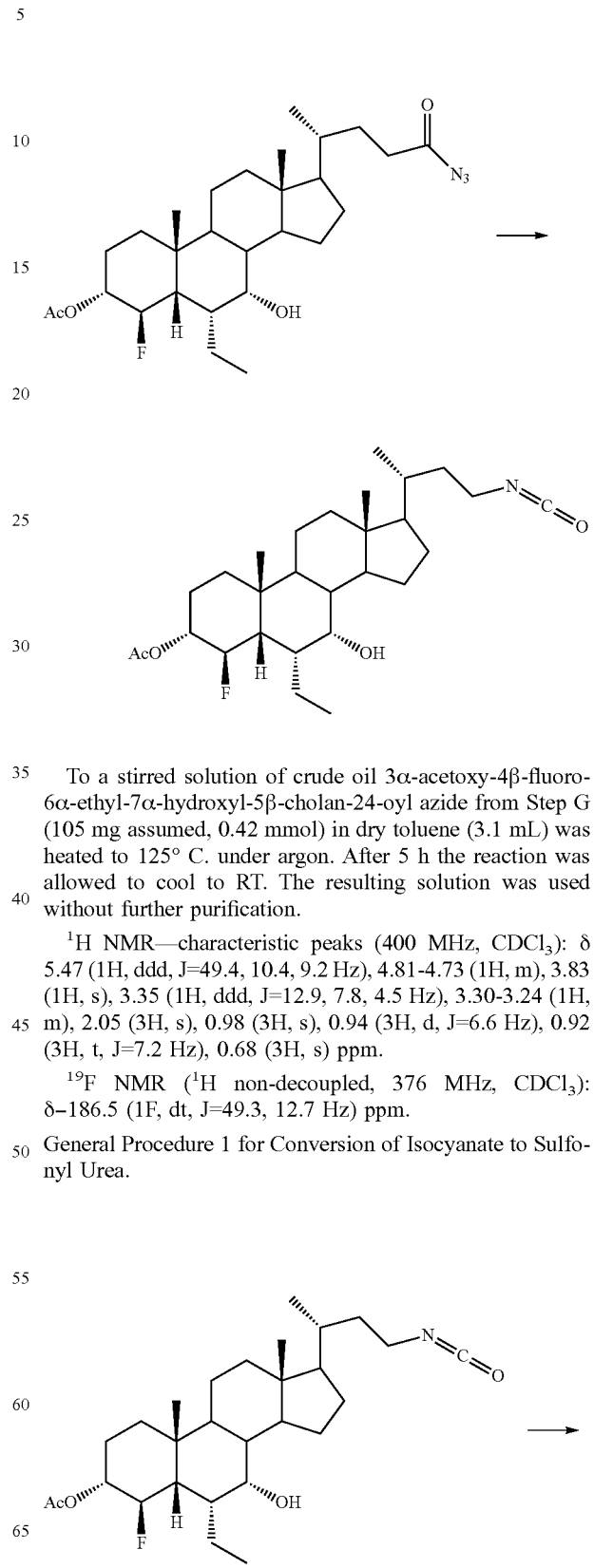

To a stirred solution of crude oil 3α-acetoxy-4β-fluoro-6α-ethyl-7α-hydroxyl-5β-cholan-24-oyl azide from Step G (105 mg assumed, 0.42 mmol) in dry toluene (3.1 mL) was heated to 125° C. under argon. After 5 h the reaction was allowed to cool to RT. The resulting solution was used without further purification.

$^1$H NMR—characteristic peaks (400 MHz, CDCl$_3$): δ 5.47 (1H, ddd, J=49.4, 10.4, 9.2 Hz), 4.81-4.73 (1H, m), 3.83 (1H, s), 3.35 (1H, ddd, J=12.9, 7.8, 4.5 Hz), 3.30-3.24 (1H, m), 2.05 (3H, s), 0.98 (3H, s), 0.94 (3H, d, J=6.6 Hz), 0.92 (3H, t, J=7.2 Hz), 0.68 (3H, s) ppm.

$^{19}$F NMR ($^1$H non-decoupled, 376 MHz, CDCl$_3$): δ−186.5 (1F, dt, J=49.3, 12.7 Hz) ppm.

General Procedure 1 for Conversion of Isocyanate to Sulfonyl Urea.

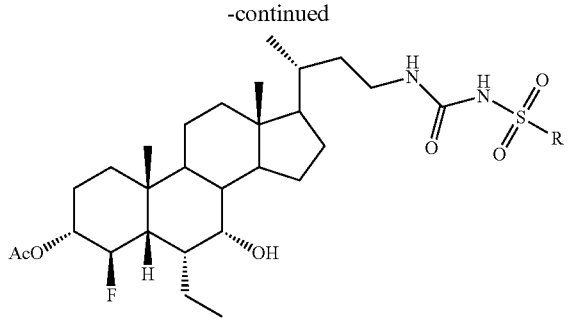

To a stirred crude solution of 3α-acetoxy-4β-fluoro-6α-ethyl-7α-hydroxyl-24-nor-5β-cholan-23-yl isocyanate from Step H in toluene was added sulphonamide (~1.5 equiv.) and DBU (~1.5 equiv.) and stirred for a 16 h. Upon completion the reaction was quenched via dropwise addition of 1M HCl (2 mL) and diluted with EtOAc (5 mL). The organic phase was removed and the aqueous phase back extracted with EtOAc (3×5 mL). Organic phases combined, dried over MgSO₄, filtered and concentrated in vacuo. The resultant residue was purified via column chromatography (gradient elution of acetone in PE 40-60, 5-20%) to yield the required sulfonylurea.

N,N'-(3α-Acetoxy-4β-fluoro-6α-ethyl-7α-hydroxyl-24-nor-5β-cholan-23-yl)-p-toluene sulfonyl urea (Intermediate 1)

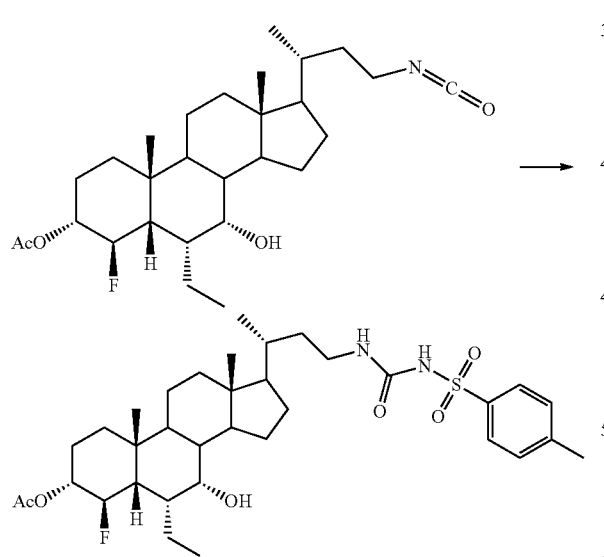

Prepared according to general procedure 1 using 53.4 mg of p-toluenesulfonamide to afford Intermediate 1 as a yellow oil (51.7 mg, 38%).

$^1$H NMR (400 MHz, CDCl$_3$): δ 7.78 (2H, d, J=8.2 Hz), 7.32 (2H, d, J=8.3 Hz), 6.50 (1H, t, J=4.8 Hz), 5.47 (1H, dt, J=49.4, 9.8 Hz), 4.83-4.73 (1H, m), 3.83 (1H, s), 3.33-3.25 (1H, m), 3.19-3.11 (1H, m), 2.44 (3H, s), 2.06 (3H, s), 1.96-1.80 (5H, m), 1.72-1.38 (15H, m), 1.23-1.14 (5H, m), 0.99 (3H, s), 0.93 (3H, d, J=6.6 Hz), 0.92 (3H, t, J=7.5 Hz), 0.65 (3H, s) ppm.

$^{19}$F NMR ($^1$H non-decoupled, 376 MHz, CDCl$_3$): δ−186.6 (1F, dt, J=49.0, 12.8 Hz) ppm.

LRMS (ESI$^+$) m/z: 666.4, [M+NH$_4$]$^+$, 100%.

N,N'-(3α-Acetoxy-4β-fluoro-6α-ethyl-7α-hydroxyl-24-nor-5β-cholan-23-yl)-benzene sulfonyl urea (Intermediate 2)

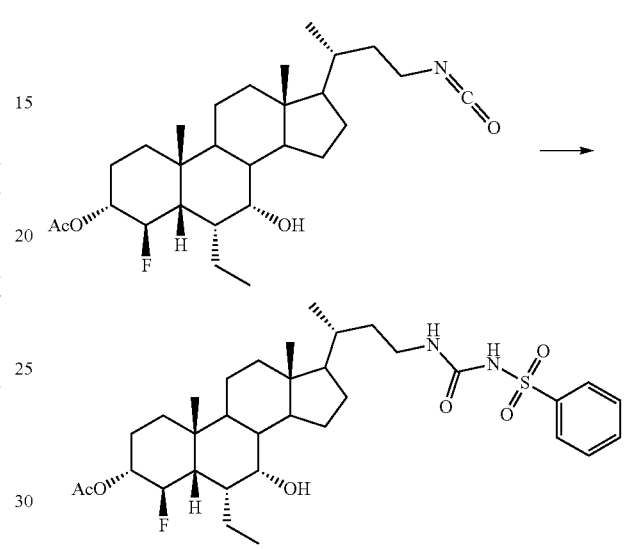

Prepared according to general procedure 1 using 49.0 mg of benzenesulfonamide to afford Intermediate 2 as a yellow oil (49.9 mg, 38%).

$^1$H NMR (400 MHz, CDCl$_3$): δ 7.90 (2H, d, J=7.6 Hz), 7.63 (1H, t, J=7.0 Hz), 7.50 (2H, t, J=7.7 Hz), 6.60 (1H, s), 5.48 (1H, dt, J=49.2, 9.8 Hz), 4.84-4.74 (1H, m), 3.83 (1H, s), 3.31-3.25 (1H, m), 3.18-3.10 (1H, m), 2.06 (3H, s), 1.95-1.80 (5H, m), 1.69-1.38 (13H, m), 1.29-1.12 (7H, m), 0.99 (3H, s), 0.93 (3H, d, J=6.7 Hz), 0.92 (3H, t, J=7.0 Hz), 0.65 (3H, s) ppm.

$^{19}$F NMR ($^1$H non-decoupled, 376 MHz, CDCl$_3$): δ−186.5 (1F, dt, J=48.6, 12.1 Hz) ppm.

LRMS (ESI$^+$) m/z: 652.3, [M+NH$_4$]$^+$, 100%.

N,N'-(3α-Acetoxy-4β-fluoro-6α-ethyl-7α-hydroxyl-24-nor-5β-cholan-23-yl)-4-(tert-butyl)benzene sulfonyl urea (Intermediate 3)

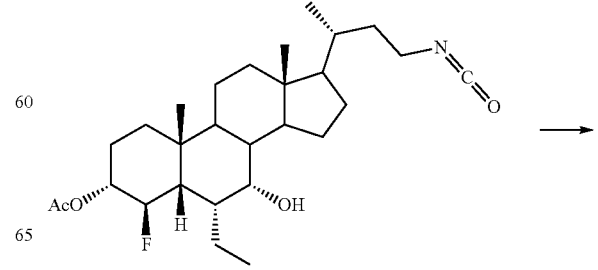

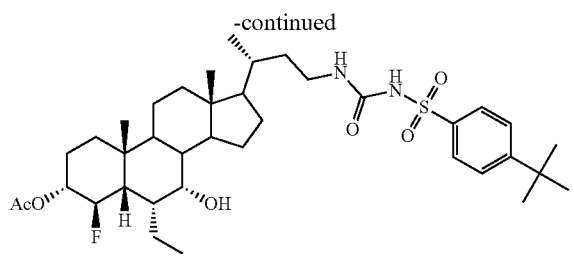

Prepared according to general procedure 1 using 53.2 mg of 4-(tert-butyl)benzenesulfonamide to afford the Intermediate 3 as a colourless oil (81.6 mg, 71%).

$^{1}$H NMR (400 MHz, CDCl$_{3}$): δ 7.81 (2H, d, J=8.7 Hz), 7.54 (2H, d, J=8.7 Hz), 6.56 (1H, s), 5.48 (1H, ddd, J=49.4, 10.4, 9.3 Hz), 4.83-4.73 (1H), 3.84 (1H, s), 3.33-3.29 (1H, m), 3.21-3.14 (1H, m), 2.07 (3H, s), 1.97-1.80 (4H, m), 1.74-1.44 (13H, m), 1.36 (9H, s), 1.29-1.16 (7H, m), 0.99 (3H, s), 0.95 (3H, d, J=6.6 Hz), 0.93 (3H, t, J=7.0 Hz), 0.67 (3H, s) ppm.

$^{19}$F NMR ($^{1}$H non-decoupled, 376 MHz, CDCl$_{3}$): δ−186.6 (1F, dt, J=49.9, 13.2 Hz) ppm.

LRMS (ESI$^{+}$) m/z: 708.4, [M+NH$_{4}$]$^{+}$, 100%.

N,N'-(3α-Acetoxy-4β-fluoro-6α-ethyl-7α-hydroxyl-24-nor-5β-cholan-23-yl)-m-toluene sulfonyl urea
(Intermediate 4)

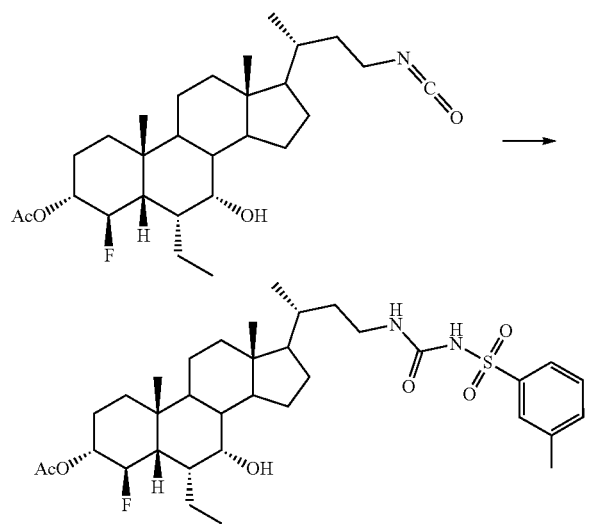

Prepared according to general procedure 1 using 42.6 mg of m-toluenesulfonamide to afford Intermediate 4 as a colourless oil (85.7 mg, 80%).

$^{1}$H NMR (400 MHz, CDCl$_{3}$): δ 7.71-7.68 (2H, m), 7.45-7.38 (2H, m), 6.54 (1H, s), 5.47 (1H, ddd, J=49.4, 10.3, 9.4 Hz), 4.83-4.73 (1H, m), 3.83 (1H, s), 3.33-3.26 (1H, m), 3.19-3.12 (1H, m), 2.42 (3H, s), 2.06 (3H, s), 1.96-1.80 (4H, m), 1.72-1.11 (21H, m), 0.99 (3H, s), 0.94 (3H, d, J=6.6 Hz), 0.93 (3H, t, J=7.3 Hz), 0.65 (3H, s) ppm.

$^{19}$F NMR ($^{1}$H non-decoupled, 376 MHz, CDCl$_{3}$): δ−186.6 (1F, dt, J=49.4, 13.4 Hz) ppm.

LRMS (ESI$^{+}$) m/z: 666.3, [M+NH$_{4}$]$^{+}$, 100%.

N,N'-(3α-Acetoxy-4β-fluoro-6α-ethyl-7α-hydroxyl-24-nor-5β-cholan-23-yl)-o-toluene sulfonyl urea
(Intermediate 5)

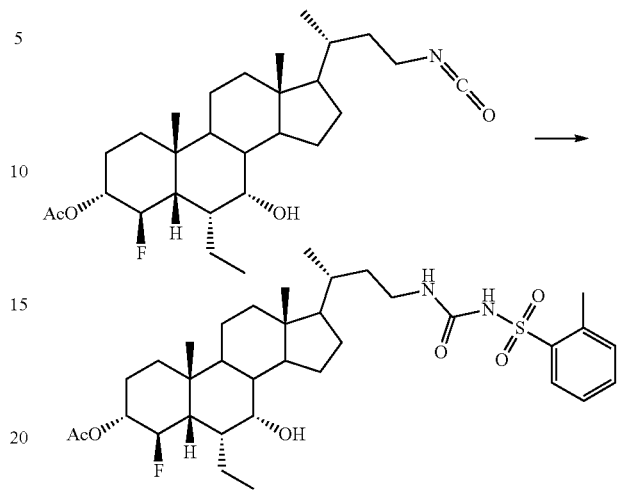

Prepared according to general procedure 1 using 42.6 mg of o-toluenesulfonamide to afford Intermediate 5 as a colourless oil (55.4 mg, 51%).

$^{1}$H NMR (400 MHz, CDCl$_{3}$): δ 7.94 (1H, dd, J=8.3, 1.0 Hz), 7.51 (1H, td, J=7.6, 1.2 Hz), 7.34 (2H, d, J=7.3 Hz), 6.47 (1H, s), 5.47 (1H, dt, J=49.3, 9.5 Hz), 4.83-4.73 (1H, m), 3.83 (1H, s), 3.28-3.22 (1H, m), 3.15-3.08 (1H, m), 2.65 (3H, s), 2.21-2.17 (1H, m), 2.06 (3H, s), 1.94-1.80 (4H, m), 1.68-1.10 (20H, m), 0.98 (3H, s), 0.92 (3H, d, J=6.7 Hz), 0.90 (3H, t, J=7.3 Hz), 0.63 (3H, s) ppm.

$^{19}$F NMR ($^{1}$H non-decoupled, 376 MHz, CDCl$_{3}$): δ−186.6 (1F, dt, J=49.9, 12.4 Hz) ppm.

LRMS (ESI$^{+}$) m/z: 666.3, [M+NH$_{4}$]$^{+}$, 100%.

General Procedure 2 for Deprotection of 3α-acetate sulfonyl ureas

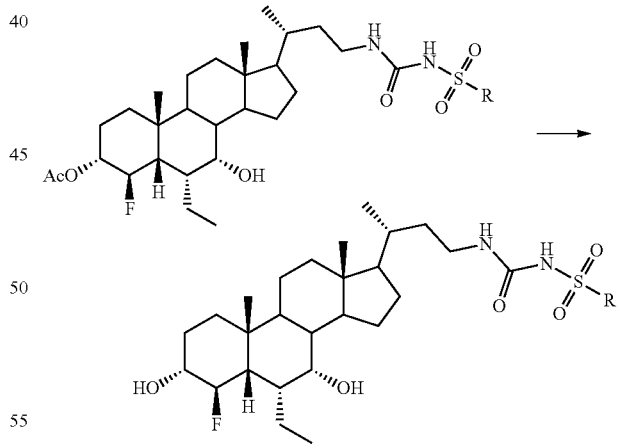

To a flask charged with the protected sulfonyl urea was added a solution of NaOH in MeOH (5% solution, 10 mL) and stirred for 16 h. Upon completion the reaction was acidified to pH 7.0 with 1M HCl and diluted with EtOAc (10 mL). The organic phase was removed and the aqueous phase back extracted with EtOAc (3×10 mL). Organic phases combined, washed with NaHCO$_{3}$ solution (50 mL), dried over MgSO$_{4}$, filtered and concentrated in vacuo. The resultant residue was purified via column chromatography (gradient elution of MeOH in CH$_{2}$Cl$_{2}$, 0-5%) to yield the deprotected sulfonyl urea.

N,N'-(3α,7α-Dihydroxyl-4β-fluoro-6α-ethyl-24-nor-5β-cholan-23-yl)-p-toluene sulfonyl urea (Compound 1)

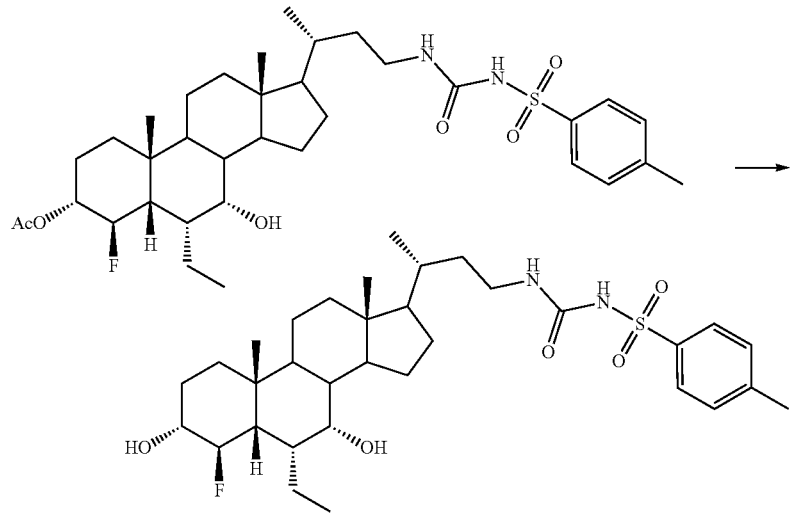

Prepared according to general procedure 2 using 49.7 mg of Intermediate 1 to afford Compound 1 as a colourless residue (18.6 mg, 40%).

$^1$H NMR (400 MHz, CDCl$_3$): δ 7.78 (2H, d, J=8.3 Hz), 7.34 (2H, d, J=8.1 Hz), 6.50 (1H, t, J=4.8 Hz), 5.32 (1H, ddd, J=50.0, 10.0, 9.2 Hz), 3.83 (1H, s), 3.59-3.51 (1H, m), 3.33-3.26 (1H, m), 3.21-3.12 (1H, m), 2.46 (3H, s), 1.96-1.06 (26H, m), 0.98 (3H, s), 0.94 (3H, t, J=6.2 Hz), 0.93 (3H, t, J=6.4 Hz), 0.66 (3H, s) ppm.

$^{19}$F NMR ($^1$H non-decoupled, 376 MHz, CDCl$_3$): δ−188.8 (1F, dt, J=50.3, 10.4 Hz) ppm.

LRMS (ESI$^+$) m/z: 624.4, [M+NH$_4$]$^+$, 100%.

N,N'-(3α,7α-Dihydroxyl-4β-fluoro-6α-ethyl-24-nor-5β-cholan-23-yl)-benzene sulfonyl urea (Compound 2)

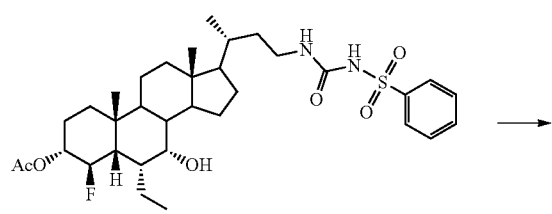

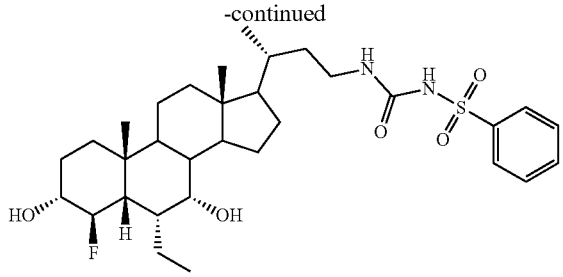

Prepared according to general procedure 2 using 44.8 mg of Intermediate 2 to afford Compound 2 as a colourless residue (28.5 mg, 64%).

$^1$H NMR (400 MHz, CDCl$_3$): δ 7.91 (2H, d, J=7.5 Hz), 7.65 (1H, t, J=7.3 Hz), 7.54 (2H, t, J=7.8 Hz), 6.51 (1H, s), 5.31 (1H, ddd, J=50.1, 10.3, 9.1 Hz), 3.82 (1H, s), 3.60-3.50 (1H, m), 3.35-3.26 (1H, m), 3.20-3.12 (1H, m), 1.95-1.36 (17H, m), 1.27-1.11 (9H, m), 0.97 (3H, s), 0.94 (3H, d, J=6.2 Hz), 0.93 (3H, t, J=6.7 Hz), 0.65 (3H, s) ppm.

$^{19}$F NMR ($^1$H non-decoupled, 376 MHz, CDCl$_3$): δ−189.0 (1F, dt, J=50.3, 12.1 Hz) ppm.

LRMS (ESI$^+$) m/z: 610.2, [M+NH$_4$]$^+$, 100%.

N,N'-(3α,7α-Dihydroxyl-4β-fluoro-6α-ethyl-24-nor-5β-cholan-23-yl)-4-(tert-butyl) benzene sulfonyl urea (Compound 3)

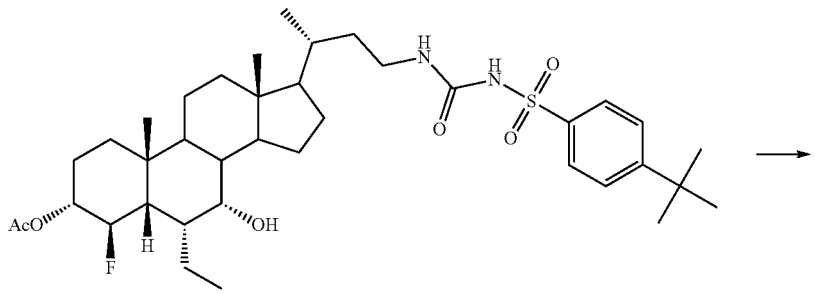

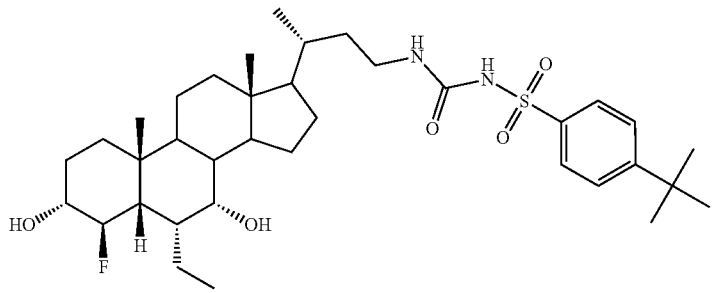

Prepared according to general procedure 2 using 79.6 mg of Intermediate 3 to afford Compound 3 as a colourless residue (50.7 mg, 65%).

$^1$H NMR (400 MHz, CDCl$_3$): δ 7.82 (2H, d, J=8.6 Hz), 7.53 (2H, t, J=8.4 Hz), 6.54 (1H, s), 5.32 (1H, ddd, J=49.9, 10.3, 9.1 Hz), 3.82 (1H, s), 3.60-3.50 (1H, m), 3.35-3.25 (1H, m), 3.19-3.11 (1H, m), 1.95-1.41 (16H, m), 1.34 (9H, s), 1.28-1.08 (10H, m), 0.97 (3H, s), 0.930 (3H, t, J=6.9 Hz), 0.927 (3H, d, J=6.2 Hz), 0.65 (3H, s) ppm.

$^{19}$F NMR ($^1$H non-decoupled, 376 MHz, CDCl$_3$): δ−188.8 (1F, dt, J=50.3, 12.1 Hz) ppm.

LRMS (ESI$^+$) m/z: 666.4, [M+NH$_4$]$^+$, 100%.

N,N'-(3α,7α-Dihydroxyl-4β-fluoro-6α-ethyl-24-nor-5β-cholan-23-yl)-m-toluene sulfonyl urea (Compound 4)

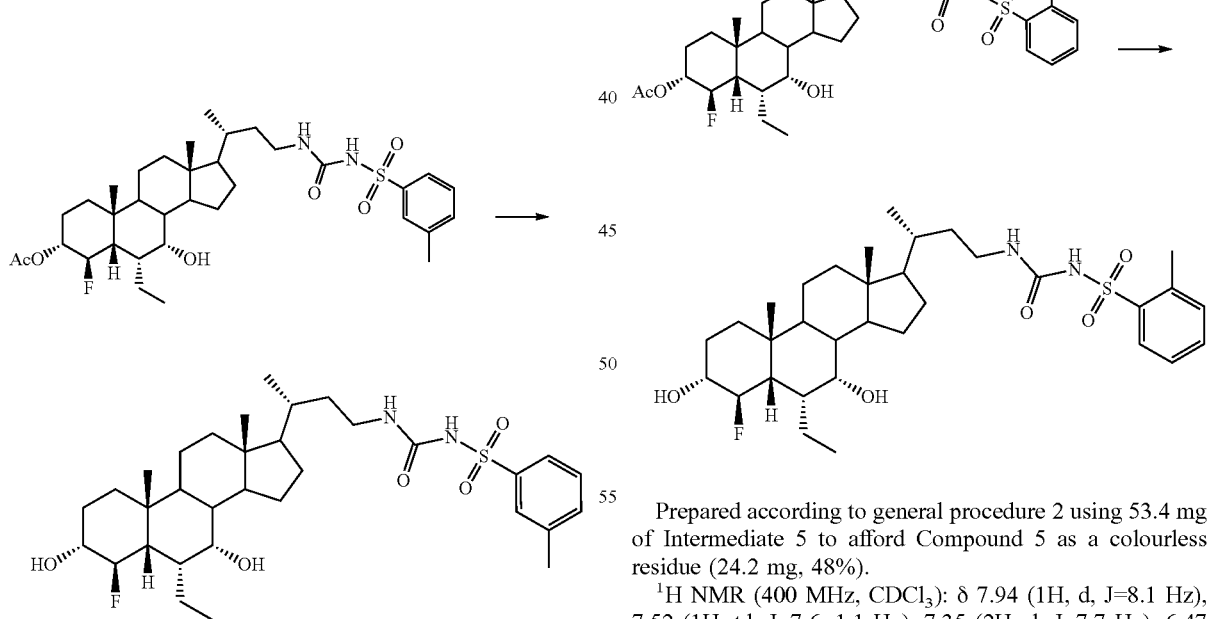

Prepared according to general procedure 2 using 83.7 mg of Intermediate 4 to afford Compound 4 as a colourless residue (29.0 mg, 37%).

$^1$H NMR (400 MHz, CDCl$_3$): δ 7.71-7.69 (2H, m), 7.45-7.38 (2H, m), 6.52 (1H, s), 5.32 (1H, ddd, J=49.9, 10.4, 8.9 Hz), 3.82 (1H, s), 3.60-3.50 (1H, m), 3.35-3.26 (1H, m), 3.20-3.10 (1H, m), 2.43 (3H, s), 1.95-1.39 (17H, m), 1.28-1.11 (10H, m), 0.97 (3H, s), 0.94 (3H, d, J=6.2 Hz), 0.93 (3H, t, J=6.5 Hz), 0.65 (3H, s) ppm.

$^{19}$F NMR ($^1$H non-decoupled, 376 MHz, CDCl$_3$): δ−188.9 (1F, dt, J=48.6, 10.4 Hz) ppm.

LRMS (ESI$^+$) m/z: 624.3, [M+NH$_4$]$^+$, 100%.

N,N'-(3α,7α-Dihydroxyl-4β-fluoro-6α-ethyl-24-nor-5β-cholan-23-yl)-o-toluene sulfonyl urea (Compound 5)

Prepared according to general procedure 2 using 53.4 mg of Intermediate 5 to afford Compound 5 as a colourless residue (24.2 mg, 48%).

$^1$H NMR (400 MHz, CDCl$_3$): δ 7.94 (1H, d, J=8.1 Hz), 7.52 (1H, td, J=7.6, 1.1 Hz), 7.35 (2H, d, J=7.7 Hz), 6.47 (1H, t, J=4.6 Hz), 5.31 (1H, ddd, J=49.9, 10.4, 8.9 Hz), 3.82 (1H, s), 3.60-3.50 (1H, m), 3.30-3.22 (1H, m), 3.17-3.08 (1H, m), 2.67 (3H, s), 1.94-1.06 (25H, m), 0.97 (3H, s), 0.91 (3H, t, J=7.5 Hz), 0.90 (3H, d, J=6.6 Hz), 0.63 (3H, s) ppm.

$^{19}$F NMR ($^1$H non-decoupled, 376 MHz, CDCl$_3$): δ−189.0 (1F, dt, J=48.6, 12.1 Hz) ppm.

LRMS (ESI$^+$) m/z: 624.3, [M+NH$_4$]$^+$, 100%.

N,N'-(3α,7α-Dihydroxyl-4β-fluoro-6α-ethyl-24-nor-
5β-cholan-23-yl)-p-fluorobenzene sulfonyl urea
(Compound 6)

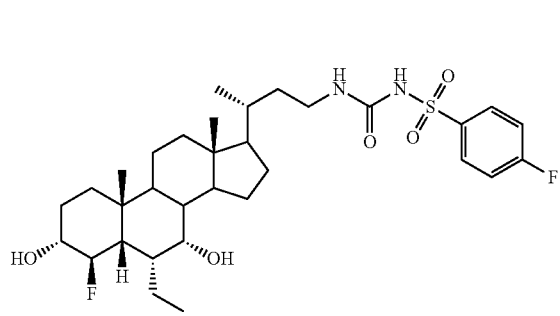 [SMILES: CC[C@@H]1[C@@H]2[C@@H](F)[C@H](O)CC[C@]2(C)C2CC[C@@]3(C)C(CCC3[C@H](C)CCNC(=O)NS(=O)(=O)c3ccc(F)cc3)C2[C@@H]1O]

This compound was prepared by a method analogous to that described above for Compounds 1-5.

¹H NMR (400 MHz, MeOD): δ 7.93-7. (2H, m), 7.20-7.17 (2H, m), 5.19 (1H, dq, J=49.3, 10.5, 8.9 Hz), 3.65 (1H, s), 3.31 (1H, m), 3.06 (1H, m), 2.95 (1H, m), 1.94-1.06 (21H, m), 0.84-0.76 (9H, m), 0.63 (3H, s) ppm.

¹⁹F NMR (¹H non-decoupled, 376 MHz, MeOD): δ −107.29 (1F, m), −186.6 (1F, m) ppm.

N,N'-(3α,7α-Dihydroxyl-4β-fluoro-6α-ethyl-24-nor-
5β-cholan-23-yl)-m-fluorobenzene sulfonyl urea
(Compound 7)

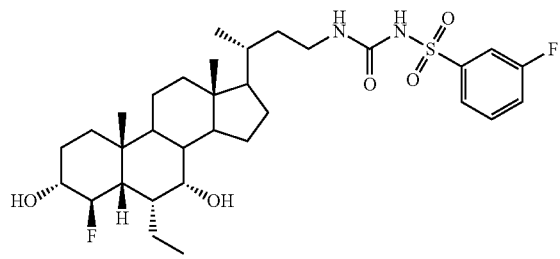 [SMILES: CC[C@@H]1[C@@H]2[C@@H](F)[C@H](O)CC[C@]2(C)C2CC[C@@]3(C)C(CCC3[C@H](C)CCNC(=O)NS(=O)(=O)c3cccc(F)c3)C2[C@@H]1O]

This compound was prepared by a method analogous to that described above for Compounds 1-5.

¹H NMR (400 MHz, CDCl₃) δ 7.71 (ddd, J=7.8, 1.6, 1.0 Hz, 1H), 7.61 (br dt, J=8.0, 2.1 Hz, 1H), 7.54 (td, J=8.1, 5.3 Hz, 1H), 7.35 (tdd, J=8.3, 2.6, 0.7 Hz, 1H), 6.50 (br t, J=5.1 Hz, 1H), 5.32 (ddd, J=49.9, 10.5, 8.8 Hz, 1H), 3.83 (s, 1H), 3.55 (dddd, J=14.2, 12.0, 8.8, 5.1 Hz, 1H), 3.32 (ddt, J=13.1, 9.5, 5.1 Hz, 1H), 3.18 (dtd, J=13.0, 8.0, 6.1 Hz, 1H), 1.96-1.86 (m, 2H), 1.85-1.74 (m, 2H), 1.71-1.58 (m, 6H), 1.54-1.41 (m, 7H), 1.31-1.08 (m, 9H), 0.98 (s, 3H), 0.95 (d, J=6.5 Hz, 3H), 0.93 (t, J=7.0 Hz, 3H), 0.66 (s, 3H) ppm;

¹⁹F NMR (376 MHz, CDCl₃) δ −108.9 (br s, 1F), −188.9 (br d, J=50.3 Hz, 1F) ppm;

¹⁹F {1H} NMR (376 MHz, CDCl₃) δ −108.9 (s, 1F), −188.9 (s, 1F) ppm;

N,N'-(3α,7α-Dihydroxyl-4β-fluoro-6α-ethyl-24-nor-
5β-cholan-23-yl)-o-fluorobenzene sulfonyl urea
(Compound 8)

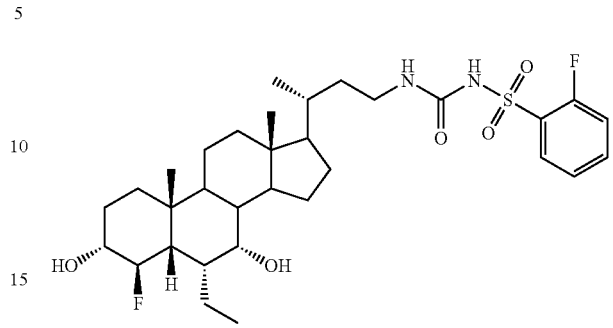

This compound was prepared by a method analogous to that described above for Compounds 1-5.

¹H NMR (400 MHz, CDCl₃) δ 7.91 (ddd, J=7.8, 7.2, 1.7 Hz, 1H), 7.67 (dddd, J=8.3, 7.5, 5.0, 1.7 Hz, 1H), 7.33 (td, J=7.7, 1.1 Hz, 1H), 7.28 (ddd, J=10.0, 8.4, 0.9 Hz, 1H), 6.45 (br t, J=5.1 Hz, 1H), 5.31 (ddd, J=49.9, 10.5, 8.7 Hz, 1H), 3.83 (br s, 1H), 3.55 (dddd, J=13.8, 11.9, 8.9, 5.4 Hz, 1H), 3.29 (ddt, J=12.8, 9.4, 5.3 Hz, 1H), 3.16 (dtd, J=13.5, 7.8, 5.6 Hz, 1H), 1.96-1.74 (m, 4H), 1.71-1.39 (m, 14H), 1.25-1.09 (m, 8H), 0.98 (s, 3H), 0.94 (t, J=7.3 Hz, 3H), 0.93 (d, J=6.6 Hz, 3H), 0.65 (s, 3H) ppm;

¹⁹F NMR (376 MHz, CDCl₃) δ −109.0 (ddd, J=10.4, 6.9, 5.2 Hz, 1F), −189.2 (dt, J=50.3, 11.3 Hz, 1F) ppm;

¹⁹F {1H} NMR (376 MHz, CDCl₃) δ −109.0 (s, 1F), −189.2 (s, 1F) ppm.

N,N'-(3α,7α-Dihydroxyl-4β-fluoro-6α-ethyl-24-nor-
5β-cholan-23-yl)-p-(trifluoromethyl)benzene sulfonyl urea (Compound 9)

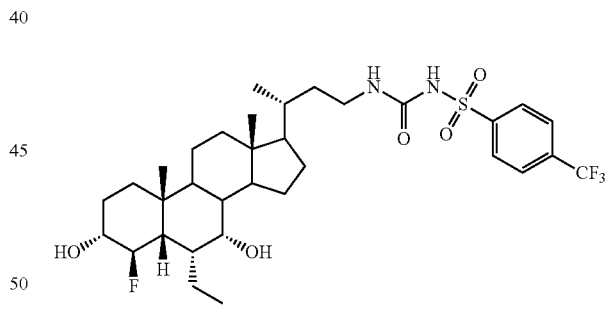

This compound was prepared by a method analogous to that described above for Compounds 1-5.

¹H NMR (400 MHz, CDCl₃) δ 8.07 (d, J=8.2 Hz, 2H), 7.80 (d, J=8.1 Hz, 2H), 6.46 (br t, J=4.8 Hz, 1H), 5.32 (ddd, J=49.8, 10.4, 8.8 Hz, 1H), 3.82 (s, 1H), 3.55 (dddd, J=14.2, 11.9, 8.8, 5.4 Hz, 1H), 3.28 (ddt, J=13.6, 7.7, 4.9 Hz, 1H), 3.15 (dtd, J=13.5, 7.6, 6.0 Hz, 1H), 1.96-1.75 (m, 4H), 1.72-1.55 (m, 7H), 1.53-1.37 (m, 7H), 1.25-1.06 (m, 8H), 0.97 (s, 3H), 0.933 (d, J=6.1 Hz, 3H), 0.927 (t, J=6.5 Hz, 3H), 0.63 (s, 3H) ppm;

¹⁹F NMR (376 MHz, CDCl₃) δ −63.5 (s, 3F), −188.5 (br d, J=48.6 Hz, 1F) ppm;

¹⁹F {1H} NMR (376 MHz, CDCl₃) δ −63.4 (s, 3F), −188.6 (br s, 1F) ppm.

N,N'-(3α,7α-Dihydroxyl-4β-fluoro-6α-ethyl-24-nor-5β-cholan-23-yl)-m-(trifluoromethyl)benzene sulfonyl urea (Compound 10)

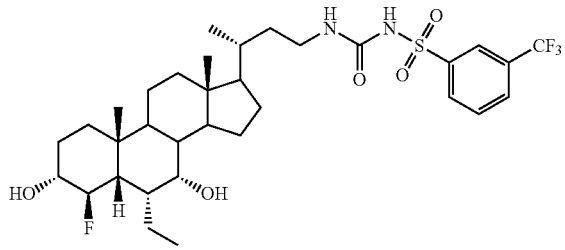 [SMILES: CC[C@@H]1[C@@H]2[C@@H](F)[C@H](O)CC[C@]2(C)C2CC[C@@]3(C)C(CCC3[C@H](C)CCNC(=O)NS(=O)(=O)c3cccc(C(F)(F)F)c3)C2[C@@H]1O]

This compound was prepared by a method analogous to that described above for Compounds 1-5.

$^1$H NMR (400 MHz, CDCl$_3$) δ 8.17 (s, 1H), 8.11 (d, J=8.0 Hz, 1H), 7.91 (br d, J=7.7 Hz, 1H), 7.71 (t, J=7.9 Hz, 1H), 6.49 (br t, J=4.7 Hz, 1H), 5.32 (ddd, J=49.9, 10.2, 9.1 Hz, 1H), 3.83 (s, 1H), 3.56 (dddd, J=14.1, 11.7, 8.7, 5.1 Hz, 1H), 3.32 (ddt, J=13.5, 9.4, 5.3 Hz, 1H), 3.17 (dtd, J=12.6, 7.8, 6.2 Hz, 1H), 1.96-1.87 (m, 2H), 1.84-1.74 (m, 2H), 1.72-1.58 (m, 6H), 1.53-1.41 (m, 7H), 1.29-1.09 (m, 9H), 0.98 (s, 3H), 0.95 (d, J=6.5 Hz, 3H), 0.93 (t, J=6.9 Hz, 3H), 0.66 (s, 3H) ppm;

$^{19}$F NMR (376 MHz, CDCl$_3$) δ−63.1 (s, 3F), −189.0 (br s, 1F) ppm;

$^{19}$F {1H} NMR (376 MHz, CDCl$_3$) δ−63.1 (s, 3F), −189.0 (br s, 1F) ppm.

N,N'-(3α,7α-Dihydroxyl-4β-fluoro-6α-ethyl-24-nor-5β-cholan-23-yl)-o-(trifluoromethyl)benzene sulfonyl urea (Compound 11)

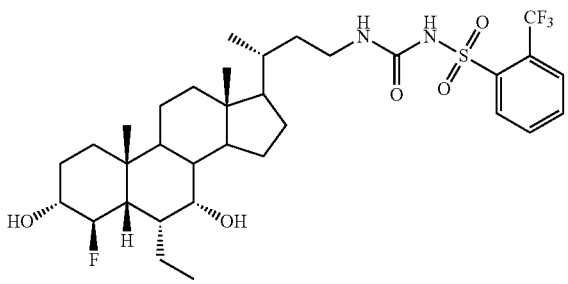 [SMILES: CC[C@@H]1[C@@H]2[C@@H](F)[C@H](O)CC[C@]2(C)C2CC[C@@]3(C)C(CCC3[C@H](C)CCNC(=O)NS(=O)(=O)c3ccccc3C(F)(F)F)C2[C@@H]1O]

This compound was prepared by a method analogous to that described above for Compounds 1-5.

$^1$H NMR (400 MHz, CDCl$_3$) δ 8.26 (dd, J=6.3, 2.3 Hz, 1H), 7.92 (dd, J=6.6, 2.3 Hz, 1H), 7.77 (m, 2H), 6.35 (br t, J=4.8 Hz, 1H), 5.31 (ddd, J=49.9, 10.4, 8.9 Hz, 1H), 3.82 (s, 1H), 3.56 (dddd, J=14.2, 12.1, 8.7, 5.1 Hz, 1H), 3.29 (ddt, J=13.5, 9.1, 5.1 Hz, 1H), 3.13 (dtd, J=13.5, 7.7, 6.2 Hz, 1H), 1.96-1.72 (m, 5H), 1.70-1.35 (m, 14H), 1.25-1.06 (m, 7H), 0.97 (s, 3H), 0.93 (d, J=7.0 Hz, 3H), 0.92 (t, J=6.5 Hz, 3H), 0.63 (s, 3H) ppm;

$^{19}$F NMR (376 MHz, CDCl$_3$) δ−58.0 (s, 3F), −188.9 (br d, J=48.6 Hz, 1F) ppm;

$^{19}$F {1H} NMR (376 MHz, CDCl$_3$) δ−58.0 (s, 3F), −188.9 (s, 1F) ppm.

N,N'-(3α,7α-Dihydroxyl-6α-ethyl-24-nor-5β-cholan-23-yl)-benzene sulfonyl urea (Comparative Compound A)

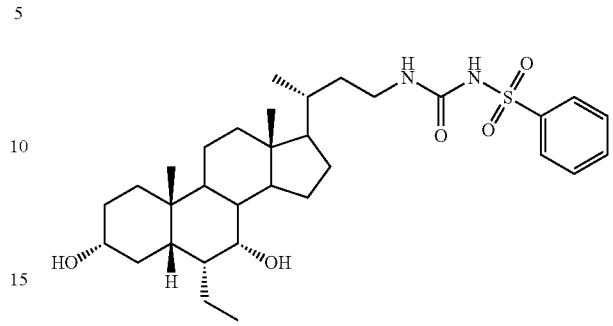

This compound was prepared by a method analogous to that described above for Compounds 5-9.

$^1$H NMR (400 MHz, MeOD): δ 7.86-7.81 (2H, m), 7.53 (1H, m), 7.47-7.41 (2H, m), 3.52 (1H, br. s), 3.22 (1H, m), 3.04 (1H, m), 2.93 (1H, m), 1.87-0.83 (25H, m), 0.81-0.76 (9H, m), 0.52 (3H, s) ppm.

Example 2—Alternative Synthesis of Compounds with Sulfonylurea-Substituted Side Chains The methods below are illustrated for 4β-fluoro derivatives but could also be used for 2β-fluorinated, 4,4-difluorinated or 2,4-difluoroinated compounds.

A. Methyl 6α-ethyl-4β-fluoro-7α-trimethylsiloxy-3-oxo-5β-cholan-24-oate

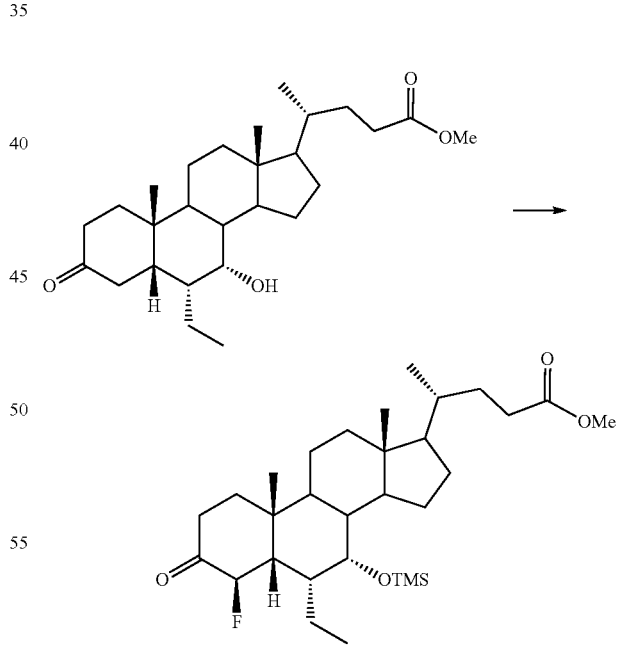

To a stirred, pre-cooled solution of diisopropylamine (0.78 mL, 5.54 mmol, ~12 equiv.) in dry THF (6.9 mL) at −78° C. was added n-BuLi in hexanes (1.44 mL, 2.31 mmol, ~5.0 equiv.) dropwise over 0.25 h under argon. After addition, trimethylsilylchloride (0.29 mL, 2.31 mmol, ~5.0 equiv.) was added and stirred for 1 h. A solution of methyl 6α-ethyl-7α-hydroxyl-3-oxo-5β-cholan-24-oate from Example 1, Step B (200 mg, 0.46 mmol) in dry THF (3 mL) and triethylamine (1.16 mL, 8.32 mmol, ~18 equiv.) were then added. After addition the reaction was gradually allowed to warm to −20° C. and stirred for 2 h. Upon completion the reaction was quenched via the dropwise addition of saturated NaHCO₃ (5 mL) and warmed to RT for 2 h. The organic phase was removed and the aqueous phase back extracted with EtOAc (3×10 mL). Organic phases were combined, washed with brine (30 mL), dried over MgSO₄, filtered and concentrated in vacuo to afford 271 mg of crude material as a yellow residue.

To a solution of the crude material (1.16 g, 2.3 mmol) in dry MeCN (55 mL) was charged SELECTFLUOR® (1.23 g, 3.47 mmol). After stirring at RT for 14,5 h the mixture was diluted with ethyl acetate (100 mL) and washed with a mixture of 5% NaHCO₃ (100 mL) and 10% NaCl (50 mL). The aqueous phase was extracted with ethyl acetate (3×100 mL) and the combined organic phases were dried over MgSO₄, filtered and concentrated in vacuo to afford an orange/yellow oil. The crude material was purified by column chromatography (SiO₂, 0-40% EtOAc in heptanes) to afford the title compound as a colourless oil (319.5 mg).

B. Methyl 6α-ethyl-4β-fluoro-7α-trimethylsiloxy-3α-hydroxyl-5β-cholan-24-oate

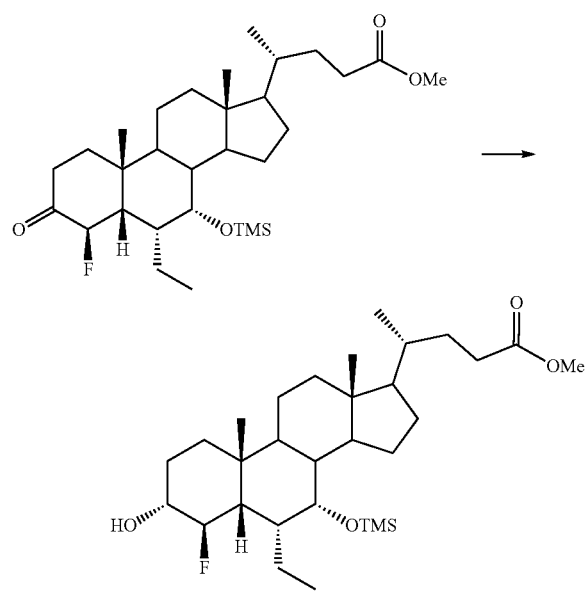

Crude methyl 6α-ethyl-4β-fluoro-7α-trimethylsiloxy-3-oxo-5β-cholan-24-oate from Step A (319.5 mg, 0.71 mmol) was dissolved in THF (28 mL) with stirring under argon. NaBH₄ (80.5 mg, 2.13 mmol) was charged and the reaction was stirred at RT for 16.5 h, after which additional NaBH₄ (0.24 g, 6.38 mmol) was charged. The mixture was stirred for an additional 4.5 h then water (20 μL) was charged and the mixture was stirred for ~60 h. After this time the reaction was quenched by the addition of water (15 mL) and diluted with EtOAc (50 mL). The phases were separated and the aqueous phase was extracted with EtOAc (3×50 mL). The combined extracts were dried over MgSO₄, filtered and concentrated in vacuo to afford a clear syrup (0.34 g). The crude material was purified by column chromatography (SiO₂, 0-40% EtOAc in heptane) to afford the title compound as a clear oil (162.3 mg).

C. Methyl 6α-ethyl-4β-fluoro-7α-trimethylsiloxy-3α-O-tert-butyldimethylsilyl-5β-cholan-24-oate

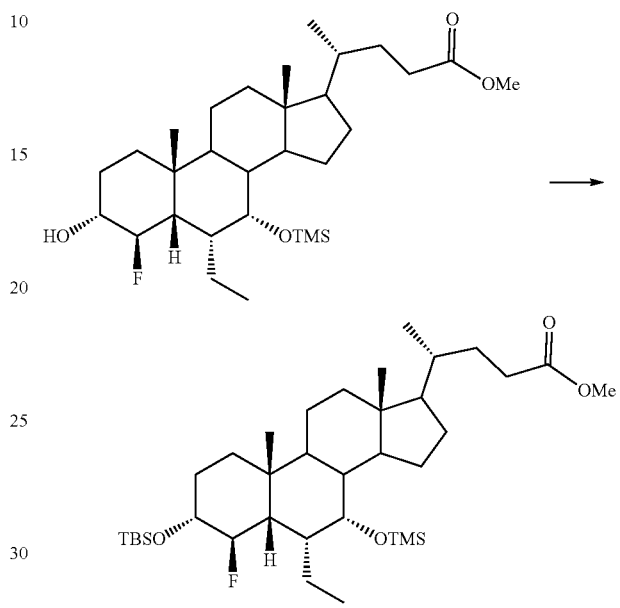

Methyl 6α-ethyl-4β-fluoro-7α-trimethylsiloxy-3α-hydroxyl-5β-cholan-24-oate from Step B (0.48 g, 0.92 mmol) was dissolved in dry DCM (12 mL) and cooled to 0° C. with stirring, under argon. 2,6-lutidine (1.1 mL, 9.17 mmol) was charged followed by the drop-wise addition of TBMDS-OTf (0.32 mL, 1.38 mmol). The reaction was warmed to RT and stirred for 24 h then cooled to 0° C. and quenched by the drop-wise addition of 10% citric acid (5 mL). The phases were separated and the aqueous phase was extracted with DCM (3×5 mL). The combined extracts were washed with 10% citric acid (5 mL), aq. NaHCO₃ (5 mL) and water (5 mL), dried over MgSO₄, filtered and concentrated in vacuo to a yellow oil (0.69 g). The crude material was purified by column chromatography (SiO₂, 0-20% EtOAc in heptane) to afford the title compound as a clear oil (0.58 g).

D. 6α-Ethyl-4β-fluoro-7α-trimethylsiloxy-3α-O-tert-butyldimethylsilyl-5β-cholanic Acid

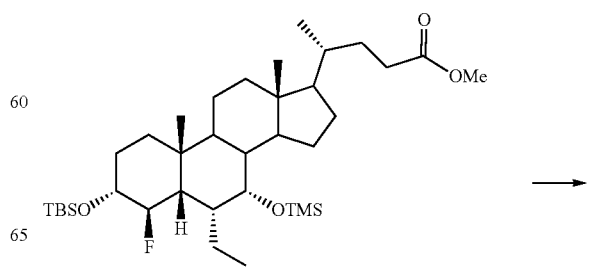

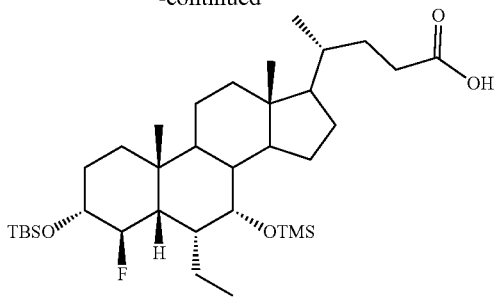

Methyl 6α-ethyl-4β-fluoro-7α-trimethylsiloxy-3α-O-tert-butyldimethylsilyl-5β-cholan-24-oate (0.58 g) from Step C was dissolved in IPA (5.8 mL) with stirring. 0.5 M NaOH (5.8 mL) was charged and the reaction was stirred at RT for 15 h. The reaction mixture was concentrated under reduced pressure to ~half the volume then water (5 mL) was charged and the solution was neutralised by the addition of 2 M $H_2SO_4$ and diluted with EtOAc (10 mL). The mixture was acidified to pH 1 with 2 M $H_2SO_4$, the phases were separated and the aqueous phase was extracted with EtOAc (10 mL). The combined extracts were washed with water (5 mL) and brine (5 mL), dried over $MgSO_4$, filtered and concentrated in vacuo to afford a white foam (0.52 g). The crude material was purified by column chromatography ($SiO_2$, 0-50% acetone in toluene) to afford the title compound as a white solid (0.41 g, 72%).

E. 6α-Ethyl-4β-fluoro-7α-trimethylsiloxy-3α-O-tert-butyldimethylsilyl-5β-cholan-24-oyl azide

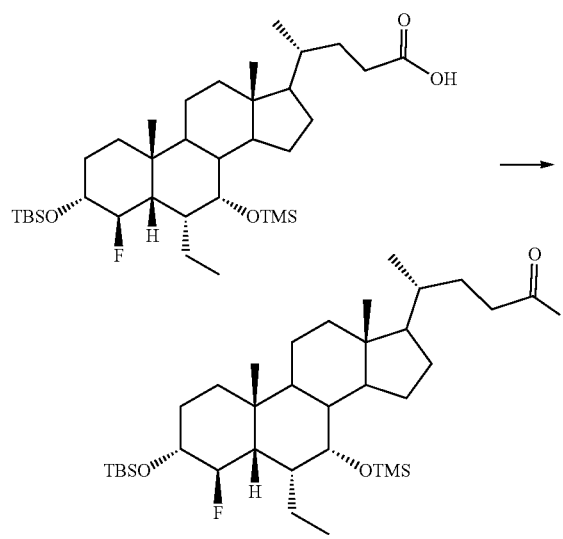

To a stirred solution of 6α-ethyl-4β-fluoro-7α-trimethylsiloxy-3α-O-tert-butyldimethylsilyl-5β-cholanic acid from Step D (197 mg, 0.32 mmol) in dry THF (3.2 mL) at RT was added $Et_3N$ (0.09 mL, 0.64 mmol, ~2.0 equiv.) dropwise under argon. After addition the reaction mixture was cooled to 0° C. and diphenylphosphoryl azide (0.1 mL, 0.48 mmol, ~1.5 equiv.) added dropwise. After addition the reaction mixture was stirred for 2.5 h behind a blast shield. Upon completion the reaction was quenched with brine (3 mL) and extracted with DCM (3×5 mL). The combined organic phases were dried over $MgSO_4$, filtered and concentrated in vacuo at 0° C. The resulting oil was used without further purification.

General Procedure 3 for Formation of Sulfonylureas

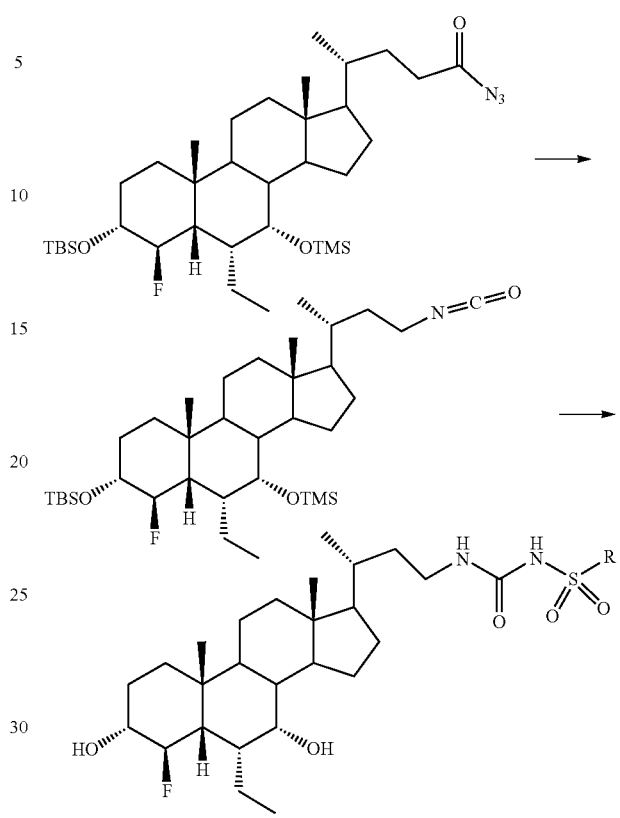

A stirred solution of crude 6α-ethyl-4β-fluoro-7α-trimethylsiloxy-3α-O-tert-butyldimethylsilyl-5β-cholan-24-oyl azide from Step E of Example 2 (69 mg) in dry toluene (2.1 mL) was heated to 125° C. under argon. After 5 h the reaction was allowed to cool to RT. The resulting solution was used without further purification. The solution was stirred under argon and the sulfonamide (1.5 equivalents) and DBU (1.5 equivalents) were charged. Upon completion the reaction was quenched via dropwise addition of 1M HCl (1 mL) and diluted with EtOAc (5 mL). The organic phase was removed and the aqueous phase back extracted with EtOAc (3×5 mL). The combined organic phases were washed with brine (3 mL), dried over $MgSO_4$, filtered and concentrated in vacuo (231.7 mg). The resultant residue was purified via column chromatography to afford the desired sulfonyl urea's as a crude inseparable mixture.

N,N'-(3α,7α-Dihydroxyl-4β-fluoro-6α-ethyl-24-nor-5β-cholan-23-yl)-4-(trifluoromethoxy)benzene sulfonyl urea (Compound 12) and N,N'-(3α,7α-dihydroxyl-4β-fluoro-6α-ethyl-24-nor-5β-cholan-23-yl)-p-methoxybenzene sulfonyl urea (Compound 13)

Compounds 12 and 13 were prepared according to General Procedure 3 above by reaction of the crude isocyanate product with 4-(trifluoromethoxy)benzene sulfonamide and 4-(methoxy)benzene sulfonamide respectively.

In order obtain pure products, the crude Compounds 12 and 13 were converted to protected materials (Intermediates 12 and 13) which were purified and then deprotected to regenerate Compounds 12 and 13. This process is described below.

N,N'-(3α,7α-Di-O-tert-butyldimethylsilyl-4β-fluoro-6α-ethyl-24-nor-5β-cholan-23-yl)-4-(trifluoromethoxy)benzene sulfonyl urea (Intermediate 12)

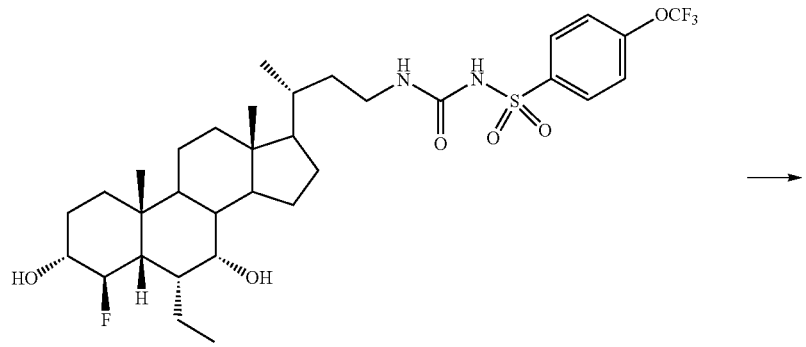

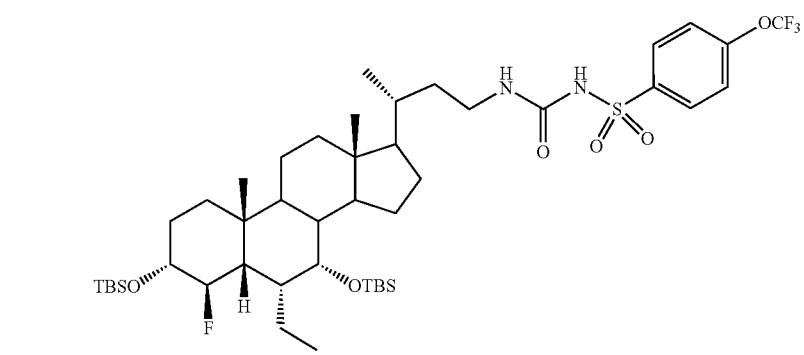

N,N'-(3α, 7α-dihydroxyl-4β-fluoro-6α-ethyl-24-nor-5β-cholan-23-yl)-4-(trifluoromethoxy)benzene sulfonyl urea (24.3 mg, 0.036 mmol) was dissolved in dry DCM (1 mL) and cooled to 0° C. with stirring, under argon. 2,6-lutidine (0.04 mL, 0.36 mmol) was charged followed by the drop-wise addition of TBMDS-OTf (0.02 mL, 0.108 mmol). The reaction was warmed to RT and stirred for 1.5 h then cooled to 0° C. and quenched by the drop-wise addition of 10% citric acid (1 mL). The phases were separated and the aqueous phase was extracted with DCM (3×1 mL). The combined extracts were washed with 10% citric acid (1 mL), aq. NaHCO₃ (1 mL) and water (1 mL), dried over MgSO₄, filtered and concentrated in vacuo to a yellow oil. The crude material was purified by column chromatography (SiO₂, 0-50% EtOAc in heptane) to afford the title compound as a clear oil (9.4 mg, 33%).

N,N'-(3α,7α-Dihydroxyl-4β-fluoro-6α-ethyl-24-nor-5β-cholan-23-yl)-4-(trifluoromethoxy)benzene sulfonyl urea (Compound 12)

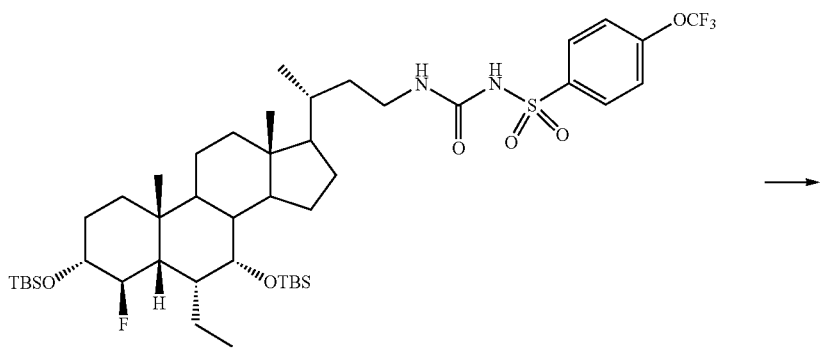

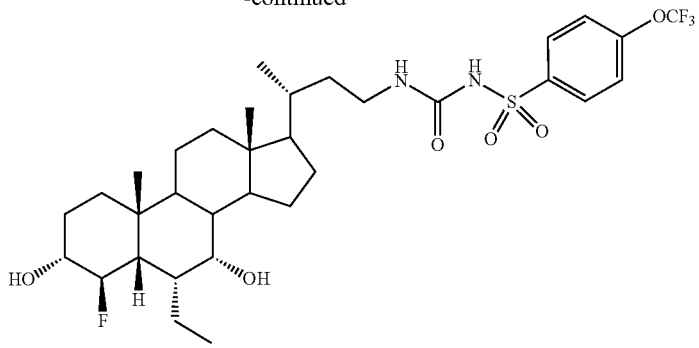

N,N'-(3α,7α-di-O-tert-butyldimethylsilyl-4β-fluoro-6α-ethyl-24-nor-5β-cholan-23-yl)-4-(trifluoromethoxy)benzene sulfonyl urea (9.4 mg) was dissolved in dry THF (1 mL) with stirring under argon. 1 M TBAF in THF (31 µL, 0.03 mmol) was charged and the reaction was stirred at RT for 6 days. The crude solution was dry loaded onto silica gel and purified by column chromatography (SiO$_2$, 50-100% EtOAc in heptane) to afford the title compound (1 mg).

N,N'-(3α,7α-Di-O-tert-butyldimethylsilyl-4β-fluoro-6α-ethyl-24-nor-5β-cholan-23-yl)-p-methoxybenzene sulfonyl urea (Intermediate 13)

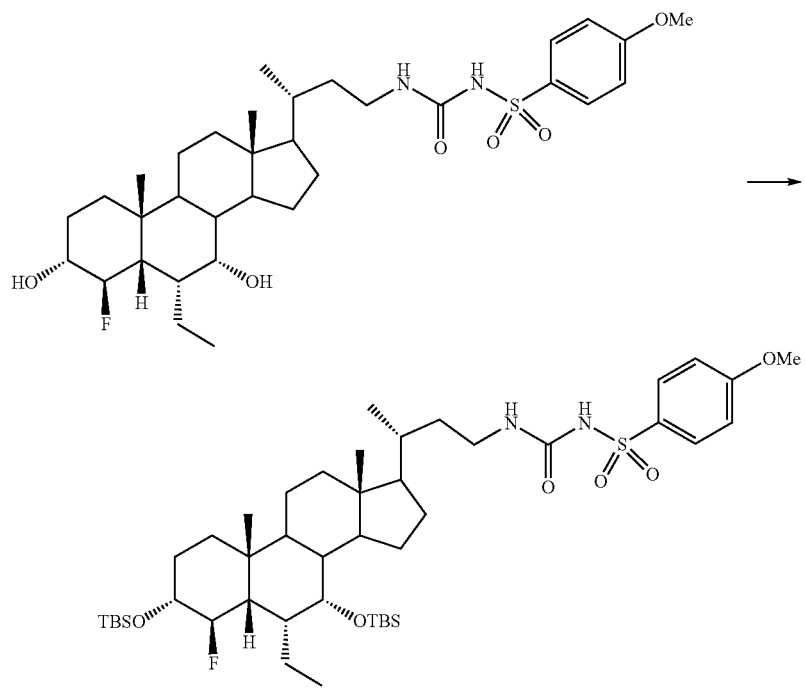

N,N'-(3α, 7α-dihydroxyl-4β-fluoro-6α-ethyl-24-nor-5β-cholan-23-yl)-p-methoxybenzene sulfonyl urea (26.1 mg, 0.042 mmol) was dissolved in dry DCM (1 mL) and cooled to 0° C. with stirring, under argon. 2,6-lutidine (0.05 mL, 0.419 mmol) was charged followed by the drop-wise addition of TBMDS-OTf (0.03 mL, 0.126 mmol). The reaction was warmed to RT and stirred for 16 h then cooled to 0° C. and quenched by the drop-wise addition of 10% citric acid (1 mL). The phases were separated and the aqueous phase was extracted with DCM (3×1 mL). The combined extracts were washed with 10% citric acid (1 mL), aq. NaHCO$_3$ (1 mL) and water (1 mL), dried over MgSO$_4$, filtered and concentrated in vacuo to a yellow oil (28.1 mg). The crude material was purified by column chromatography (SiO$_2$, 0-80% MeOH in DCM) then re-purified by column chromatography (SiO$_2$, 0-50% acetone in toluene) to afford the title compound (7.8 mg).

N,N'-(3α,7α-Dihydroxyl-4β-fluoro-6α-ethyl-24-nor-5β-cholan-23-yl)-p-methoxybenzene sulfonyl urea (Compound 13)

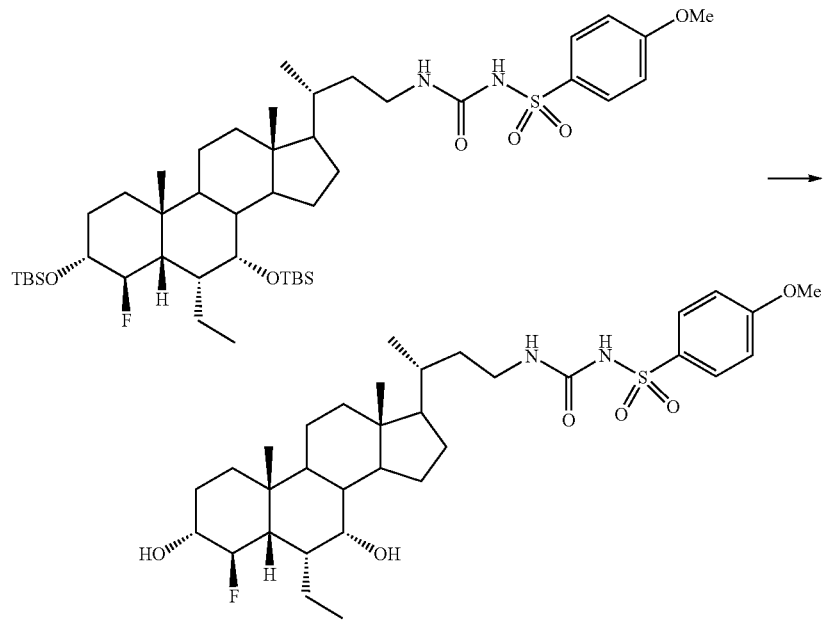

N,N'-(3α,7α-di-O-tert-butyldimethylsilyl-4β-fluoro-6α-ethyl-24-nor-5β-cholan-23-yl)-p-methoxybenzene sulfonyl urea (7.8 mg) was dissolved in dry THF (1 mL) with stirring under argon. 1 M TBAF in THF (28 µL, 0.03 mmol) was charged and the reaction was stirred at RT for 17 h. The crude solution was dry loaded onto silica gel and purified by column chromatography (SiO$_2$, 0-80% acetone in toluene) to afford the title compound (3.4 mg, 59.6%).

$^1$H NMR (400 MHz, CDCl$_3$): δ 7.97-7.81 (2H, m), 7.11-7.02 (2H, m), 5.30 (1H, ddd, J=49.6, 10.3, 8.9 Hz), 3.88 (3H, s), 3.76 (1H, br. s), 3.42 (1H, m), 3.15 (1H, m), 3.06 (1H, m), 1.99-0.96 (26H, m), 0.95-0.80 (6H, m), 0.64 (3H, s) ppm.

Example 3—Synthesis of Compounds with Sulfonamide-Substituted Side Chains

The methods below are illustrated for 4β-fluoro derivatives but could also be used for 2β-fluorinated, 4,4-difluorinated or 2,4-difluoroinated compounds. Steps A and B are as for Example 2.

C. 6α-Ethyl-4β-fluoro-7α-trimethylsiloxy-3α-hydroxyl-5β-cholanic Acid

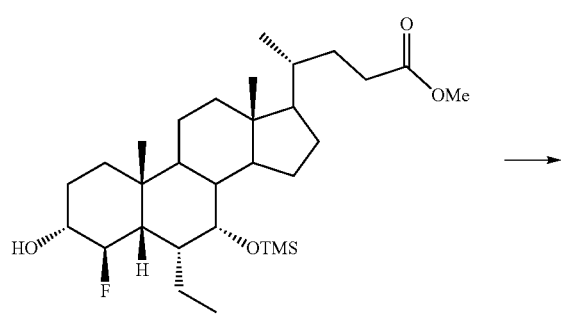

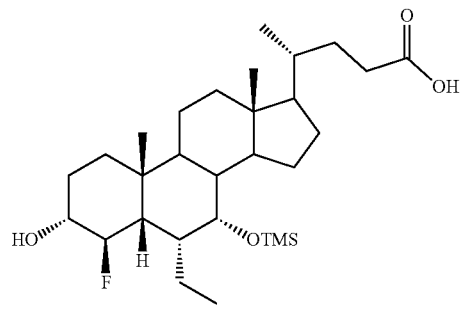

Methyl 6α-ethyl-4β-fluoro-7α-trimethylsiloxy-3α-hydroxyl-5β-cholan-24-oate from Step B (162.3 mg) was dissolved in IPA (1.6 mL) with stirring. 0.5 M NaOH (1.6 mL) was charged and the reaction was stirred at RT for 16 h. The reaction mixture was concentrated under reduced pressure to half the volume then water (5 mL) was charged and the solution was neutralised by the addition of 2 M H$_2$SO$_4$ and diluted with EtOAc (10 mL). The mixture was acidified to pH 1 with 2 M H$_2$SO$_4$, the phases were separated and the aqueous phase was extracted with EtOAc (10 mL). The combined extracts were washed with water (3 mL) and brine (5 mL), dried over MgSO$_4$, filtered and concentrated in vacuo to afford a white foam (151.1 mg). The crude material was purified by column chromatography (SiO$_2$, 0-80% EtOAc in heptane) to afford the title compound as a clear oil (164.1 mg).

General Procedure 4 for Formation of the Acyl Sulfonamide Side Chain

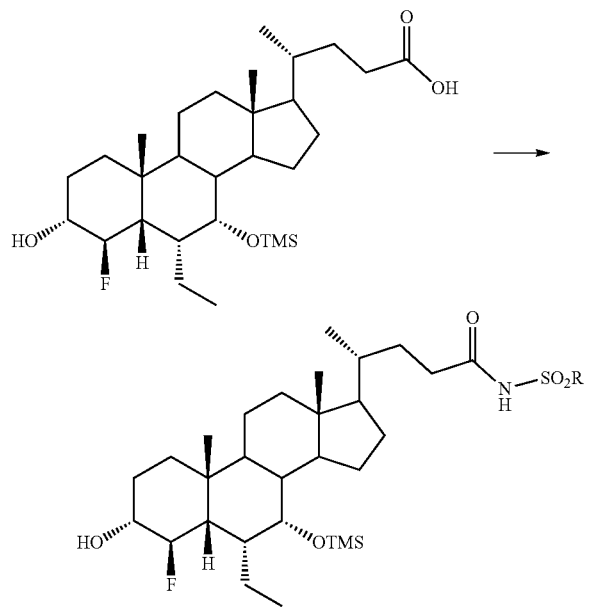

6α-ethyl-4β-fluoro-7α-trimethylsiloxy-3α-hydroxyl-5β-cholanic acid (50 mg, 0.11 mmol) was dissolved in dry DCM (2 mL). EDCI (43.7 mg, 0.23 mmol) and DMAP (27.8 mg, 0.23 mmol) followed by the appropriate sulfonamide (3 equivalents). Following an overnight stir at RT water (5 mL) was charged, the phases were separated and the aqueous phase was extracted with DCM (2×5 mL). The combined extracts were washed with 1 M HCl (2 mL) and brine (2 mL), dried over MgSO₄, filtered and concentrated in vacuo to afford the crude material as an off white solid.

N-(3α,7α-Dihydroxyl-4β-fluoro-6α-ethyl-5β-cholan-24-oyl)-p-trifluoromethoxy benzene sulfonamide (Compound 14)

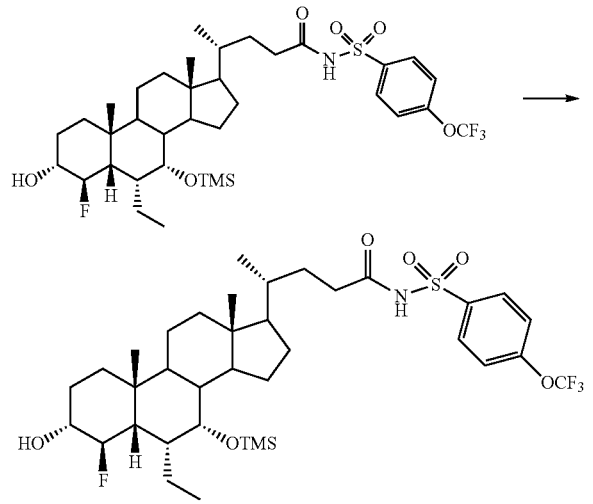

Crude N-(6α-ethyl-4β-fluoro-7α-trimethylsiloxy-3α-hydroxyl-5β-cholan-24-oyl)-trifluoromethoxy benzene sulfonamide (81.6 mg), obtained according to General Procedure 4 using trifluoromethoxy benzene sulfonamide was dissolved in dry THF (5 mL) with stirring under argon. 1 M TBAF in THF (0.48 mL, 0.48 mmol) was charged and the reaction was stirred at RT for 17.5 h. The crude solution was dry loaded onto silica gel and purified by column chromatography (SiO₂, 0-100% EtOAc in heptane). Fractions containing the desired product were combined, concentrated in vacuo, dissolved in EtOAc (5 mL) and washed with 2 M HCl (5 mL). The aqueous phase was extracted with EtOAc (2×5 mL) and the combined extracts were dried over MgSO₄, filtered and concentrated in vacuo to a white solid, which was purified by column chromatography (SiO₂, 0-25% acetone in toluene) to afford the title compound as a clear residue (4.9 mg).

$^1$H NMR (400 MHz, CDCl₃): δ 8.21-8.10 (2H, m), 7.38-7.36 (2H, dd, J=8.9, 0.8 Hz), 5.31 (1H, ddd, J=49.8, 10.4, 9.0 Hz), 3.82 (1H, br. s), 3.56 (1H, m), 2.31 (1H, ddd, J=15.6, 10.1, 5.0 Hz), 2.17 (1H, m), 1.92-1.07 (23H, m), 0.97 (3H, s), 0.93 (3H, t, J=6.9 Hz), 0.86 (3H, d, J=6.4 Hz), 0.62 (3H, s) ppm.

N-(3α,7α-Dihydroxyl-4β-fluoro-6α-ethyl-5β-cholan-24-oyl)-p-fluorobenzene sulfonamide (Compound 15)

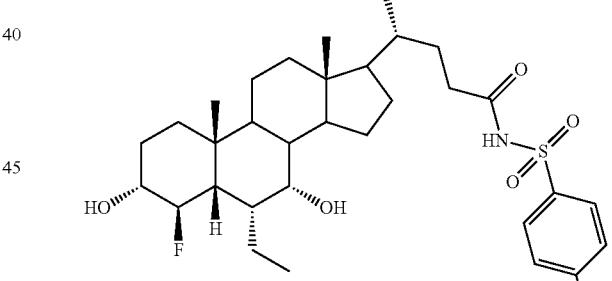

This was prepared by an analogous route to that used for Compound 14 above.

$^1$H NMR (400 MHz, CDCl₃) δ 8.11 (m, 2H), 7.23 (m, 2H), 5.31 (ddd, J=49.9, 10.3, 9.1 Hz, 1H), 3.81 (br s, 1H), 3.57 (dddd, J=13.8, 11.6, 8.6, 5.1 Hz, 1H), 2.29 (ddd, J=15.4, 10.0, 5.3 Hz, 1H), 2.17 (ddd, J=15.7, 9.2, 6.4 Hz, 1H), 1.90 (dt, J=12.3, 2.9 Hz, 1H), 1.87-1.57 (m, 9H), 1.53-1.29 (m, 8H), 1.24-1.08 (m, 7H), 0.97 (s, 3H), 0.93 (t, J=7.0 Hz, 3H), 0.86 (d, J=6.4 Hz, 3H), 0.61 (s, 3H) ppm;

$^{19}$F NMR (376 MHz, CDCl₃) −103.1 (br s, 1F), −188.8 (br s, 1F) ppm;

$^{19}$F {1H} NMR (376 MHz, CDCl₃) −103.1 (br s, 1F), −188.8 (br s, 1F) ppm.

N-(3α,7α-Dihydroxyl-4β-fluoro-6α-ethyl-5β-cholan-24-oyl)-m-fluorophenyl sulfonamide (Compound 16)

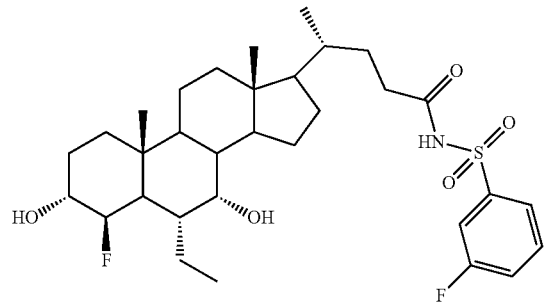 [SMILES: CC[C@@H]1C2[C@@H](F)[C@H](O)CC[C@]2(C)C2CC[C@@]3(C)C(CCC3[C@H](C)CCC(=O)NS(=O)(=O)c3cccc(F)c3)C2[C@@H]1O]

This was prepared by an analogous route to that used for Compound 14 above.

$^1$H NMR (400 MHz, CDCl$_3$) 8.39 (1H, br s), 7.89 (1H, br d, J=7.8 Hz), 7.78 (1H, br d, J=7.7 Hz), 7.55 (1H, td, J=8.1, 5.4 Hz), 7.36 (1H, td, J=8.3, 1.3 Hz), 5.31 (1H, dt, J=50.0, 9.8 Hz), 3.82 (1H, br s), 3.56 (1H, dddd, J=14.2, 11.0, 8.7, 5.1 Hz), 2.31 (1H, ddd, J=15.0, 9.9, 5.1 Hz), 2.18 (1H, ddd, J=15.3, 9.5, 7.2 Hz), 1.99-1.03 (25H, m), 0.97 (3H, s), 0.94 (3H, t, J=6.6 Hz), 0.87 (3H, d, J=8.1 Hz), 0.62 (3H, s) ppm.

$^{19}$F NMR (376 MHz, CDCl$_3$)–109.52 (1F, br d, J=5.2 Hz), –189.0 (1F, dt, J=50.1, 13.9 Hz) ppm.

$^{19}$F {1H} NMR (376 MHz, CDCl$_3$)–109.52 (1F, s), –189.00 (1F, s) ppm.

N-(3α,7α-Dihydroxyl-4β-fluoro-6α-ethyl-5β-cholan-24-oyl)-o-fluorophenyl sulfonamide (Compound 17)

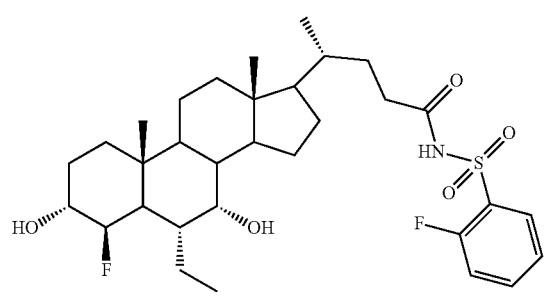 [SMILES: CC[C@@H]1C2[C@@H](F)[C@H](O)CC[C@]2(C)C2CC[C@@]3(C)C(CCC3[C@H](C)CCC(=O)NS(=O)(=O)c3ccccc3F)C2[C@@H]1O]

This was prepared by an analogous route to that used for Compound 14 above.

$^1$H NMR (400 MHz, CDCl$_3$) δ 9.06 (1H, br s), 8.10 (1H, td, J=7.5, 1.5 Hz), 7.65 (1H, m), 7.35 (1H, t, J=7.6 Hz), 7.22 (1H, t, J=9.2 Hz), 5.31 (1H, dt, J=50.1, 9.5 Hz), 3.81 (1H, br s), 3.57 (1H, dddd, J=14.1, 11.3, 8.6, 5.1 Hz), 2.34 (1H, ddd, J=15.4, 10.0, 5.0 Hz), 2.21 (1H, ddd, J=15.9, 9.3, 6.6 Hz), 2.08-1.02 (25H, m), 0.96 (3H, s), 0.92 (3H, br t, J=6.9 Hz), 0.86 (3H, d, J=6.2 Hz), 0.61 (3H, s) ppm;

$^{19}$F NMR (376 MHz, CDCl$_3$)–110.0 (1F, br s), –189.1 (1F, d, J=46.8 Hz) ppm.

$^{19}$F {1H} NMR (376 MHz, CDCl$_3$)–109.8 (1F, s), –188.9 (1F, s) ppm.

N-(3α,7α-Dihydroxyl-4β-fluoro-6α-ethyl-5β-cholan-24-oyl)-4-trifluoromethylphenyl sulfonamide (Compound 18)

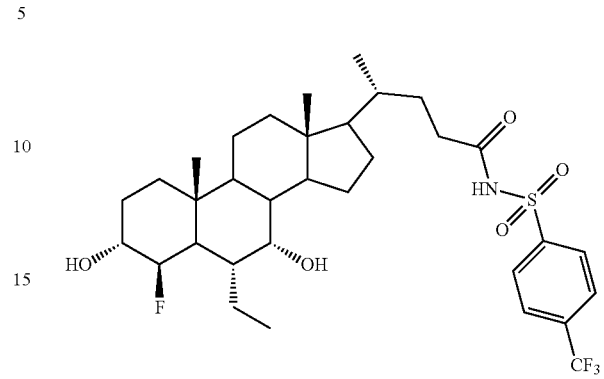

This was prepared by an analogous route to that used for Compound 14 above.

$^1$H NMR (400 MHz, CDCl$_3$) 8.22 (2H, d, J=8.3 Hz), 8.00 (1H, br s) 7.83 (2H, d, J=8.4 Hz), 5.30 (1H, dtd, J=50.1, 10.2, 1.6 Hz), 3.81 (1H, br s), 3.56 (1H, dddd, J=13.9, 12.0, 8.6, 5.0 Hz), 2.31 (1H, ddd, J=15.8, 10.3, 5.1 Hz), 2.17 (1H, ddd, J=15.8, 10.0, 6.6 Hz), 1.94-1.05 (25H, m), 0.97 (3H, s), 0.93 (3H, t, J=5.8 Hz), 0.87 (3H, d, J=6.1 Hz), 0.61 (3H, s) ppm.

$^{19}$F NMR (376 MHz, CDCl$_3$)–63.5 (3F, br s), –189.2 (1F, br d, J=48.6 Hz) ppm.

$^{19}$F {1H} NMR (376 MHz, CDCl$_3$)–63.3 (3F, s), –189.0 (1F, s) ppm.

N-(3α,7α-Dihydroxyl-4β-fluoro-6α-ethyl-5β-cholan-24-oyl)-3-trifluoromethylphenyl sulfonamide (Compound 19)

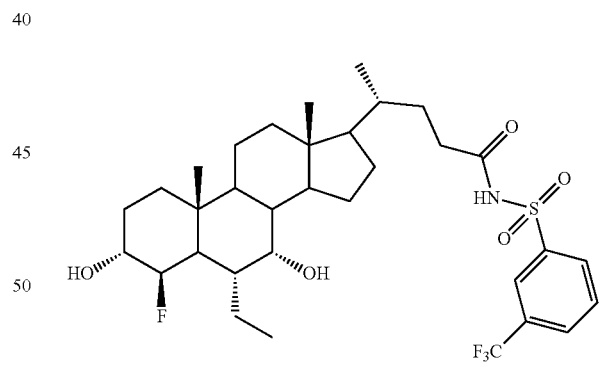

This was prepared by an analogous route to that used for Compound 14 above.

$^1$H NMR (400 MHz, CDCl$_3$) 8.32 (2H, m), 8.22 (1H, br s), 7.92 (1H, br d, J=7.8 Hz), 7.72 (1H, t, J=7.9 Hz), 5.30 (1H, dtd, J=49.5, 9.3, 1.2 Hz), 3.81 (1H, br s), 3.54 (1H, m), 2.31 (1H, ddd, J=15.6, 10.1, 5.1 Hz), 2.18 (1H, ddd, J=15.9, 9.2, 6.4 Hz), 1.95-1.04 (25H, m), 0.97 (3H, s), 0.93 (3H, t, J=6.9 Hz), 0.86 (3H, d, J=6.2 Hz), 0.61 (3H, s) ppm.

$^{19}$F NMR (376 MHz, CDCl$_3$)–63.02 (3F, s), –189.11 (1F, br d, J=48.6 Hz) ppm.

$^{19}$F {1H} NMR (376 MHz, CDCl$_3$)–63.02 (3F, s, CF$_3$), –189.10 (1F, s) ppm.

N-(3α,7α-Dihydroxyl-4β-fluoro-6α-ethyl-5β-cholan-24-oyl)-2-trifluoromethylphenyl sulfonamide (Compound 20)

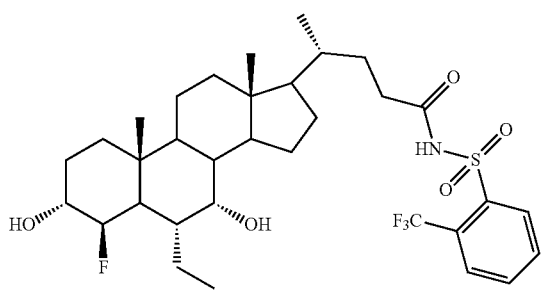 [SMILES: CC[C@@H]1C2[C@@H](F)[C@H](O)CC[C@]2(C)C2CC[C@@]3(C)C(CCC3[C@H](C)CCC(=O)NS(=O)(=O)c3ccccc3C(F)(F)F)C2[C@@H]1O]

This was prepared by an analogous route to that used for Compound 14 above.

$^1$H NMR (400 MHz, CDCl$_3$) 8.53 (1H, m), 8.09 (1H, br s), 7.90 (1H, m), 7.79 (2H, m), 5.3 (1H, dtd, J=50.0, 9.8, 1.7 Hz), 3.81 (1H, br s), 3.55 (1H, dddd, J=14.2, 11.7, 8.8, 5.0 Hz), 2.31 (1H, ddd, J=15.3, 9.7, 4.8 Hz), 2.17 (1H, m), 1.91 (1H, m), 1.87-1.05 (24H, m), 0.97 (3H, s), 0.93 (3H, t, J=6.9 Hz), 0.86 (3H, d, J=6.2 Hz), 0.61 (3H, s) ppm.

$^{19}$F NMR (376 MHz, CDCl$_3$)–63.02 (3F, s), –189.11 (1F, br d, J=48.6 Hz) ppm.

$^{19}$F {1H} NMR (376 MHz, CDCl$_3$)–63.02 (3F, s), –189.10 (1F, s) ppm.

N-(3α,7α-Dihydroxyl-4β-fluoro-6α-ethyl-5β-cholan-24-oyl)-cyclopropyl sulfonamide (Comparative Compound B)

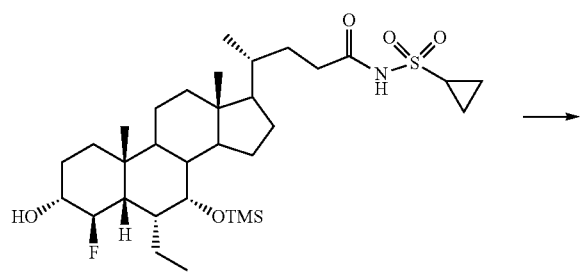

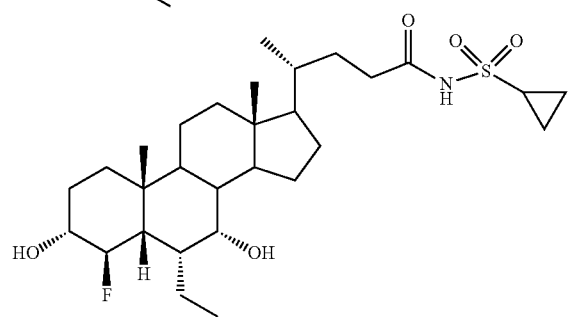

N-(3α-hydroxyl-4β-fluoro-6α-ethyl-7α-trimethylsiloxy-5β-cholan-24-yl)-cyclopropyl sulfonamide (50 mg) was dissolved in dry THF with stirring under argon. 1 M TBAF in THF (0.3 mL, 0.3 mmol) was charged and the reaction was stirred at RT for 23 h. The reaction was diluted with EtOAc (20 mL) and washed with water (10 mL) and 10% aq. NaCl. The crude solution was dry loaded onto silica gel and purified by column chromatography (SiO$_2$, 0-50% acetone in toluene) to afford the title compound (5.4 mg).

R$_f$ 0.65 (EtOAc/heptane, 50:50).

$^1$H NMR (400 MHz, CDCl$_3$): δ 5.31 (1H, ddd, J=49.8, 10.7, 8.9 Hz), 3.83 (1H, br. s), 3.55 (1H, m), 2.95 (1H, tt, J=8.1, 4.8 Hz), 2.39 (1H, m), 2.25 (1H, m), 2.01-1.07 (27H, m), 0.98 (3H, s), 0.95 (3H, d, J=6.5 Hz), 0.94 (3H, t, J=7.1 Hz), 0.67 (3H, s) ppm.

N-(3α,7α-Dihydroxyl-4β-fluoro-6α-ethyl-5β-cholan-24-oyl)-methyl sulfonamide (Comparative Compound C)

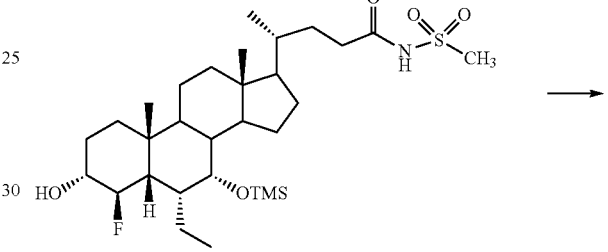

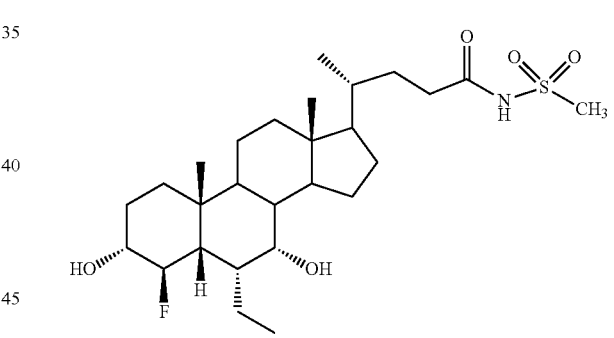

N-(3α-hydroxyl-4β-fluoro-6α-ethyl-7α-trimethylsiloxy-5β-cholan-24-yl)-methyl sulfonamide (50 mg) was dissolved in dry THF with stirring under argon. 1 M TBAF in THF (0.3 mL, 0.3 mmol) was charged and the reaction was stirred at RT for 16 h. The reaction was diluted with EtOAc (5 mL) and washed with brine (3 mL). The crude solution was dry loaded onto silica gel and purified by column chromatography (SiO$_2$, 0-50% acetone in toluene). Fractions containing the desired product were combined, concentrated under reduced pressure, dissolved in CDCl$_3$, washed with 2 M HCl and water, filtered through PTFE filter pad and concentrated in vacuo to afford the title compound (7.1 mg).

$^1$H NMR (400 MHz, CDCl$_3$): δ 5.30 (1H, ddd, J=49.8, 10.4, 8.8 Hz), 3.83 (1H, br. s), 3.56 (1H, m), 3.30 (3H, s), 2.39 (1H, ddd, J=15.6, 10.3, 5.1 Hz), 2.25 (1H, m), 2.00-1.08 (23H, m), 0.97 (3H, s), 0.94 (3H, d, J=6.5 Hz), 0.93 (3H, t, J=6.8 Hz), 0.67 (3H, s) ppm.

Example 4—Synthesis of 4,4-difluoro-3α,7α-dihydroxyl-6α-ethyl-5β-cholanic Acid Analogues with Sulfonylurea and Acyl Sulfonamide Side Chains A. Methyl 6α-ethyl-4,4-difluoro-7α-hydroxyl-3-oxo-5β-cholan-24-oate

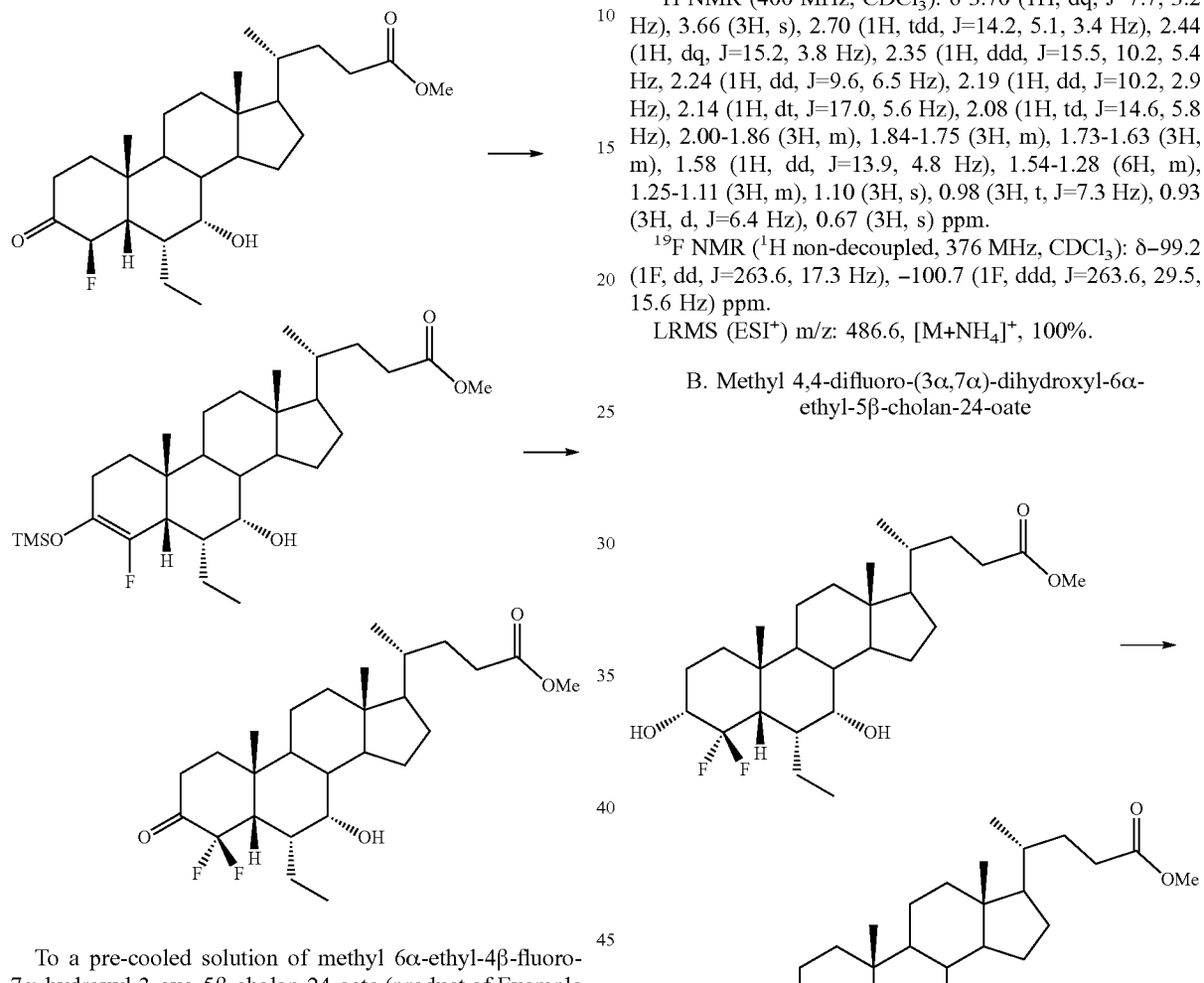

To a pre-cooled solution of methyl 6α-ethyl-4β-fluoro-7α-hydroxyl-3-oxo-5β-cholan-24-oate (product of Example 1C; 7.30 g, 16.0 mmol) in dry THF (300 mL) at −78° C. was added LDA in hexanes (21.1 mL, 21.1 mmol, ~1.3 equiv.) dropwise over 0.25 h under argon. After addition, trimethylsilylchloride (2.70 mL, 21.1 mmol, ~1.3 equiv.) was added as a solution in dry THF (150 mL) and stirred for 1 h. Upon completion, the reaction was quenched via the dropwise addition of saturated NaHCO$_3$ solution (300 mL) and warmed to RT for 0.25 h. The organic phase was removed and the aqueous phase back extracted with dichloromethane (2×150 mL). Organic phases were combined, washed with brine (300 mL), dried over MgSO$_4$, filtered and concentrated in vacuo to afford the crude material as a yellow residue (3% methyl 6α-ethyl-4β-fluoro-7α-hydroxyl-3-oxo-5β-cholan-24-oate contamination by $^{19}$F NMR). The resultant residue was used for the next reaction without further purification.

$^{19}$F NMR ($^1$H non-decoupled, 376 MHz): δ−135.2 (1F, s);

To a stirred solution of the resultant crude material in MeCN (360 mL) was added SELECTFLUOR® (11.4 g, 32.0 mmol, ~2.0 equiv.) and stirred for 16 h. Upon completion the reaction mixture was concentrated in vacuo. The residue was dissolved in dichloromethane (500 mL) and H$_2$O (500 mL). The organic phase was removed and the aqueous phase back extracted with dichloromethane (2×250 mL). Organic phases were combined, washed with brine (250 mL), dried over MgSO$_4$, filtered and concentrated in vacuo to afford the crude material as a yellow residue. The resultant residue was used for the next reaction without purification.

$^1$H NMR (400 MHz, CDCl$_3$): δ 3.70 (1H, dq, J=7.7, 3.2 Hz), 3.66 (3H, s), 2.70 (1H, tdd, J=14.2, 5.1, 3.4 Hz), 2.44 (1H, dq, J=15.2, 3.8 Hz), 2.35 (1H, ddd, J=15.5, 10.2, 5.4 Hz, 2.24 (1H, dd, J=9.6, 6.5 Hz), 2.19 (1H, dd, J=10.2, 2.9 Hz), 2.14 (1H, dt, J=17.0, 5.6 Hz), 2.08 (1H, td, J=14.6, 5.8 Hz), 2.00-1.86 (3H, m), 1.84-1.75 (3H, m), 1.73-1.63 (3H, m), 1.58 (1H, dd, J=13.9, 4.8 Hz), 1.54-1.28 (6H, m), 1.25-1.11 (3H, m), 1.10 (3H, s), 0.98 (3H, t, J=7.3 Hz), 0.93 (3H, d, J=6.4 Hz), 0.67 (3H, s) ppm.

$^{19}$F NMR ($^1$H non-decoupled, 376 MHz, CDCl$_3$): δ−99.2 (1F, dd, J=263.6, 17.3 Hz), −100.7 (1F, ddd, J=263.6, 29.5, 15.6 Hz) ppm.

LRMS (ESI$^+$) m/z: 486.6, [M+NH$_4$]$^+$, 100%.

B. Methyl 4,4-difluoro-(3α,7α)-dihydroxyl-6α-ethyl-5β-cholan-24-oate

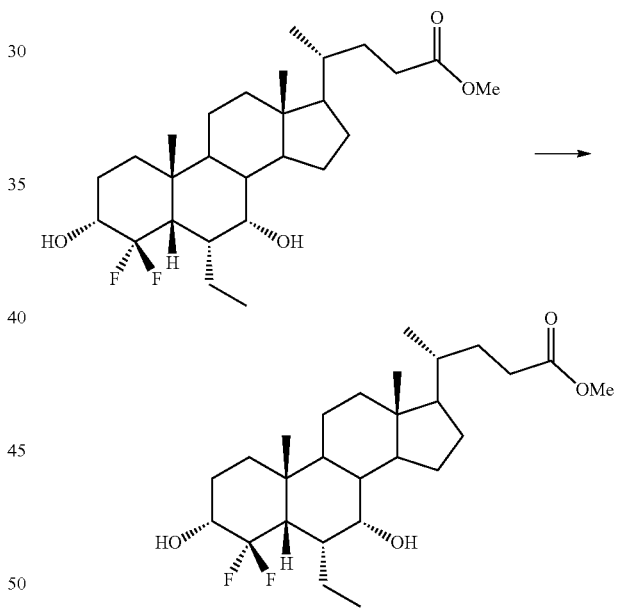

To a stirred solution of crude methyl 6α-ethyl-4,4-difluoro-7α-hydroxyl-3-oxo-5β-cholan-24-oate from Step A (7.51 g assumed, 16.0 mmol) in dry methanol (500 mL) at RT was added NaBH$_4$ (3.03 g, 80.1 mmol, ~5.0 equiv) and stirred for 72 h under argon. Upon completion the reaction was concentrated in vacuo. The residue was dissolved in dichloromethane (500 mL) and H$_2$O (500 mL). The organic phase was removed and the aqueous phase back extracted with dichloromethane (2×250 mL). Organic phases were combined, washed with brine (250 mL), dried over MgSO$_4$, filtered over SiO$_2$ and concentrated in vacuo to afford 7.63 g of crude material as a colourless residue. Purification by flash column chromatography (Biotage SNAP KP-Sil 100 g cartridge) using hexane/acetone (100/0 to 80/20) as the eluent yielded the title compound methyl 4,4-difluoro-(3α, 7α)-dihydroxyl-6α-ethyl-5β-cholan-24-oate as a colourless residue (3.09 g, 6.57 mmol, 41% over three steps).

$^1$H NMR (400 MHz, CDCl$_3$): δ 3.76-3.65 (2H, m), 3.67 (3H, s), 2.36 (1H, ddd, J=15.5, 10.3, 5.4 Hz), 2.31-2.19 (2H, m), 2.11 (1H, d, J=5.4 Hz), 2.00-1.92 (3H, m), 1.91-1.30 (16H, m), 1.22-1.10 (4H, m), 1.04 (3H, s), 0.97 (3H, t, J=7.3 Hz), 0.92 (3H, d, J=6.5 Hz), 0.65 (3H, s) ppm.

$^{19}$F NMR ($^1$H non-decoupled, 376 MHz, CDCl$_3$): δ−99.3 (1F, d, J=239.3 Hz), −111.4 (1F, dtd, J=239.3, 34.7, 22.5 Hz) ppm.

LRMS (ESI$^+$) m/z: 488.6, [M+NH$_4$]$^+$, 100%.

C. 3α, 7α-Dihydroxyl-4,4-difluoro-6α-ethyl-5β-cholanic Acid

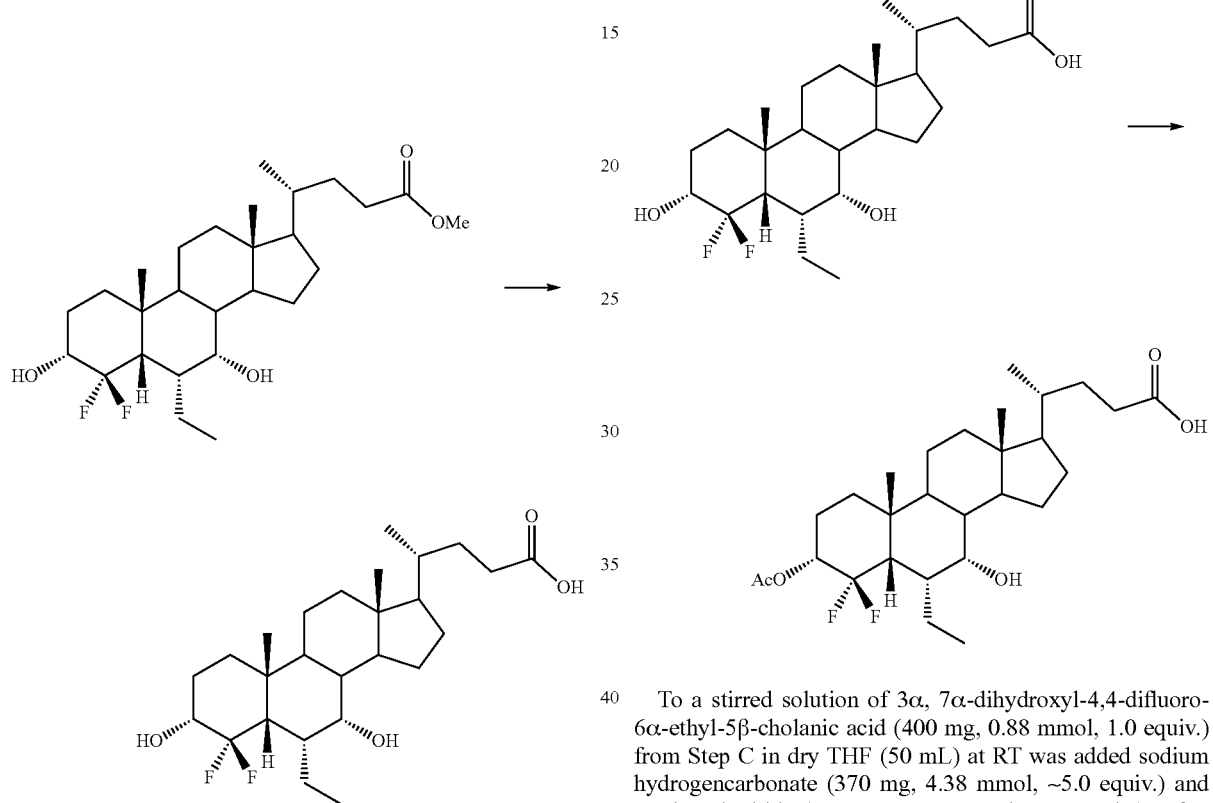

To a stirred solution of methyl 4,4-difluoro-(3α,7α)-dihydroxyl-6α-ethyl-5β-cholan-24-oate (1.77 g, 3.75 mmol, 1.0 equiv.) from Step B in a solution of 1,4-dioxane (95 mL) and water (35 mL) at RT was added concentrated (37%) hydrochloric acid (11 mL, 9:3:1 ratio). After 1 h at reflux, the reaction mixture was cooled to RT and neutralised with saturated NaHCO$_3$ solution (50 mL). The organic phase was removed and the aqueous phase back extracted with dichloromethane (3×50 mL). Organic phases were combined, washed with brine (200 mL), dried over MgSO$_4$, filtered and concentrated in vacuo to afford 1.84 g of crude material as a brown oil. Purification by flash column chromatography (Biotage SNAP KP-Sil 50 g cartridge) using hexane/acetone (100/0 to 90/10) as the eluent yielded the title compound 3α, 7α-dihydroxyl-4,4-difluoro-6α-ethyl-5β-cholanic acid as a colourless oil (1.51 g, 3.30 mmol, 88%).

$^1$H NMR (400 MHz, CDCl$_3$): δ 3.78-3.64 (2H, m), 2.39 (1H, ddd, J=15.8, 10.3, 5.3 Hz), 2.25 (1H, ddd, J=15.7, 9.6, 6.4 Hz), 1.98-1.93 (3H, m), 1.86-1.65 (7H, m), 1.60 (1H, d, J=13.0 Hz), 1.49-1.41 (5H, m), 1.40-1.29 (3H, m), 1.25-1.16 (6H, m), 1.04 (3H, s), 0.96 (3H, t, J=7.3 Hz), 0.93 (3H, d, J=6.4 Hz), 0.65 (3H, s) ppm.

$^{19}$F NMR ($^1$H non-decoupled, 376 MHz, CDCl$_3$): δ−99.1 (1F, d, J=239.3 Hz), −111.1 (1F, dtd, J=241.0, 38.2, 19.1 Hz) ppm.

LRMS (ESI$^+$) m/z: 474.6, [M+NH$_4$]$^+$, 100%.

D. 3α-Acetoxy-4,4-difluoro-6α-ethyl-7α-hydroxyl-5β-cholanic Acid

To a stirred solution of 3α, 7α-dihydroxyl-4,4-difluoro-6α-ethyl-5β-cholanic acid (400 mg, 0.88 mmol, 1.0 equiv.) from Step C in dry THF (50 mL) at RT was added sodium hydrogencarbonate (370 mg, 4.38 mmol, ~5.0 equiv.) and acetic anhydride (0.41 mL, 4.38 mmol, ~5.0 equiv.). After 16 h at 70° C., the reaction mixture was cooled to RT and quenched by the slow addition of H$_2$O (50 mL). The organic phase was removed and the aqueous phase back extracted with EtOAc (2×50 mL). Organic phases were combined, washed with saturated NaHCO$_3$ solution (100 mL), dried over MgSO$_4$, filtered and concentrated in vacuo to afford 462 mg of crude material as a yellow oil. Purification by flash column chromatography (Biotage SNAP KP-Sil Ultra 25 g cartridge) using hexane/acetone (100/0 to 80/20) as the eluent yielded the title compound 3α-Acetoxy-4,4-difluoro-6α-ethyl-7α-hydroxyl-5β-cholanic acid as a colourless oil (270 mg, 0.54 mmol, 62%).

$^1$H NMR (400 MHz, CDCl$_3$): δ 4.97 (1H, ddd, J=27.5, 10.2, 6.0 Hz), 3.67 (1H, s), 2.54-2.33 (2H, m), 2.30-2.26 (1H, m), 2.24-2.18 (1H, m), 2.13 (3H, s), 2.02-1.79 (6H, m), 1.77-1.62 (3H, m), 1.56-1.42 (6H, m), 1.41-1.21 (5H, m), 1.20-1.13 (3H, m), 1.05 (3H, s), 0.95 (3H, t, J=7.3 Hz), 0.94 (3H, d, J=6.5 Hz), 0.66 (3H, s) ppm.

$^{19}$F NMR ($^1$H non-decoupled, 376 MHz, CDCl$_3$): δ−98.2 (1F, d, J=244.5 Hz), −107.1 (1F, ddd, J=242.8, 36.4, 22.5 Hz) ppm.

LRMS (ESI$^+$) m/z: 516.5, [M+NH$_4$]$^+$, 100%.

E. 3α-Acetoxy-4,4-difluoro-6α-ethyl-7α-hydroxyl-5β-cholan-24-oyl-azide

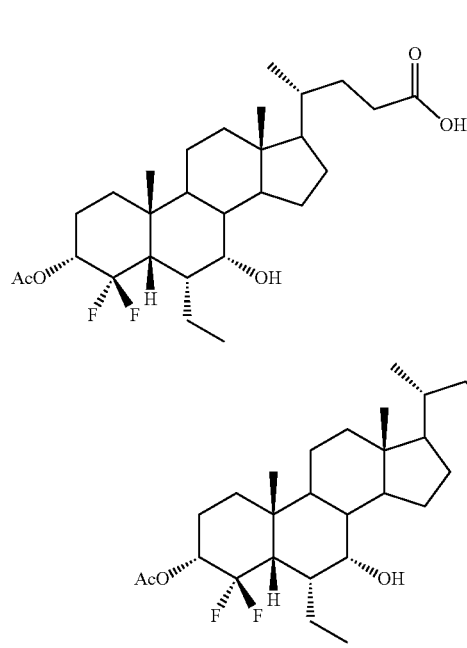

To a pre-cooled solution of 3α-acetoxy-4,4-difluoro-6α-ethyl-7α-hydroxyl-5β-cholanic acid (240 mg, 0.48 mmol, 1.0 equiv.) from Step D in dry THF (5.3 mL) at 0° C. was added triethylamine (0.14 mL, 0.96 mmol, ~2.0 equiv.) and diphenylphosphorylazide (0.16 mL, 0.72 mmol, ~1.5 equiv.). After 3 h the reaction mixture was quenched by the slow addition of brine (10 mL). The organic phase was removed and the aqueous phase back extracted with dichloromethane (3×20 mL). Organic phases were combined, dried over MgSO$_4$, filtered and concentrated in vacuo at 0° C. to afford the crude material as a pale-yellow oil. The resulting oil was used for the next reaction further purification.

$^1$H NMR—characteristic peaks (400 MHz, CDCl$_3$): δ 4.94-4.83 (1H, m), 3.59 (1H, s), 2.30 (1H, ddd, J=15.7, 10.0, 5.4 Hz), 2.04 (3H, s), 0.97 (3H, s), 0.87 (3H, t, J=7.3 Hz), 0.84 (3H, d, J=6.4 Hz), 0.57 (3H, s) ppm.

$^{19}$F NMR ($^1$H non-decoupled, 376 MHz, CDCl$_3$): δ−98.2 (1F, d, J=242.8 Hz), −107.2 (1F, dtd, J=242.8, 33.0, 26.0 Hz) ppm.

F. 3α-Acetoxy-4,4-difluoro-6α-ethyl-7α-hydroxyl-24-nor-5β-cholan-23-yl isocyanate

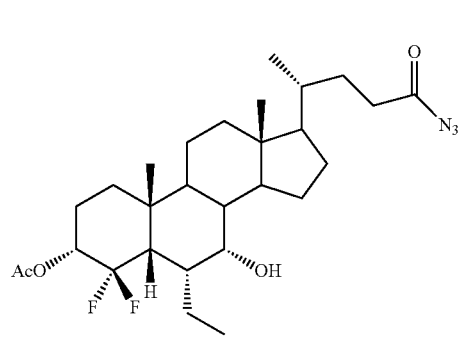

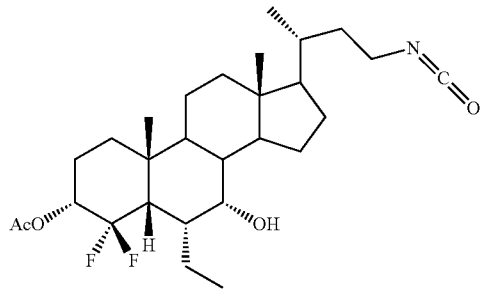

A stirred solution of crude oil 3α-acetoxy-4,4-difluoro-6α-ethyl-7α-hydroxyl-5β-cholan-24-oyl azide from Step E (252 mg assumed, 0.48 mmol) in dry toluene (7.5 mL) was heated to 125° C. under argon. After 4 h the reaction was cooled to RT. The resulting solution was used without further purification.

$^1$H NMR—characteristic peaks (400 MHz, CDCl$_3$): δ 4.89 (1H, ddd, J=27.5 10.2, 6.5 Hz), 3.59 (1H, q, J=3.2 Hz), 3.27 (1H, ddd, J=13.1, 7.8, 4.5 Hz), 3.22-3.15 (1H, m), 2.04 (3H, s), 0.97 (3H, s), 0.88 (3H, t, J=7.1 Hz), 0.86 (3H, d, J=6.4 Hz), 0.59 (3H, s) ppm.

$^{19}$F NMR ($^1$H non-decoupled, 376 MHz, CDCl$_3$): δ−98.2 (1F, d, J=242.8 Hz), −107.2 (1F, dtd, J=243.2, 37.7, 22.5 Hz) ppm.

G. N,N'-(3α-Acetoxy-4,4-difluoro-6α-ethyl-7α-hydroxyl-24-nor-5β-cholan-23-yl)-benzene sulfonyl urea

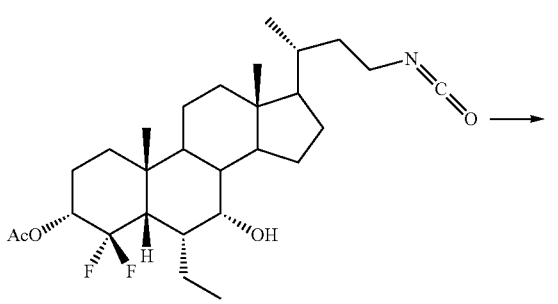

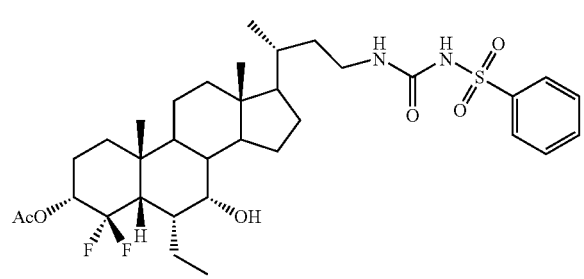

Prepared according to general procedure 1 using 113 mg of benzenesulfonamide to afford the title compound N,N'-

(3α-acetoxy-4,4-difluoro-6α-ethyl-7α-hydroxyl-24-nor-5β-cholan-23-yl)-benzene sulfonyl urea as a white residue (235 mg, 0.36 mmol, 75%).

$^1$H NMR (400 MHz, CDCl$_3$): δ 7.90 (2H, dd, J=8.4, 1.1 Hz), 7.63 (1H, tt, J=7.6, 1.1 Hz), 7.49 (2H, t, J=8.1 Hz), 6.53 (1H, s), 4.98 (1H, ddd, J=27.1, 11.3, 4.5 Hz), 3.67 (1H, s), 3.27 (1H, ddd, J=13.5, 8.9, 4.5 Hz), 3.18-3.11 (1H, m), 2.13 (3H, s), 2.02-1.79 (6H, m), 1.75-1.64 (4H, m), 1.62-1.43 (5H, m), 1.42-1.36 (1H, m), 1.28-1.10 (7H, m), 1.05 (3H, s), 0.95 (3H, t, J=7.3 Hz), 0.92 (3H, d, J=6.5 Hz), 0.63 (3H, s) ppm.

$^{19}$F NMR ($^1$H non-decoupled, 376 MHz, CDCl$_3$): δ−98.2 (1F, d, J=242.8 Hz), −107.1 (1F, dtd, J=243.2, 37.7, 22.5 Hz) ppm.

LRMS (ESI$^+$) m/z: 635.8, [M+NH$_4$]$^+$, 100%.

N,N'-(3α,7α-Dihydroxyl-4,4-difluoro-6α-ethyl-24-nor-5β-cholan-23-yl)-benzene sulfonyl urea (Compound 21)

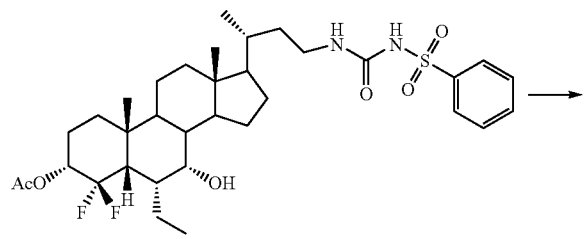

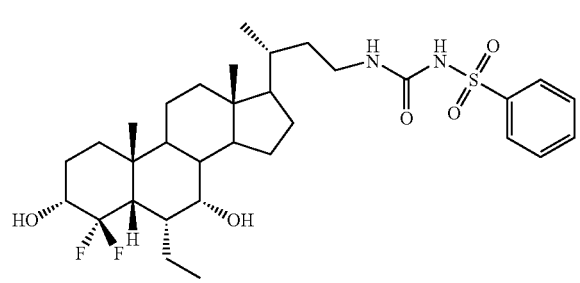

Prepared according to general procedure 2 using 210 mg of N,N-(3α-acetoxy-4,4-difluoro-6α-ethyl-7α-hydroxyl-24-nor-5β-cholan-23-yl)-benzene sulfonyl urea to afford the title compound N,N'-(3α,7α-dihydroxyl-4,4-difluoro-6α-ethyl-24-nor-5β-cholan-23-yl)-benzene sulfonyl urea as a white solid (102 mg, 0.17 mmol, 52%).

$^1$H NMR (400 MHz, CDCl$_3$): δ 8.19 (1H, s), 7.90 (2H, dt, J=7.3, 1.3 Hz), 7.65 (1H, tt, J=7.5, 1.1 Hz), 7.54 (2H, tt, J=7.3, 1.6 Hz), 6.51 (1H, t, J=5.2 Hz), 3.78-3.67 (2H, m), 3.29 (1H, ddt, J=13.9, 10.2, 5.1 Hz), 3.18 (1H, ddd, J=13.6, 8.0, 6.1 Hz), 2.30 (1H, dd, J=31.4, 11.0 Hz), 1.99-1.94 (3H, m), 1.88-1.57 (9H, m), 1.52-1.37 (5H, m), 1.23-1.11 (7H, m), 1.04 (3H, s), 0.97 (3H, t, J=7.3 Hz), 0.93 (3H, d, J=6.5 Hz), 0.64 (3H, s) ppm.

$^{19}$F NMR ($^1$H non-decoupled, 376 MHz, CDCl$_3$): δ−99.3 (1F, d, J=239.3 Hz), −111.3 (1F, dtd, J=239.3 Hz) ppm.

LRMS (ESI$^+$) m/z: 593.6, [M+NH$_4$]$^+$, 100%.

N-(3α,7α-Dihydroxyl-4,4-difluoro-6α-ethyl-5β-cholan-24-oyl)-benzene sulfonamide (Compound 22)

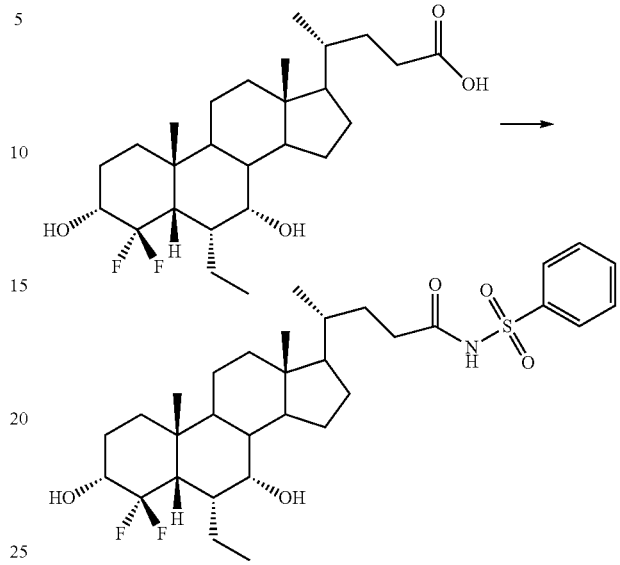

Prepared according to general procedure 4 using 400 mg of 3α, 7α-dihydroxyl-4,4-difluoro-6α-ethyl-5β-cholanic acid from Step C to afford the title compound N-(3α,7α-dihydroxyl-4,4-difluoro-6α-ethyl-5β-cholan-24-oyl)-benzene sulphonamide a white solid (161 mg, 0.27 mmol, 31%).

$^1$H NMR (400 MHz, CDCl$_3$): δ 8.06 (2H, dd, J=7.6, 1.3 Hz), 7.64 (1H, tt, J=7.6, 0.8 Hz), 7.54 (2H, t, J=7.3 Hz), 3.85-3.69 (2H, m), 2.45 (1H, dd, J=32.1, 11.0 Hz), 2.27 (1H, ddd, J=15.3, 10.2, 5.0 Hz), 2.16-2.10 (1H, m), 1.97-1.89 (3H, m), 1.86-1.64 (8H, m), 1.61-1.54 (1H, m), 1.47-1.43 (4H, m), 1.37-1.29 (2H, m), 1.22-1.06 (6H, m), 1.03 (3H, s), 0.97 (3H, t, J=7.3 Hz), 0.84 (3H, d, J=6.2 Hz), 0.59 (3H, s) ppm.

$^{19}$F NMR ($^1$H non-decoupled, 376 MHz, CDCl$_3$): δ−99.0 (1F, d, J=239.3 Hz), −111.0 (1F, dtd, J=239.3, 33.0, 26.0 Hz) ppm.

LRMS (ESI$^+$) m/z: 613.6, [M+NH$_4$]$^+$, 100%.

Example 5—Synthesis of 6α-ethyl-2α/β,4β-difluoro-(3α,7α)-dihydroxyl-5β-cholanic Acid Analogues with Sulfonylurea and Sulfonamide Side Chains A. Methyl 6α-ethyl-2α/β,4β-difluoro-7α-hydroxyl-3-oxo-5β-cholan-24-oate

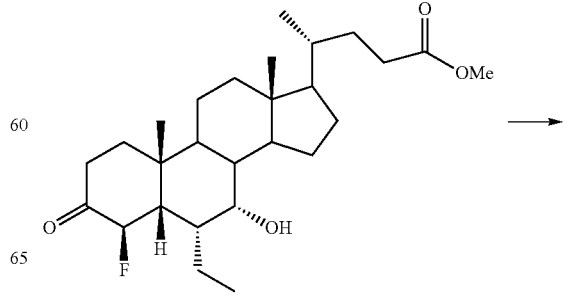

73
-continued

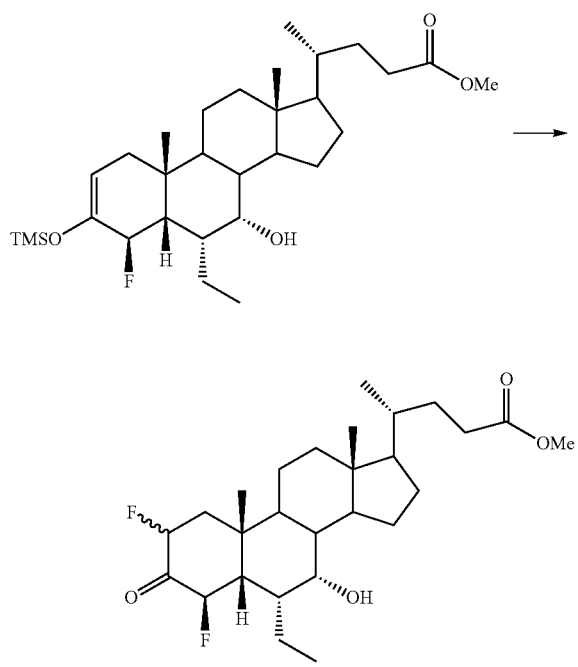

To a stirred, pre-cooled solution of 1M LDA in THF/hexanes (1.63 mL, 1.625 mmol) and TMS-Cl (0.21 mL, 1.626 mmol) in dry THF (6 mL) at −78° C. was added a solution of methyl 6α-ethyl-4β-fluoro-7α-hydroxyl-3-oxo-5β-cholan-24-oate (product of Example 1C; 170 mg, 0.325 mmol) in dry THF (2.5 mL) dropwise over 10 mins. After addition the reaction was gradually allowed to warm to RT and stirred for 20 h. Upon completion the reaction mixture was cooled to 0° C. and quenched via dropwise addition of saturated NaHCO$_3$ (5 mL) and diluted with H$_2$O (5 mL). The organic phase was removed and the aqueous phase back extracted with EtOAc (3×5 mL). The combined organics were washed with NaHCO$_3$ (5 mL), H$_2$O (5 mL) and brine (5 mL). Organic phases were combined, dried over MgSO$_4$, filtered and concentrated in vacuo to yield a yellow oil. The resultant syrup was used for the next reaction without further purification.

$^{19}$F NMR ($^1$H non-decoupled, 376 MHz): δ−169.9 (1F, s);

To a stirred solution of methyl-3-trimethylsilyl-6α-ethyl-4β-fluoro-7α-hydroxyl-5β-cholan-2-ene-24-oate (assume 0.19 g, 0.325 mmol) in dry MeCN (10 mL) was added SELECTFLUOR® (0.17 g, 0.488 mmol) portion wise and the reaction stirred at RT for 16 h. Upon completion the reaction was diluted with EtOAc (5 mL) and sat. NaHCO$_3$ (3 mL). Organic phase removed and the aqueous phase back extracted with EtOAc (3×5 mL). Organic phases combined, dried over MgSO$_4$, filtered and concentrated in vacuo to yield a yellow oil. The procedures described above in Examples 2D and 2E were carried out on the product of Step A to obtain methyl 6α-ethyl-2α/β,4β-difluoro-(3α,7α)-dihydroxyl-5β-cholan-24-oate. This compound can be converted to the equivalent sulfonyl urea or sulfonamide analogues using General Procedures 1 to 4 as described in Examples 1 to 3 above.

74
Synthesis of 2β-Fluoro Compounds

2α-Fluoro and 4α-fluoro derivatives of obeticholic acid were prepared as described below.

Example 6—Synthesis of 2β-fluoro-3α,7α-dihydroxyl-6α-ethyl-5β-cholanic Acid Analogues with Sulfonylurea and Sulfonamide Side Chains A. Methyl-3,7-dioxo-6α-ethyl-5β-cholan-24-oate

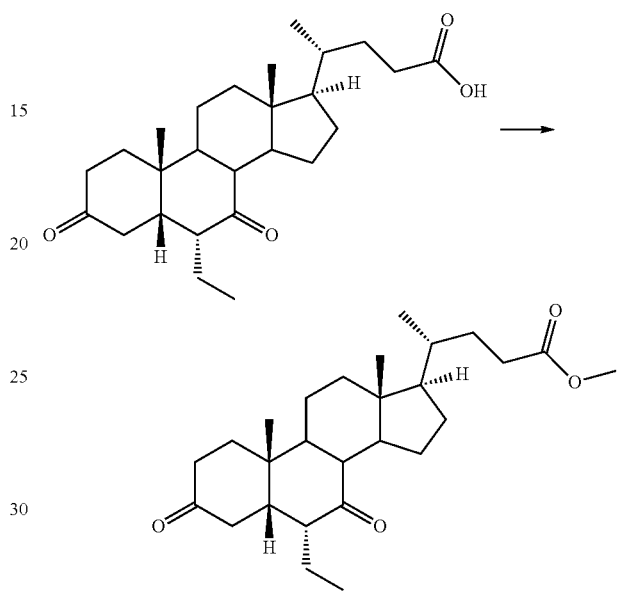

To a solution of (6α, 5β, 7α)-6-ethyl-7-hydroxy-3,7-dioxo-cholan-24-oic acid prepared as described in WO 2016/079520 (36.0 g, 87.7 mmol, 1.0 equiv.) in methanol (800 mL) at RT was added para-toluenesulfonic acid (1.67 g, 8.78 mmol, ~0.1 equiv.) and sonicated at 30° C. for 4 hours. The reaction was deemed complete by TLC and the reaction mixture was concentrated in vacuo. The residue was dissolved in chloroform (400 mL) and washed with sat. NaHCO$_3$ solution (400 mL) and brine (400 mL), dried over Na$_2$SO$_4$, filtered and concentrated in vacuo to afford 37.6 g of crude material as a white solid that was used without further purification (87.3 mmol, 99%).

$^1$H NMR (400 MHz, CDCl$_3$): δ 3.66 (3H, s), 2.74 (1H, m), 2.47 (1H, t, J=11.3 Hz), 2.35 (1H, ddd, J=15.4, 10.0, 5.3 Hz), 2.26-2.14 (6H, m), 2.10-1.77 (6H, m), 1.74-1.35 (7H, m), 1.33 (3H, s), 1.31-1.26 (1H, m), 1.21-0.96 (4H, m), 0.93 (3H, d, J=6.5 Hz), 0.80 (3H, t, J=7.4 Hz), 0.69 (3H, s) ppm. LRMS (ESI$^+$) m/z: 448.3 [M+NH$_4$]$^+$, 100%.

B. Methyl-3β-hydroxyl-6α-ethyl-7-oxo-5β-cholan-24-oate and methyl-3α-hydroxyl-6α-ethyl-7-oxo-5β-cholan-24-oate

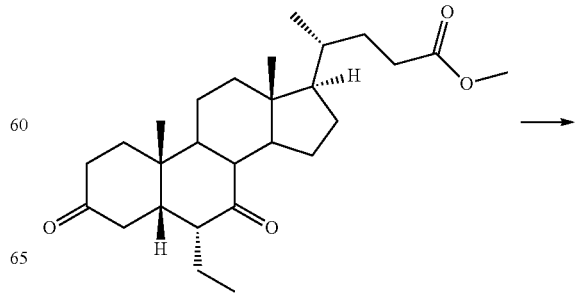

C. Methyl-6α-ethyl-7oxo-5β-chol-2-ene-24-oate and methyl-6α-ethyl-7-oxo-5β-chol-3-ene-24-oate

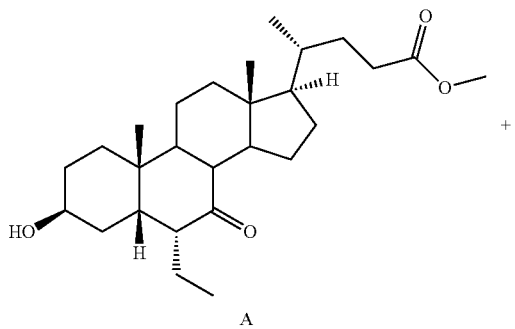

A

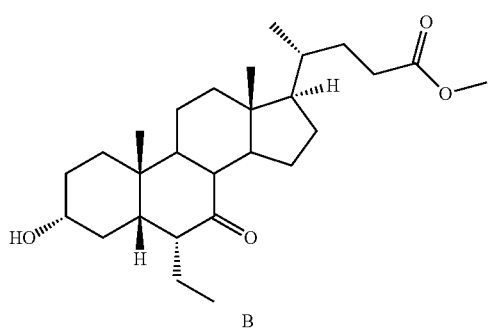

B

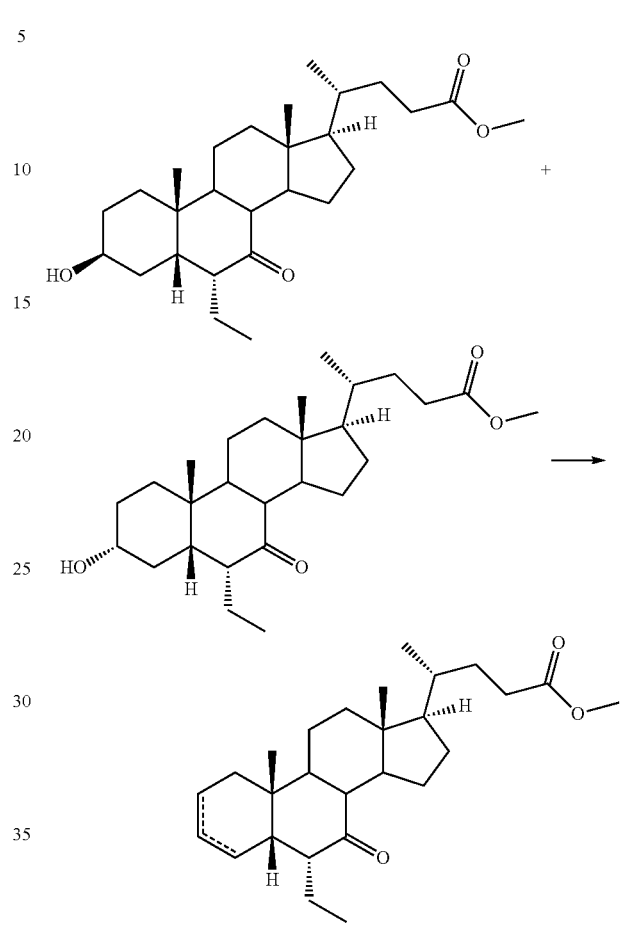

To a dry solution of methyl-3,7-dioxo-6α-ethyl-5β-cholan-24-oate of Step A (10.0 g, 23.2 mmol, 1.0 equiv.) in tetrahydrofuran (340 mL) at −78'C. under argon was added L-SELECTRIDE® (35.0 mL; 34.8 mmol, ~2.5 equiv.) dropwise over 15 minutes. After 10 minutes, the reaction mixture received a solution of hydrogen peroxide (40 mL, 30% v/v) and 2M sodium hydroxide (40 mL) in water (400 mL) at 0° C. After a further 10 minutes, the reaction mixture received 2M hydrochloric acid (130 mL) at RT. The aqueous phase was separated and extracted with ethyl acetate (2×250 mL) and the combined organic fractions were washed with water (500 mL), dried over $Na_2SO_4$, filtered and concentrated in vacuo to afford 11.0 g of crude material as a colourless oil. Purification by flash column chromatography (Biotage SNAP KP-Sil 100 g cartridge) using PE 40-60/acetone (90/10 to 80/20) as the eluent yielded an inseparable mixture of compound Methyl-3β-hydroxyl-6α-ethyl-7-oxo-5β-cholan-24-oate and methyl-3α-hydroxyl-6α-ethyl-7-oxo-5β-cholan-24-oate in a 65:35 ratio as a white residue (7.83 g, 18.1 mmol, 78%). to the mixture was not separated as both compounds lead to the same mixture of alkenes in the next step.

Compound A: $^1$H NMR (400 MHz, $CDCl_3$): δ 4.05 (1H, t, J=2.5 Hz), 3.66 (3H, s), 2.77-2.73 (1H, m), 2.41-2.31 (2H, m), 2.26-2.14 (3H, m), 2.00-1.88 (2H, m), 1.84-1.58 (6H, m), 1.55-1.29 (10H, m), 1.25 (3H, s), 1.15-1.07 (4H, m), 0.92 (3H, d, J=6.5 Hz), 0.81 (3H, t, J=7.4 Hz), 0.66 (3H, s).

LRMS ($ESI^+$) m/z: 450.3 $[M+NH_4]^+$, 100%.

Compound B: $^1$H NMR (400 MHz, $CDCl_3$): δ 3.66 (3H, s), 3.57-3.48 (1H, m), 2.76-2.67 (1H, m), 2.41-2.32 (2H, m), 2.26-2.14 (3H, m), 2.00-1.88 (2H, m), 1.84-1.59 (6H, m), 1.55-1.29 (10H, m), 1.22 (3H, s), 1.17-1.07 (4H, m), 0.92 (3H, d, J=6.4 Hz), 0.80 (3H, t, J=7.4 Hz), 0.65 (3H, s) ppm.

LRMS ($ESI^+$) m/z: 450.4 $[M+NH_4]^+$, 100%.

To a solution of methyl-3β-hydroxyl-6α-ethyl-7-oxo-5β-cholan-24-oate and methyl-3α-hydroxyl-6α-ethyl-7-oxo-5β-cholan-24-oate of Step B (6.31 g, 14.6 mmol, 1.0 equiv.) in dichloromethane (120 mL) at RT was added dimethylaminopyridine (3.56 g, 29.2 mmol, ~2.0 equiv.). The reaction mixture was cooled to 0° C. and received triflic anhydride (2.57 mL, 15.3 mmol, ~1.05 equiv.) dropwise over 5 minutes. After 2 hours warming to 12° C. the reaction was deemed complete by TLC and the reaction mixture was quenched with 2M hydrochloric acid (100 mL). The aqueous phase was separated and extracted with dichloromethane (3×100 mL) and the combined organic fractions were washed with brine (200 mL), dried over $Na_2SO_4$, filtered and concentrated in vacuo to afford 7.56 g of crude material as an orange oil. Purification by flash column chromatography (Biotage SNAP KP-Sil 100 g cartridge) using PE 40-60/acetone (90/10) as the eluent yielded an inseparable mixture of methyl-6α-ethyl-7oxo-5β-chol-2-ene-24-oate and methyl-6α-ethyl-7-oxo-5β-chol-3-ene-24-oate in a 80:20 ratio as a colourless oil (2.70 g, 6.51 mmol, 45%).

$^1$H NMR (400 MHz, $CDCl_3$): δ 5.63-5.40 (2H, m), 3.66 (3H, s,), 2.74 (1H, dd, J=12.0, 6.6 Hz), 2.34 (2H, tt, J=10.3, 5.1 Hz), 2.27-1.29 (19H, m), 1.27 (2H, s), 1.26 (1H, s), 1.18-0.94 (3H, m), 0.91 (3H, d, J=6.5 Hz), 0.83 (3H, t, J=7.5 Hz), 0.664 (1H, s), 0.657 (2H, s) ppm.

LRMS ($ESI^+$) m/z: 432.20 $[M+NH_4]^+$, 100%.

D. Methyl-2β,3β-epoxy-6α-ethyl-7-oxo-5β-cholan-24-oate and methyl-3β,4β-epoxy-6α-ethyl-7-oxo-5β-cholan-24-oate

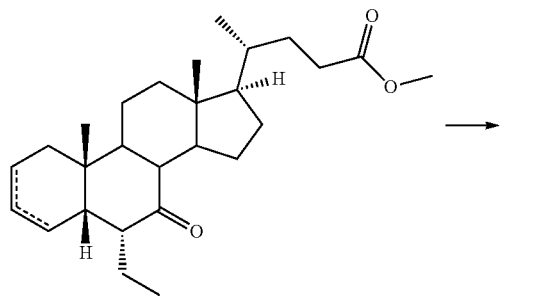

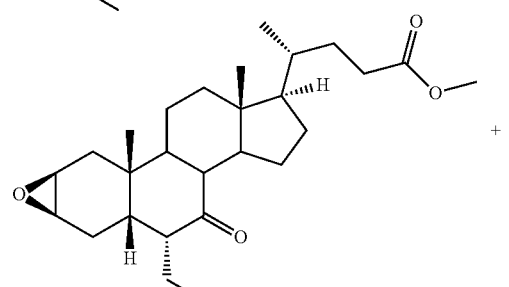

A

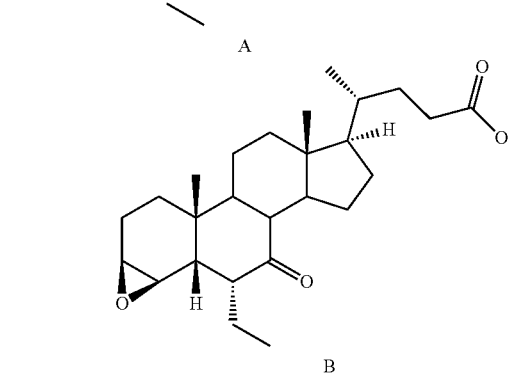

B

To a solution of a 80:20 ratio of methyl-6α-ethyl-7oxo-5β-chol-2-ene-24-oate and methyl-6α-ethyl-7-oxo-5β-chol-3-ene-24-oate of Step C (5.00 g, 12.1 mmol, ~1.0 equiv.) in dichloromethane (100 mL) at RT was added meta-perchlorobenzoic acid (3.12 g, 18.1 mmol, ~1.5 equiv.). After 3 hours at RT, the reaction was deemed complete by TLC and the reaction mixture was quenched with sat. Na$_2$S$_2$O$_3$ solution (150 mL). After 10 mins stirring, the aqueous phase was separated and extracted with dichloromethane (3×100 mL) and the combined organic fractions were dried over Na$_2$SO$_4$, filtered and concentrated in vacuo to afford 5.28 g of crude material as a pale yellow residue. Purification by flash column chromatography (Biotage SNAP KP-Sil 100 g cartridge) using PE 40-60/acetone (95/5 to 90/10) as the eluent yielded an inseparable mixture of methyl-2β,3β-epoxy-6α-ethyl-7-oxo-5β-cholan-24-oate and methyl-3β,4β-epoxy-6α-ethyl-7-oxo-5β-cholan-24-oate as a colourless oil (4.94 g, 11.5 mmol, 95%). Further purification by flash column chromatography (Biotage SNAP KP-Sil 340 g cartridge) using PE 40-60/acetone (95/5 to 90/10) as the eluent yielded compound methyl-2β,3β-epoxy-6α-ethyl-7-oxo-5β-cholan-24-oate as a colourless oil (3.71 g, 8.62 mmol, 72%) and compound methyl-3β,4β-epoxy-6α-ethyl-7-oxo-5β-cholan-24-oate as a colourless oil (1.18 g, 2.74 mmol, 23%).

Compound A: $^1$H NMR (400 MHz, CDCl$_3$): δ 3.66 (3H, s), 3.13 (1H, t, J=2.6 Hz), 3.01 (1H, dd, J=5.5, 4.2 Hz), 2.67 (1H, dd, J=11.5, 6.6 Hz), 2.35 (1H, ddd, J=15.4, 10.2, 5.1 Hz), 2.30-2.18 (3H, m), 2.01-1.65 (7H, m), 1.55-1.20 (10H, m), 1.17 (3H, s), 1.15-0.95 (3H, m), 0.92 (3H, d, J=6.4 Hz), 0.81 (3H, t, J=7.4 Hz), 0.65 (3H, s) ppm.

LRMS (ESI$^+$) m/z: 448.30 [M+NH$_4$]$^+$, 100%.

Compound B: $^1$H NMR (400 MHz, CDCl$_3$): δ 3.66 (3H, s), 3.10-3.09 (1H, m), 2.79-2.74 (2H, m), 2.41-2.31 (2H, m), 2.26-2.04 (3H, m), 2.00-1.88 (4H, m), 1.84-1.58 (2H, m), 1.53-1.20 (11H, m), 1.17 (3H, s), 1.14-0.94 (2H, m), 0.91 (3H, d, J=6.3 Hz), 0.90 (3H, t, J=7.5 Hz), 0.66 (3H, s) ppm.

LRMS (ESI$^+$) m/z: 448.26 [M+NH$_4$]$^+$, 100%.

E. Methyl-2α-fluoro-3α-hydroxyl-6α-ethyl-7-oxo-5β-cholan-24-oate

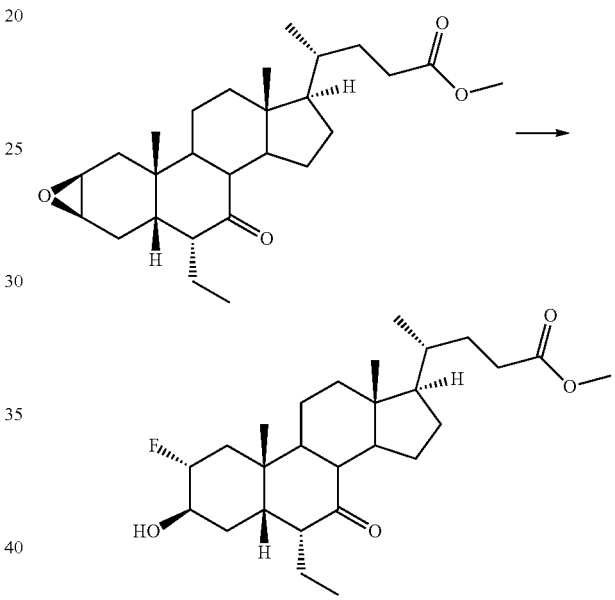

To a dry solution of methyl-2β,3β-epoxy-6α-ethyl-7-oxo-5β-cholan-24-oate of Step D (3.33 g, 7.73 mmol, 1.0 equiv.) in dichloromethane (100 mL) at 0° C. under argon was added HF.pyridine (70%) complex (100 mL, 3.86 mol, ~500 equiv.) by pouring a freshly opened 100 mL bottle into the cooled reaction flask via a glass funnel whilst under a steady flow of argon. After addition of the reagent, the bottle and funnel were rinsed with dichloromethane (20 mL). After 3 hours at 0° C., the reaction mixture was diluted with dichloromethane (200 mL) and quenched by the slow addition of sat. NaHCO$_3$ solution (500 mL) and stirred at RT for 1 hour whilst receiving 5.0 g of NaHCO$_3$ in 100 mg portions. The aqueous phase was then separated and extracted with dichloromethane (3×250 mL) and the combined organic fractions were dried over Na$_2$SO$_4$, filtered and concentrated in vacuo to afford 3.61 g of crude material as a colourless oil. Purification by flash column chromatography (Biotage SNAP KP-Sil 100 g cartridge) using PE 40-60/acetone (95/5 to 90/150 as the eluent yielded compound methyl-2α-fluoro-3α-hydroxyl-6α-ethyl-7-oxo-5β-cholan-24-oate as a white residue (2.39 g, 5.30 mmol, 69%).

$^1$H NMR (400 MHz, CDCl$_3$): δ 4.53 (1H, dq, J=47.0, 2.3 Hz), 4.01 (1H, dq, J=6.6, 2.9 Hz), 3.66 (3H, s), 2.75 (1H, dd, J=13.3, 5.8 Hz), 2.38-2.30 (2H, m), 2.25-2.11 (4H, m), 2.01

(1H, dd, J=12.0, 3.8 Hz), 1.93-1.36 (14H, m), 1.25 (3H, d, J=4.0 Hz), 1.21-1.10 (3H, m), 0.91 (3H, d, J=6.5 Hz), 0.82 (3H, t, J=7.4 Hz), 0.65 (3H, s) ppm $^{19}$F NMR ($^1$H non-decoupled, 376 MHz, CDCl$_3$): δ−184.3 (1F, tt, J=50.3, 8.7 Hz) ppm.

LRMS (ESI$^+$) m/z: 468.28 [M+NH$_4$]$^+$, 100%.

F. Methyl-2α-fluoro-3,7-dioxo-6α-ethyl-5β-cholan-24-oate

G. 2α-Fluoro-3,7-dioxo-6α-ethyl-5β-cholanic Acid and 2β-fluoro-3,7-dioxo-6α-ethyl-5β-cholanic Acid

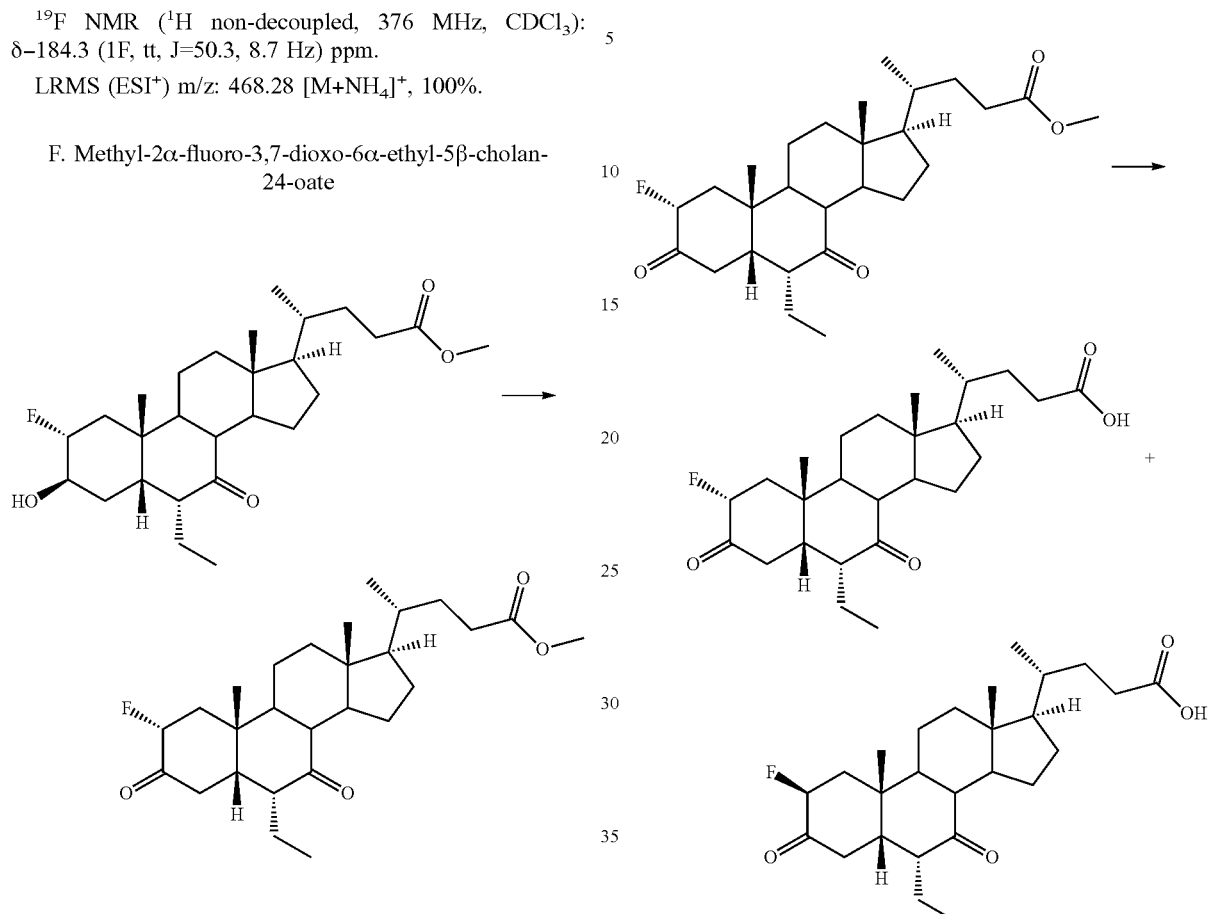

To a solution of methyl-2α-fluoro-3α-hydroxyl-6α-ethyl-7-oxo-5β-cholan-24-oate of Step E (1.00 g, 2.26 mmol, 1.0 equiv.) in dichloromethane (20 mL) at RT was added Dess-Martin periodinane (1.92 g, 4.52 mmol, ~2.0 equiv.) and H$_2$O (0.25 mL). After 3 hours at RT, the reaction was deemed complete by TLC and the reaction mixture was quenched with sat. NaHCO$_3$ solution (25 mL) and filtered over Celite and washed with dichloromethane (90 mL). The aqueous phase was then separated and extracted with dichloromethane (2×50 mL) and the combined organic layers were washed with sat. Na$_2$S$_2$O$_3$ solution (150 mL), dried over Na$_2$SO$_4$, filtered and concentrated in vacuo to afford 1.21 g of crude material as a pale yellow oil. Purification by flash column chromatography (Biotage SNAP KP-Sil 25 g cartridge) using PE 40-60/acetone (95/5 to 90/10) as the eluent yielded compound methyl-2α-fluoro-3,7-dioxo-6α-ethyl-5β-cholan-24-oate as a white residue (568 mg, 1.27 mmol, 56%).

$^1$H NMR (400 MHz, CDCl$_3$): δ 4.69 (1H, ddd, J=50.7, 4.8, 3.4 Hz), 3.68 (3H, s), 2.75 (1H, ddd, J=7.7, 5.0, 4.3 Hz), 2.51-1.94 (12H, m), 1.83-1.40 (9H, m), 1.37 (3H, s), 1.34-1.08 (5H, m), 0.94 (3H, d, J=6.5 Hz), 0.84 (3H, t, J=7.4 Hz), 0.70 (3H, s) ppm.

$^{19}$F NMR ($^1$H non-decoupled, 376 MHz, CDCl$_3$): δ−188.2 (1F, ddd, J=51.6, 42.1, 12.1 Hz) ppm.

LRMS (ESI$^+$) m/z: 466.55 [M+NH$_4$]$^+$, 100%.

To a solution of methyl-2α-fluoro-3,7-dioxo-6α-ethyl-5β-cholan-24-oate (product of Step F, 878 mg, 1.95 mmol, 1.0 equiv.) in methanol (20 mL) at RT was added sodium hydroxide (1.0 g). After 19 hours at RT the reaction was deemed complete by TLC and the reaction mixture was acidified to pH 4.0 and concentrated in vacuo. The residue was dissolved in ethyl acetate (50 mL) and washed with 1M hydrochloric acid (50 mL), dried over Na$_2$SO$_4$, filtered and concentrated in vacuo to afford 968 mg of crude material as a colourless oil. Purification by flash column chromatography (Biotage SNAP KP-Sil 25 g cartridge) using dichloromethane/methanol (98/2 to 90/10) as the eluent yielded an inseparable mixture of 2α-fluoro-3,7-dioxo-6α-ethyl-5β-cholanic acid and 2β-fluoro-3,7-dioxo-6α-ethyl-5β-cholanic acid in a 40:60 ratio as a white residue (772 mg, 1.77 mmol, 91%). 2α-fluoro-3,7-dioxo-6α-ethyl-5β-cholanic acid: $^1$H NMR—characteristic peaks (400 MHz, CDCl$_3$): δ 4.68 (1H, ddd, J=50.7, 5.1, 3.6 Hz), 2.75 (1H, ddd, J=7.7, 5.0, 4.3 Hz), 1.36 (3H, s), 0.94 (3H, d, J=6.5 Hz), 0.82 (3H, t, J=7.3 Hz), 0.69 (3H, s) ppm.

$^{19}$F NMR ($^1$H non-decoupled, 376 MHz, CDCl$_3$): δ−188.2 (1F, ddd, J=51.6, 42.1, 12.1 Hz) ppm.

LRMS (ESI$^+$) m/z: 452.51 [M+NH$_4$]$^+$, 100%.

2β-fluoro-3,7-dioxo-6α-ethyl-5β-cholanic Acid $^1$H NMR—characteristic peaks (400 MHz, CDCl$_3$): δ 4.90 (0.6H, ddd, J=48.7, 13.2, 6.1 Hz), 2.75 (1H, ddd, J=7.7, 5.0, 4.3 Hz), 1.39 (2H, s), 0.95 (2H, d, J=6.5 Hz), 0.82 (3H, t, J=7.3 Hz), 0.70 (2H, s) ppm.
$^{19}$F NMR ($^{1}$H non-decoupled, 376 MHz, CDCl$_3$): δ−195.1 (1F, ddd, J=48.6, 10.4, 5.2 Hz) ppm.
LRMS (ESI$^+$) m/z: 452.51 [M+NH$_4$]$^+$, 100%.

H. Methyl-2β-fluoro-3,7-dioxo-6α-ethyl-5β-cholan-24-oate

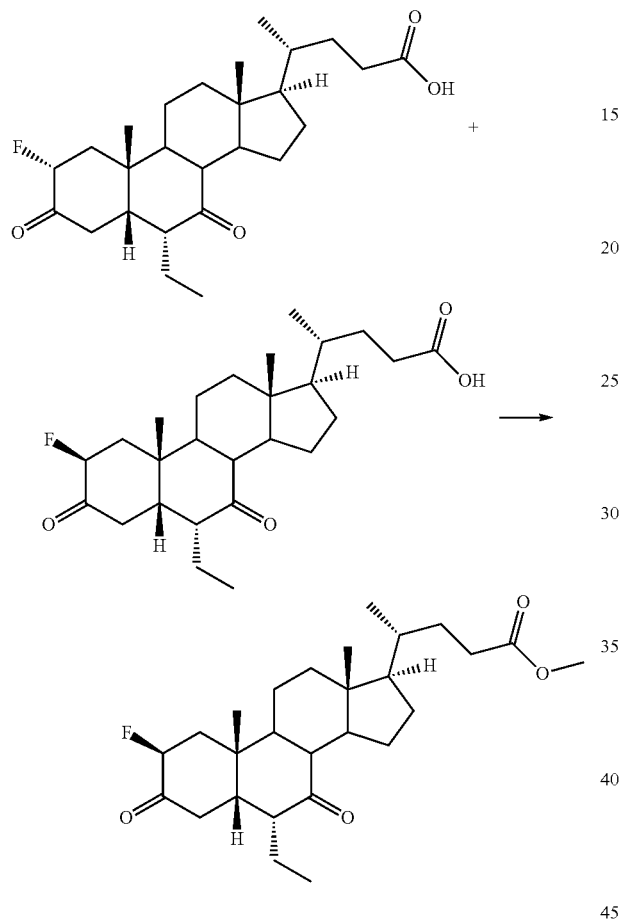

To a solution of a 40:60 ratio of 2α-fluoro-3,7-dioxo-6α-ethyl-5β-cholanic acid and 2β-fluoro-3,7-dioxo-6α-ethyl-5β-cholanic acid of Step G (750 mg, 1.72 mmol, ~1.0 equiv.) in dimethylformamide (17 mL) at RT was added caesium carbonate (840 mg, 2.58 mmol, ~1.5 equiv). After 20 mins at RT, iodomethane (0.54 mL, 8.59 mmol, ~5.0 equiv.) was added dropwise. After 19 hours at RT, the reaction was deemed complete by TLC and the reaction mixture was concentrated in vacuo. The residue was dissolved in ethyl acetate (25 mL) and H$_2$O (20 mL). The aqueous layer was separated and extracted with ethyl acetate (3×25 mL) and the combined organic layers were washed with brine (100 mL), dried over Na$_2$SO$_4$, filtered and concentrated in vacuo to afford a 917 mg of crude material as a pale yellow oil. Purification by flash column chromatography (Biotage SNAP Ultra KP-Sil 25 g cartridge) using PE 40-60/acetone (95/5 to 90/10) as the eluent yielded compound methyl-2β-fluoro-3,7-dioxo-6α-ethyl-5β-cholan-24-oate as a white residue (416 mg, 0.95 mmol, 54%). The corresponding 2α-fluoro derivative was not isolated.

$^{1}$H NMR (400 MHz, CDCl$_3$): δ 4.69 (1H, ddd, J=48.8, 13.3, 6.4 Hz), 3.67 (3H, s), 2.75 (1H, dd, J=13.1, 5.0 Hz), 2.54-2.44 (2H, m), 2.40-2.32 (2H, m), 2.29-2.13 (3H, m), 2.09 (1H, dt, J=13.0, 3.3 Hz), 2.01-1.91 (2H, m), 1.85-1.65 (5H, m), 1.54-1.42 (2H, m), 1.39 (3H, s), 1.38-1.05 (7H, m), 0.94 (3H, d, J=6.5 Hz), 0.82 (3H, t, J=7.4 Hz), 0.70 (3H, s) ppm.
$^{19}$F NMR ($^{1}$H non-decoupled, 376 MHz, CDCl$_3$): δ−195.1 (1F, ddt, J=48.6, 10.4, 5.2 Hz) ppm.
LRMS (ESI$^+$) m/z: 466.59 [M+NH$_4$]$^+$, 100%.

I. Methyl-2β-fluoro-3β,7α-dihydroxyl-6α-ethyl-5β-cholan-24-oate and methyl-2β-fluoro-3α,7α-dihydroxyl-6α-ethyl-5β-cholan-24-oate

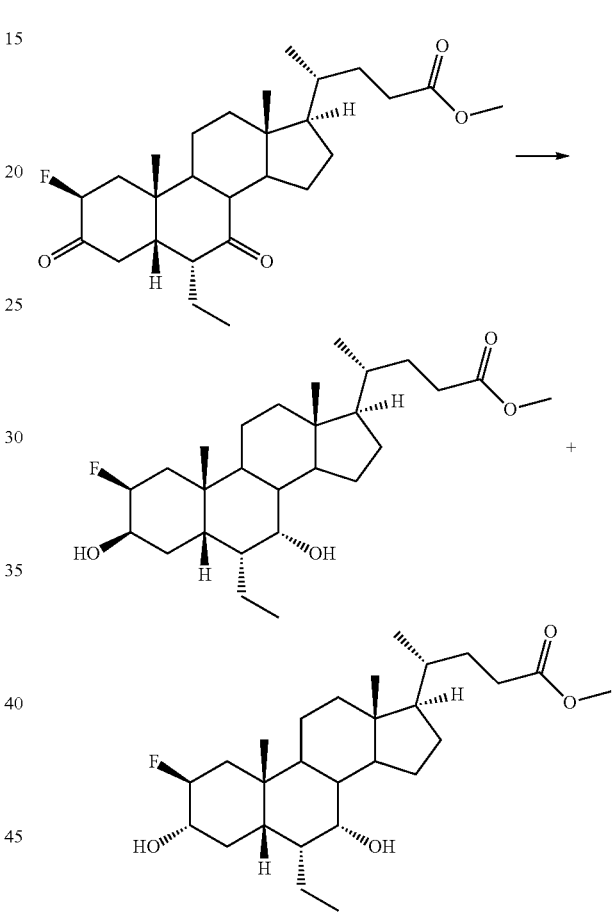

To a dry solution of methyl-2β-fluoro-3,7-dioxo-6α-ethyl-5β-cholan-24-oate of Step H (390 mg, 0.87 mmol, 1.0 equiv.) in methanol (20 mL) under argon at RT was added sodium borohydride (164 mg, 4.44 mmol, 5.0 equiv.). After 1 hour at RT, the reaction mixture was concentrated in vacuo. The residue was dissolved in dichloromethane (20 mL) and H$_2$O (20 mL) and the aqueous phase was separated and extracted with dichloromethane (3×20 mL). The combined organic fractions were dried over Na$_2$SO$_4$, filtered and concentrated in vacuo to afford 446 mg of crude material as a pale yellow oil. Purification by flash column chromatography (Biotage SNAP Ultra KP-Sil 25 g cartridge) using PE 40-60/acetone (95/5 to 90/10) as the eluent yielded compound methyl-2β-fluoro-3β,7α-dihydroxyl-6α-ethyl-5β-cholan-24-oate as a colourless oil (161 mg, 0.36 mmol, 41%) and methyl-2β-fluoro-3α,7α-dihydroxyl-6α-ethyl-5β-cholan-24-oate as a colourless oil (146 mg, 0.32 mmol, 37%).

Methyl-2β-fluoro-3β,7α-dihydroxyl-6α-ethyl-5β-cholan-24-oate $^1$H NMR (400 MHz, CDCl$_3$): δ 4.63 (1H, dddd, J=47.4, 12.5, 4.4, 3.1 Hz,), 4.15 (1H, q, 3.6 Hz), 3.71 (1H, s), 3.67 (3H, s), 2.36 (1H, ddd, J=15.5, 10.2, 5.3 Hz), 2.33 (1H, ddd, J=16.0, 9.7, 6.6 Hz), 2.12 (1H, td, J=13.2, 2.2 Hz), 2.00 (1H, dt, J=12.5, 3.1 Hz), 1.94-1.78 (5H, m), 1.77-1.54 (6H, m), 1.52-1.25 (8H, m), 1.20-1.12 (4H, m), 1.00 (3H, s), 0.93 (3H, d, J=6.8 Hz), 0.92 (3H, t, J=7.1 Hz), 0.67 (3H, s) ppm.
$^{19}$F NMR ($^1$H non-decoupled, 376 MHz, CDCl$_3$): δ−187.1 (1F, dquin, J=46.9, 7.8 Hz) ppm.
LRMS (ESI$^+$) m/z: 470.64 [M+NH$_4$]$^+$, 100%.

methyl-2β-fluoro-3α,7α-dihydroxyl-6α-ethyl-5β-cholan-24-oate $^1$H NMR (400 MHz, CDCl$_3$): δ 4.42 (1H, dddd, J=52.7, 12.5, 8.7, 4.5 Hz), 3.70 (1H, s), 3.67 (3H, s), 3.52 (1H, ddt, 13.8, 12.5, 6.0 Hz), 2.36 (1H, ddd, J=15.4, 10.2, 5.3 Hz), 2.27-2.17 (3H, m), 2.09-1.97 (2H, m), 1.95-1.86 (2H, m), 1.84-1.76 (1H, m), 1.66-1.29 (14H, m), 1.22-1.13 (4H, m), 0.98 (3H, s), 0.93 (3H, d, J=6.5 Hz), 0.92 (3H, t, J=7.2 Hz), 0.67 (3H, s) ppm.
$^{19}$F NMR ($^1$H non-decoupled, 376 MHz, CDCl$_3$): δ−188.2 (1F, ddd, J=51.6, 42.1, 12.1 Hz) ppm.
LRMS (ESI$^+$) m/z: 470.64 [M+NH$_4$]$^+$, 100%.

J. 2β-Fluoro-3α,7α-dihydroxyl-6α-ethyl-5β-cholanic Acid

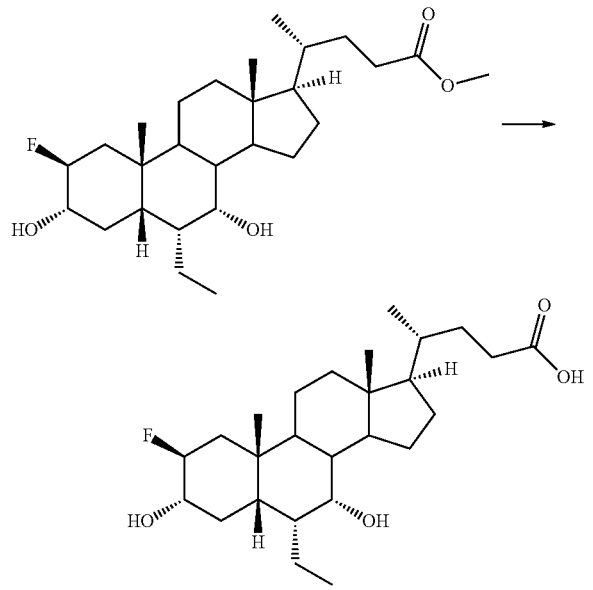

To a solution of methyl-2β-fluoro-3α,7α-dihydroxyl-6α-ethyl-5β-cholan-24-oate of Step I (119 mg, 0.26 mmol, 1.0 equiv.) in a solution of 1,4-dioxane (9.8 mL) and water (3.6 mL) at RT was added concentrated (37%) hydrochloric acid (1.2 mL, 9:3:1 ratio). After 1 hour at reflux, the reaction was deemed complete by TLC and the reaction mixture was neutralised with sat. NaHCO$_3$ solution (20 mL). The aqueous phase was extracted with ethyl acetate (3×15 mL) and the combined organic fractions were dried over Na$_2$SO$_4$, filtered and concentrated in vacuo to afford 141 mg of crude material as a colourless oil. Purification by flash column chromatography (Biotage SNAP Ultra KP-Sil 10 g cartridge) using dichloromethane/methanol (95/5 to 90/10) as the eluent yielded compound 2β-fluoro-3α,7α-dihydroxyl-6α-ethyl-5β-cholanic acid as a white residue (92 mg, 0.21 mmol, 80%).

$^1$H NMR (400 MHz, CDCl$_3$): δ 4.42 (1H, dddd, J=52.6, 12.5, 8.7, 4.3 Hz), 3.69 (1H, s), 3.52 (1H, tdd, 12.0, 8.8, 5.4 Hz), 2.39 (1H, ddd, J=15.5, 10.3, 5.1 Hz), 2.29-2.19 (3H, m), 2.01 (2H, t, J=13.0 Hz), 1.93-1.77 (3H, m), 1.65-1.54 (3H, m), 1.53-1.26 (12H, m), 1.23-1.10 (4H, m), 0.97 (3H, s), 0.94 (3H, d, J=6.5 Hz), 0.91 (3H, t, J=7.1 Hz), 0.66 (3H, s) ppm.
$^{19}$F NMR ($^1$H non-decoupled, 376 MHz, CDCl$_3$): δ−186.8 (1F, ddq, J=52.9, 13.0, 7.5 Hz,) ppm.
LRMS (ESI$^+$) m/z: 456.60 [M+NH$_4$]$^+$, 100%.

This compound can be converted to the equivalent sulfonyl urea or sulfonamide analogues using General Procedures 1 to 4 as described in Examples 1 to 3 above.

BIOLOGICAL EXAMPLES

For Biological Examples 8 and 9 below, all work has been carried out and data has been kindly supplied by Professor Kim Watson and Dannielle Kydd-Sinclair of the University of Reading, UK.

Example 7—Measurement of EC$_{50}$ and Efficacy at FXR Receptor

The compounds of the invention were assayed for agonist activity at the FXR receptor. Table 1 shows the EC$_{50}$ values and efficacy values for example compounds of the present invention compared with the values for comparative example compounds, obeticholic acid and the known FXR agonist GW4064, which has the structure:

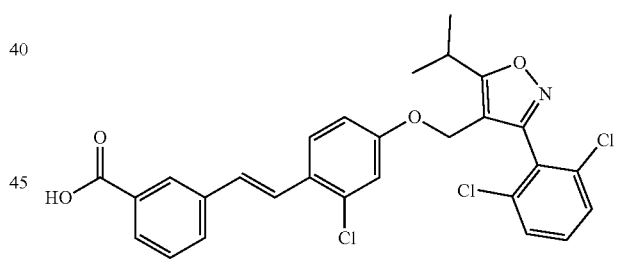

Efficacy is defined as the maximum point on the dose response curve and the efficacy value for GW4064 in Table 1 has been designated as 100%.

The EC$_{50}$ values in Table 1 are normalized against the EC$_{50}$ of GW4064, which has been assigned as 25 nM.

Obeticholic acid may be prepared as described in WO 02/072598 or our applications WO 2016/079518, WO 2016/079518, WO 2016/079519 and WO 2016/079520.

FXR EC$_{50}$/Efficacy Protocol

Dose-response assays were performed as described in the technical manual of the Human Farnesoid X Receptor (NR1H4, FXR) Reporter Assay System (Indigo Biosciences Human Farnesoid X Receptor (NR1H4, FXR) Reporter Assay System, Technical Manual (version 7.1b), at the World Wide Web (www)indiqobiosciences.com).

FXR reporter cells consisting of an FXR-responsive promoter gene functionally linked to the luciferase gene were defrosted and seeded into a 96-well plate and these cells were immediately dosed with the test compounds at different concentrations (10-0.05 μM) according to the manufacturer's protocol. After 24 h incubation in the presence of the test compound or solvent (DMSO), the cell viability of these treated/untreated reporter cells was measured to eliminate false negative results using the fluorescence-based live cell multiplex (LCM) assay (Indigo Biosciences Live Cell Multiplex Assay, Technical Manual (version 3.1), at the World Wide Web (www)indigobiosciences.com). The fluorescence from the live cells was measured using the plate reader with the filter combination of [485nmEx|535nmEm]. Following this, the induction of luciferase activity, which is the measure of the agonist activity, was quantified by using luminometer (TECAN) according to the manufacturer's protocol.

Positive controls were run in each assay in which the $EC_{50}$ values of GW4064 was assigned as 25 nM and GW4064 assigned efficacy of 100%. The efficacy and $EC_{50}$ of each test compound was compared to that of GW4064.

The results are set out in Table 1.

TABLE 1

| Compound | A-Ring | Side chain | $EC_{50}$ (nM) | Efficacy (%) |
|---|---|---|---|---|
| Obeticholic acid | No F | 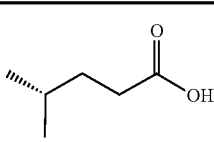 | 109 | 146 |
| GW4064 | — | — | 25 | 100 |
| Compound 1 | 4β-F | 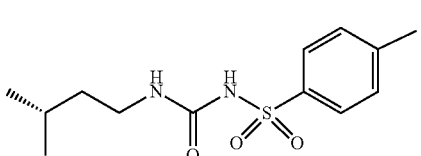 | 18 | 193 |
| Compound 2 | 4β-F | 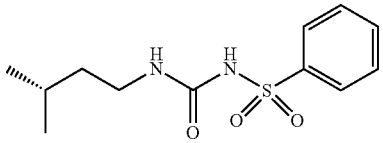 | 24 | 195 |
| Compound 3 | 4β-F | 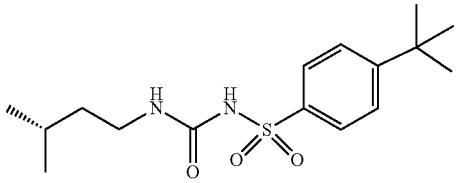 | 19 | 151 |
| Compound 4 | 4β-F | 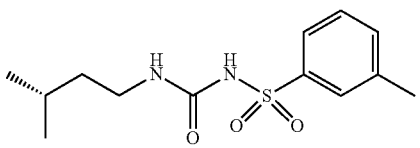 | 23 | 148 |
| Compound 5 | 4β-F | 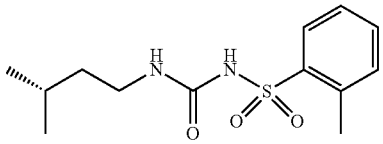 | 28 | 166 |
| Compound 6 | 4β-F | 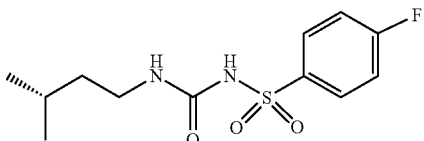 | 32 | 187 |

TABLE 1-continued

| Compound | A-Ring | Side chain | EC$_{50}$ (nM) | Efficacy (%) |
|---|---|---|---|---|
| Compound 7 | 4β-F | 3-fluorophenyl sulfonyl urea side chain | 38 | 131 |
| Compound 8 | 4β-F | 2-fluorophenyl sulfonyl urea side chain | 43 | 159 |
| Compound 9 | 4β-F | 4-CF$_3$-phenyl sulfonyl urea side chain | 50 | 158 |
| Compound 11 | 4β-F | 2-CF$_3$-phenyl sulfonyl urea side chain | 123 | 104 |
| Compound 12 | 4β-F | 4-OCF$_3$-phenyl sulfonyl urea side chain | 27 | 176 |
| Compound 13 | 4β-F | 4-OCH$_3$-phenyl sulfonyl urea side chain | 48 | 250 |
| Comparative compound A | No F | phenyl sulfonyl urea side chain | 32 | 147 |
| Compound 14 | 4β-F | 4-OCF$_3$-phenyl sulfonyl acylamide side chain | 2.34 | 219 |

TABLE 1-continued

| Compound | A-Ring | Side chain | EC$_{50}$ (nM) | Efficacy (%) |
|---|---|---|---|---|
| Compound 15 | 4β-F | 4-F-phenyl sulfonamide | 38 | 98 |
| Compound 16 | 4β-F | 3-F-phenyl sulfonamide | 46 | 143 |
| Compound 17 | 4β-F | 2-F-phenyl sulfonamide | 34 | 121 |
| Compound 18 | 4β-F | 4-CF$_3$-phenyl sulfonamide | 15 | 148 |
| Compound 19 | 4β-F | 3-CF$_3$-phenyl sulfonamide | 50 | 136 |
| Comparative compound B | 4β-F | cyclopropyl sulfonamide | 158 | 132 |
| Comparative compound C | 4β-F | methyl sulfonamide | 192 | 130 |

The compounds of the invention all have FXR agonist activity. All of the compounds apart from Compound 11 have significantly improved EC$_{50}$ values compared with obeticholic acid. Furthermore, the efficacy values for all of the compounds of the invention are at least as good as, and in most cases better than, the value for GW4064.

A comparison of the results for Compound 2 with its unfluorinated analogue Comparative Compound A demonstrates that fluorination improves both the EC$_{50}$ and the efficacy. A comparison of the results for the aromatic sulfonamide Compounds 14 to 20 with the carbocyclic sulfonamide Comparative Compound B and the methylsulfonamide Comparative Compound C demonstrates the importance of the aromatic substituent on the side chain.

Example 8—Measurement of EC$_{50}$ and Efficacy at TGR5 Receptor

Compounds 2 and 14, TGR5 (control) and the taurine and glycine conjugates of obeticholic acid were tested for activity at the TGR5 receptor using a HITHUNTER® cAMP assay available from DiscoverX in the agonist mode to monitor the activation of the TGR5 (GPBAR1) receptor through Gi and Gs secondary messenger signalling. Data was normalized to the maximal and minimal response observed in the presence of control ligand (TGR5) and vehicle.

Assay Design: GPCR cAMP Modulation

Cell Handling 1. cAMP Hunter cell lines were expanded from freezer stocks according to standard procedures.

2. Cells were seeded in a total volume of 20 μL into white walled, 384-well microplates and incubated at 37° C. for the appropriate time prior to testing.

3. cAMP modulation was determined using the DiscoverX HITHUNTER® cAMP XS+assay.

Gs Agonist Format
1. For agonist determination, cells were incubated with sample to induce response.
2. Media was aspirated from cells and replaced with 15 µL 2:1 HBSS/10 mM Hepes:cAMP XS+ Ab reagent.
3. Intermediate dilution of sample stocks was performed to generate 4× sample in assay buffer.
4. 5 µL of 4× sample was added to cells and incubated at 37° C. or room temperature for 30 or 60 minutes. Vehicle concentration was 1%.

Signal Detection
1. After appropriate compound incubation, assay signal was generated through incubation with 20 µL cAMP XS+ ED/CL lysis cocktail for one hour followed by incubation with 20 µL cAMP XS+ EA reagent for three hours at room temperature.
2. Microplates were read following signal generation with a PerkinElmer ENVISION™ instrument for chemiluminescent signal detection.

Data Analysis
1. Compound activity was analyzed using CBIS data analysis suite (ChemInnovation, CA).
2. For Gs agonist mode assays, percentage activity is calculated using the following formula, where RLU is an abbreviation for relative light units:

$$\% \text{Activity} = 100\% \times \left( \frac{\text{mean } RLU \text{ of test sample} - \text{mean } RLU \text{ of vehicle control}}{\text{mean } RLU \text{ of MAX control} - \text{mean } RLU \text{ of vehicle control}} \right)$$

5. For Gi agonist mode assays, percentage activity is calculated using the following formula:

$$\% \text{Activity} = 100\% \times \left( 1 - \frac{(\text{mean } RLU \text{ of test sample} - \text{mean } RLU \text{ of MAX control})}{\text{mean } RLU \text{ of vehicle control} - \text{mean } RLU \text{ of MAX control}} \right)$$

Results

The results are presented in Table 2

TABLE 2

| Compound | EC$_{50}$ (µM) | Max Response |
|---|---|---|
| TGR5 (control) | 0.445 | 101.26 |
| Compound 2 | >100 | 0 |
| Compound 14 | >100 | 0 |
| Obeticholic acid taurine conjugate | 0.979 | 97.70 |
| Obeticholic acid glycine conjugate | 1.904 | 110.9 |

The results demonstrate that, unlike the obeticholic acid conjugates, neither Compound 2 nor Compound 14 has agonist activity at the TGR5 receptor. The compounds are therefore selective FXR agonists.

Example 9—Quantitative Analysis of Ligand-Induced Gene Expression

Compound 2 and obeticholic acid were tested for their effect on the expression of a number of FXR target genes. This example describes cell-based assays and gene expression analysis to observe functional activation of FXR by the compounds of the invention and obeticholic acid at a cellular level.

To assess specific changes in gene expression in response to the test compounds, precise quantification and analysis by quantitative real-time PCR (qPCR) was carried out. Mammalian tissue culture experiments involved seeding Hepatocellular carcinoma, (Huh7) cells, in 6 well plates at a concentration of 1×10$^6$ cells/well and incubating for 24 hours at 37° C. to allow attachment. Cells were exposed to the respective test compound at either its EC$_{50}$ or EC$_{50}$, or vehicle (DMSO), for 24 hours.

Compound 2 and OCA were also tested in the human hepatocellular carcinoma cell line, HepG2. HepG2 cells were also incubated with medium containing OCA or Compound 2 at either its EC$_{50}$ or EC$_{50}$ concentrations for 24 hours.

Testing in Huh7 cells and HepG2 cells was also carried out for Compound 14 in the same way as for Compound 2.

Isolation of Total RNA from Cultured Cells

Total RNA was extracted using the RNAQUEOUS™ Total RNA Isolation kit (Ambion) and all reagents were provided in the kit or prepared according to manufacturer's instructions. For cultured cells, the medium was removed and cells were washed with 1×PBS to remove cellular debris and residual medium. Total RNA was extracted from fresh cells. For 1×10$^6$ cells, 350 µl lysis buffer was added directly to the well and cells were harvested by scraping with a pipette tip. Lysed cells were combined with an equal volume of 64% ethanol and mixed thoroughly by pipetting. The ethanol-lysate mix was transferred to a column and spun at 12,000×G for 1 minute and flow through discarded. The membrane was washed by adding wash buffer 1 to the column and centrifuging at 12,000×G for 1 minute, before discarding the flow through and repeating this step twice with wash buffer 2. An additional spin with the empty cartridge was included to completely dry the membrane of ethanol. Finally, the total RNA was eluted in 2 sequential aliquots of 50 µl preheated elution buffer (nuclease-free water containing trace amounts of EDTA).

Analysis of RNA Quantity, Purity and Integrity

RNA concentration was quantified by measuring the absorbance at 260 nm, using a Nanodrop Lite spectrophotometer (Thermo Scientific). The purity of RNA was determined by analysing the A$_{260:280}$ ratio, where a value of between 1.8 and 2.1 was deemed to be free from protein contamination and acceptable for downstream applications. The integrity of the RNA was determined by running a sample on a denaturing formaldehyde agarose gel. A 1% agarose (Sigma Aldrich), 1×MOPS (Sigma Aldrich), 6.6% formaldehyde (Fisher Scientific) gel was made with the addition of 1×SYBR™ Safe DNA stain (Invitrogen) to visualize the nucleic acids. Prior to loading, equal volumes of formaldehyde loading dye (Ambion) was added to 1 µg RNA and samples were heated at 70° C. for 10 minutes before being immediately snap cooled on ice for 2-3 minutes. The gel was run at 90V for 1 hour 30 minutes and visualised under UV light, using the NuGenius gel doc system (Syngene). The 28S and 18S rRNA bands were scrutinized for sharp, intense bands at approximately 5 kb and 1.9 kb, respectively, where the 28S upper band was expected to be twice the intensity of the 18S lower band for intact RNA. Smearing below the 18S rRNA band was taken to indicate degraded RNA, whilst smearing and/or bands above the 28S rRNA was indicative of DNA contamination. Following analysis, RNA was used immediately for reverse transcription.

Reverse Transcription

Reverse transcription was carried out using ISCRIPT™ Advanced cDNA Synthesis Kit for RT-qPCR (Biorad). To 1 µg DNase-treated RNA, 4 µl of 5×ISCRIPT™ Advanced reaction mix and 1 µl ISCRIPT™ Advanced Reverse Transcriptase was added. Nuclease-free water was added to a final volume of 20 µl and the reaction was incubated at 46° C. for 20 minutes, before inactivation at 95° C. for 1 minute. Newly synthesised cDNA was diluted 10-fold in TE buffer (10 mM Tris pH 8, 1 mM EDTA), aliquoted and stored at −20° C. until use in qPCR experiments.

Qualitative Real-Time PCR Analysis

Reference genes were selected based on data from existing literature. The selected target genes were as set out in Table 3.

TABLE 3

Selected Target Genes for Qualitative Real-Time PCR Analysis

| Gene | Pathway | Expected outcome in response to FXR Activation |
|---|---|---|
| NR0B2 (SHP) | FXR Signalling, BA secretion | Upregulated |
| OSTα | BA transport across cell membranes | Upregulated |
| CYP7A1 | BA synthesis | Downregulated |
| TGFB1 | Fibrosis, tissue remodelling, monocyte signalling | Downregulated |
| GAPDH | Housekeeping | Stable |
| ACTB (BACTIN) | Housekeeping | Stable |

Optimisation of Primers for qPCR

KICQSTART® SYBR® Green Predesigned primers (chosen according to best rank) for the above target genes were purchased from Sigma Life Science. Nuclease-free water was added to the lyophilized primers for a stock concentration of 100 µM. Primers were diluted with nuclease-free water for a working concentration of 10 µM. To test the efficiency, reproducibility and dynamic range of the assay, a ten-fold serial dilution was made; consisting of 5 concentrations of cDNA generated (as outlined above) from Human Reference RNA (Agilent). Following qPCR of these samples, a standard curve was constructed by the threshold cycle (Ct) value (y-axis) versus log cDNA concentration (x-axis). The primer amplification efficiency (E) of one cycle in the exponential phase was determined by the equation $E = 10^{(-1/slope)} - 1$ (Pfaffl, 2001). The accuracy of these qPCR reactions was determined by the $R^2$ value of the standard curve, with values>0.98 being suitable. The specificity of each primer was determined by melt curve analysis, which was performed at the end of each run, where the production of one peak at one melting temperature indicated the amplification of just one product and, therefore, primers that were highly specific. Amplified products were confirmed by agarose gel electrophoresis (2% Agarose, 1×TAE, run at 100V for 30 minutes) to check amplicon sizes were as expected, and that only one product was seen.

Quantitative PCR

The ready-to-use reaction mastermix, ITAQ™ Universal SYBR® Green Supermix (Biorad) was used for all qPCR reactions. A typical reaction for each gene contained 5 µl 2×ITAQ™ Universal SYBR® Green Supermix, 500 nm forward and 500 nm reverse primers, approximately 15 ng cDNA and nuclease-free water to a final volume of 10 µl. Each target gene, reference gene and no template control were run in triplicate on an Optical MicroAmp 96 well plate (Applied Biosystems). Plates were sealed with an optical adhesive seal (Applied biosystems), briefly placed on a plate shaker to mix the components and centrifuged. Reactions were run using the Applied Biosystem Step One Plus real-time PCR system, using the following cycling conditions; an initial denaturation step at 95° C. for 15 minutes, 40 cycles of amplification, consisting of denaturation step at 94° C. for 15 seconds, combined annealing and extension step at 60° C. for 1 minute, with a single fluorescent measurement. Melting curve analysis was performed straight after each run by increasing the temperature from 60° C. to 95° C. in 0.3° C. increments, and measuring fluorescence dissociation.

Data Analysis

To quantify gene expression, the baseline-corrected $C_t$ value was determined automatically by the qPCR system software (Applied Biosystems). Relative changes in gene expression were determined by the Livak, or $\Delta\Delta C_t$, method whereby the $C_t$ values of target genes were normalised to $C_t$ value of the reference gene, for both the samples treated with vehicle/untreated samples (control) and the samples treated with compound (test samples). The $\Delta C_t$ values for the test samples were then normalised against the $\Delta C_t$ values of the control samples. And finally, the expression ratio was calculated using the equation $2^{-\Delta\Delta C_t}$. In total, there were 3 biological replicates and all data are represented as mean±SE. Treatments are compared by one way ANOVA followed by Tukey's and Dunnet's post hoc tests.

Results

Figure 2:
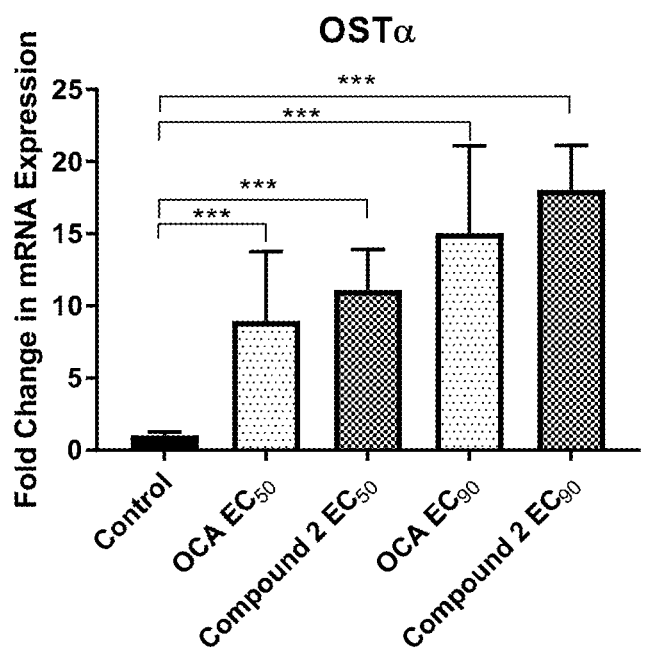
FIG. 2 shows the change in OSTα expression after 24 hours incubation of the human hepatoma cell line Huh7 with control, OCA (at $EC_{50}$ and $EC_{90}$) and Compound 2 (at $EC_{50}$ and $EC_{90}$).

Direct target genes, nr0b2 (SHP) and slc51a (OSTα), which are involved in bile acid homeostasis and known to be positively regulated by FXR (Goodwin et al., 2000; Landrier et al., 2006), display significant increases upon Huh7 treatment with Compound 2. SHP expression levels are increased following Compound 2 treatment by between 1.5 ($EC_{50}$ concentration) and 2.5 times ($EC_{50}$ concentration) (FIG. 1). Ostα mRNA was also considerably upregulated, displaying 11-fold and 18-fold increases in expression, upon treatment with Compound 2, at its $EC_{50}$ and $EC_{90}$ concentrations respectively (FIG. 2).

Figure 3:
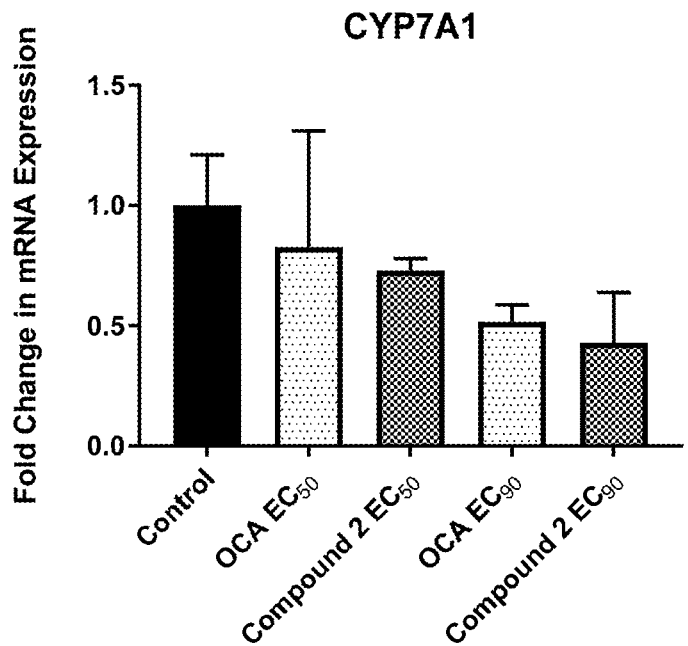
FIG. 3 shows the change in CYP7A1 expression after 24 hours incubation of the human hepatocellular carcinoma cell line HepG2 with control, OCA (at $EC_{50}$ and $EC_{90}$) and Compound 2 (at $EC_{50}$ and $EC_{90}$).

FXR activation leads to the suppression of CYP7A1 via both a SHP-mediated, and FGF19-mediated pathway. CYP7A1 is downregulated with increasing concentrations of Compound 2 (FIG. 3).

Figure 4:
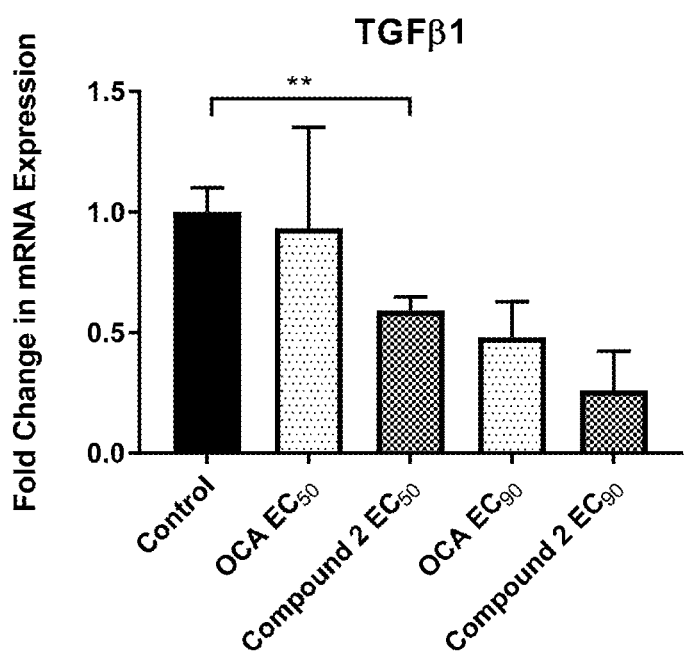
FIG. 4 shows the change in TGFβ1 expression after 24 hours incubation of the human hepatocellular carcinoma cell line HepG2 with control, OCA (at $EC_{50}$ and $EC_{90}$) and Compound 2 (at $EC_{50}$ and $EC_{90}$).

HepG2 cells display a significant downregulation in TGFβ1 expression levels in response to treatment with Compound 2 at its $EC_{50}$ concentration (FIG. 4).

Figure 5:
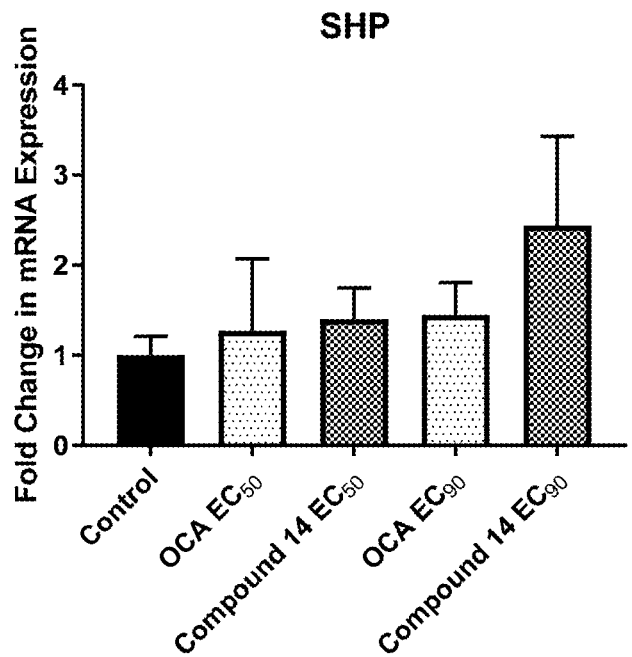
FIG. 5 shows the change in SHP expression after 24 hours incubation of the human hepatoma cell line Huh7 with control, OCA (at $EC_{50}$ and $EC_{90}$) and Compound 14 (at $EC_{50}$ and $EC_{90}$).
Figure 6:
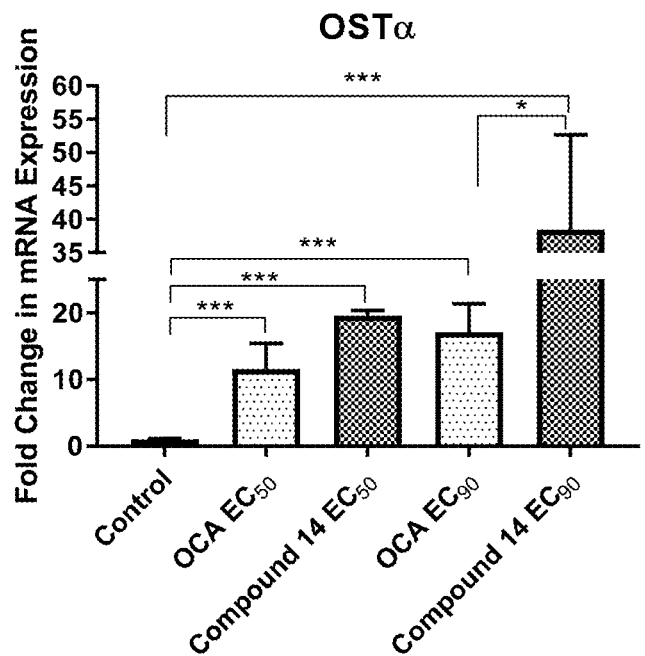
FIG. 6 shows the change in OSTα expression after 24 hours incubation of the human hepatoma cell line Huh7 with control, OCA (at $EC_{50}$ and $EC_{90}$) and Compound 14 (at $EC_{50}$ and $EC_{90}$).

SHP displayed a modest increase whereby treatment with Compound 14 at its $EC_{90}$ concentration more than doubled expression levels (FIG. 5). Compound 14 induced highly significant increases in the FXR-target Ostα, with treated cells achieving 20- to 40-times higher mRNA expression levels than vehicle-treated cells (FIG. 6).

Figure 7:
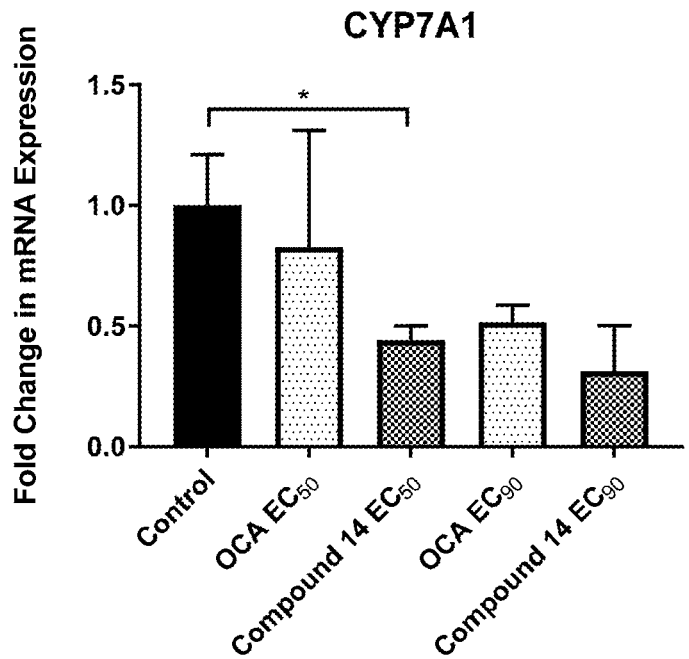
FIG. 7 shows the change in CYP7A1 expression after 24 hours incubation of the human hepatocellular carcinoma cell line HepG2 with control, OCA (at $EC_{50}$ and $EC_{90}$) and Compound 14 (at $EC_{50}$ and $EC_{90}$).

At the $EC_{50}$ concentration, Compound 14 significantly decreased CYP7A1 expression, reducing it to more than half the levels seen for the vehicle control cells (FIG. 7).

Figure 8:
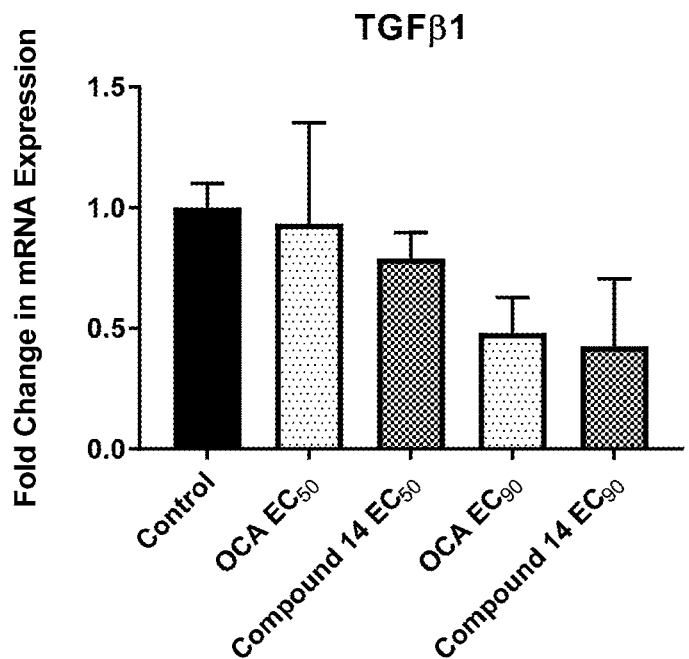
FIG. 8 shows the change in TGFβ1 expression after 24 hours incubation of the human hepatocellular carcinoma cell line HepG2 with control, OCA (at $EC_{50}$ and $EC_{90}$) and Compound 14 (at $EC_{50}$ and $EC_{90}$).

Similarly to Compound 2, Compound 14 induces a decline in TGFβ1 expression with increasing compound concentrations (FIG. 8).

The inventors wish to thank Dannielle Kydd-Sinclair of the University of Reading, who provided much of the background section as well as the methodology and data for the biological examples as mentioned above, and David Evans, Simon Holland and Lawrence Tam of the University of Southampton, who carried out the synthesis of several of the example compounds.

REFERENCES

Alemi, F. et al. (2013) 'The TGR5 receptor mediates bile acid—induced itch and analgesia', *The Journal of Clinical Investigation*, 123(4), pp. 1513-1530. doi: 10.1172/JCI64551.mation.

Ananthanarayanan, M. et al. (2004) 'Ligand-dependent activation of the farnesoid X-receptor directs arginine methylation of histone H3 by CARM1', *Journal of Biological Chemistry*, 279(52), pp. 54348-54357. doi: 10.1074/jbc.M410021200.

Bellentani, S. (2017) 'The epidemiology of non-alcoholic fatty liver disease', 37 (October 2016), pp. 81-84. doi: 10.1111/liv.13299.

Cave, M. C. et al. (2016) 'Biochimica et Biophysica Acta Nuclear receptors and nonalcoholic fatty liver disease 1', *BBA—Gene Regulatory Mechanisms*. Elsevier B.V., 1859 (9), pp. 1083-1099. doi: 10.1016/j.bbagrm.2016.03.002.

Using Combinatorial Peptide Libraries: Discovery of Peptide Antagonists of Estrogen Receptors α and β. Molecular and Cellular Biology, 19(12), 8226-8239, at the Hypertext Transfer Protocol Secure (https)doi.org/10.1128/mcb.19.12.8226

Chiang, J. Y. L. (2013) 'Bile Acid Metabolism and Signalling', *Comprehensive Physiology*, 3(3), pp. 1191-1212. doi: 10.1002/cphy.c120023.Bile.

Cipriani, S. et al. (2010) 'FXR activation reverses insulin resistance and lipid abnormalities and protects against liver steatosis in Zucker (fa/fa) obese rats', *Journal of Lipid Research*, 51, pp. 771-784. doi: 10.1194/jlr.M001602.

Clerici et al, *Toxicology and Applied Pharmacology*, 214, 199-208 (2006)

Copple, B. L. and Li, T. (2016) 'Pharmacology of bile acid receptors: Evolution of bile acids from simple detergents to complex signaling molecules', *Pharmacological Research*. Elsevier Ltd, 104, pp. 9-21. doi: 10.1016/j.phrs.2015.12.007.

Cushman et al, *J. Med. Chem*. (1995), Cosalane analogs with enhanced potencies as inhibitors of HIV-1 protease and integrase', 38(3), 443-452

Cusi, *Gastroenterology* (2012), 'Role of obesity and lipotoxicity in the development of nonalcoholic steatohepatitis: pathophysiology and clinical implications', 142(4), 711-725

Deuschle, U. et al. (2012) 'FXR Controls the Tumor Suppressor NDRG2 and FXR Agonists Reduce Liver Tumor Growth and Metastasis in an Orthotopic Mouse Xenograft Model', *PLoS ONE*, 7(10). doi: 10.1371/journal.pone.0043044.

Dyson, J. K., Anstee, Q. M. and McPherson, S. (2014) 'Non-alcoholic fatty liver disease: a practical approach to diagnosis and staging.', *Frontline gastroenterology*, 5(3), pp. 211-218. doi: 10.1136/flgastro-2013-100403.

Evans, R. M. and Mangelsdorf, D. J. (2014) 'Nuclear Receptors, RXR and the Big Bang', *Cell*, 157(1), pp. 255-266. doi: 10.1016/j.cell.2014.03.012.Nuclear.

Goodwin, B., Jones, S. A., Price, R. R., Watson, M. A., McKee, D. D., Moore, L. B., . . . Kliewer, S.A. (2000). A regulatory cascade of the nuclear receptors FXR, SHP-1, and LRH-1 represses bile acid biosynthesis. Molecular Cell, 6(3), 517-526, at the Hypertext Transfer Protocol Secure (https) doi.org/10.1016/S1097-2765(00)00051-4.

Haas, J. T., Francque, S. and Staels, B. (2016) 'Pathophysiology and Mechanisms of Nonalcoholic Fatty Liver Disease', *Annual Review of Physiology*, 78, pp. 181-205. doi: 10.1146/annurev-physiol-021115-105331.

Henao-mejia, J. et al. (2012) 'Inflammasome-mediated dysbiosis regulates progression of NAFLD and obesity.', *Nature*, 482(7384), pp. 179-185. doi: 10.1038/nature10809.Inflammasome-mediated.

Honorio et al, 'Hologram QSAR Studies on Farnesoid X Receptor Activators', *Letters in Drug Design & Discovery*, (2006), 3(4), 261-271

Huber, R. et al. (2002) 'Generation of multiple farnesoid-X-receptor isoforms through the use of alternative promoters', *Gene*, 290(1-2), pp. 35-43.

Inagaki, T. et al. (2006) 'Regulation of antibacterial defense in the small intestine by the nuclear bile acid receptor', *Proc Natl Acad Sci USA*, 103(10), pp. 3920-3925. doi: 10.1073/pnas.0509592103.

Jiang, Y. et al. (2013) 'Farnesoid X receptor inhibits gankyrin in mouse livers and prevents development of liver cancer.', *Hepatology (Baltimore, Md.)*, 57(3), pp. 1098-106. doi: 10.1002/hep.26146.

Kast, H. R. et al. (2001) 'Farnesoid X-activated receptor induces apolipoprotein C-II transcription: a molecular mechanism linking plasma triglyceride levels to bile acids.', *Molecular endocrinology (Baltimore, Md.)*, 15(10), pp. 1720-1728. doi: 10.1210/me.15.10.1720.

Kong, B. et al. (2009) 'Farnesoid X Receptor Deficiency Induces Nonalcoholic Steatohepatitis in Low-Density Lipoprotein Receptor-Knockout Mice Fed a High-Fat Diet', *Journal of Pharmacology and Experimental Therapeutics*, 328(1), pp. 116-122. doi: 10.1124/jpet.108.144600.

Landrier, J-F et al (2006) 'The nuclear receptor for bile acids, FXR, transactivates human organic solute transporter-α and -β genes', *Am. J. Physiol. Gastrointest. Liver Physiol.*, 290, pp G476-G485.

Ma, K. et al. (2006) 'Farnesoid X receptor is essential for normal glucose homeostasis', *Journal of Clinical Investigation*, 116(4), p. 1102. doi: 10.1172/JC125604.1102.

Ma, Y. et al. (2013) 'Synthetic FXR Agonist GW4064 Prevents Diet-Induced Hepatic Steatosis and Insulin Resistance', *Pharmaceutical Research*, 30, pp. 1447-1457. doi: 10.1007/s11095-013-0986-7.

Macchiarulo et al, *Journal of Chemical Information and Modeling*, 48, 1792-1801 (2008)

Maloney, P. R. et al. (2000) 'Identification of a chemical tool for the orphan nuclear receptor FXR', *Journal of Medicinal Chemistry*, 43(16), pp. 2971-2974. doi: 10.1021/jm0002127.

Min, H. et al. (2013) 'Increased hepatic synthesis and dysregulation of cholesterol metabolism is associated with the severity of nonalcoholic fatty liver disease', *Cell Metabolism*, 15(5), pp. 665-674. doi: 10.1016/j.cmet.2012.04.004.

Mouzaki, M. et al. (2013) 'Intestinal Microbiota in Patients With Nonalcoholic Fatty Liver Disease', *Hepatology*, 1, pp. 120-127. doi: 10.1002/hep.26319.

Mudaliar, S. et al. (2013) 'Efficacy and Safety of the Farnesoid X Receptor Agonist Obeticholic Acid in Patients With Type 2 Diabetes and Nonalcoholic Fatty Liver Disease', *Gastroenterology*. Elsevier, Inc, 145(3), p. 574-582.e1. doi: 10.1053/j.gastro.2013.05.042.

Neuschwander-Tetri, B. A. (2012) 'Farnesoid X receptor agonists: What they are and how they might be used in treating liver disease', *Current Gastroenterology Reports*, 14(1), pp. 55-62. doi: 10.1007/s11894-011-0232-6.

Neuschwander-Tetri, B. A. et al. (2015) 'Farnesoid X nuclear receptor ligand obeticholic acid for non-cirrhotic, non-alcoholic steatohepatitis (FLINT): a multicentre, randomised, placebo-controlled trial Prof.', *Lancet*, 385 (9972), pp. 956-965. doi: 10.1016/S0140-6736(14) 61933-4.Farnesoid.

Pacana, T. and Sanyal, A. J. (2015) 'Recent advances in understanding/management of non-alcoholic steatohepatitis', *F1000 Prime Reports*, 7(28), pp. 1-8. doi: 10.12703/P7-28.

Paulekuhn et al., (2007) 'Trends in Active Pharmaceutical Ingredient Salt Selection based on Analysis of the Orange Book Database', *J. Med. Chem.* 50, 6665-6672

Pfaffl, M. W. (2001). A new mathematical model for relative quantification in real-time RT—PCR. *Nucleic Acids Research*, 29(9), 16-21.

Roda et al, *Gastroenterology* (1995) 'Metabolism, pharmacokinetics, and activity of a new 6-fluoro analogue of ursodeoxycholic acid in rats and hamsters', 108(4), 1204-1214.

Sato et al, 'Novel Potent and Selective Bile Acid Derivatives as TGR5 Agonists: Biological Screening, Structure-Activity Relationships, and Molecular Modeling Studies', *J. Med. Chem.* (2008), 51(15), 4831-4849.

Sievanen E. et al, '$^{1}$H, $^{13}$C, $^{19}$F NMR, and ESI mass spectral characterization of two geminal difluorosteroids', *Magnetic Resonance in Chemistry*, (2008), 46(4), 392-397.

Uekawa et al (2004) 'Short-step Synthesis of Chenodiol from Stigmasterol', *Biosci. Biotechnol. Biochem.*, 68, 1332-1337

Vaquero, J. et al. (2013) 'Differential activation of the human farnesoid X receptor depends on the pattern of expressed isoforms and the bile acid pool composition', *Biochemical Pharmacology*, 86(7), pp. 926-939. doi: 10.1016/j.bcp.2013.07.022.

Wang, Y. et al. (2008) 'Farnesoid X receptor antagonizes NF-kB in hepatic inflammatory response', *Hepatology*, 48(5), pp. 1632-1643. doi: 10.1002/hep.22519.Farnesoid.

Watanabe, M., Houten, S. M., Wang, L., Moschetta, A., Mangelsdorf, D. J., Heyman, R. A., . . . Auwerx, J. (2004). Bile acids lower triglyceride levels via a pathway involving FXR, SHP, and SREBP-1c. Journal of Clinical Investigation, 113(10), 1408-1418, at the Hypertext Transfer Protocol Secure (https)doi.org/10.1172/JCI200421025.

Watanabe, M. et al. (2011) 'Lowering bile acid pool size with a synthetic farnesoid X receptor (FXR) agonist induces obesity and diabetes through reduced energy expenditure', *Journal of Biological Chemistry*, 286(30), pp. 26913-26920. doi: 10.1074/jbc.M111.248203.

Wuts, P G M and Greene, T W (2006) "Greene's Protective Groups in Organic Synthesis", 4$^{th}$ Edition, John Wiley & Sons, Inc., Hoboken, N.J., USA, Xiao, H. et al (2017) 'Synthesis and biological evaluation of a series of bile acid derivatives as FXR agonists for treatment of NASH', Med. Chem. Lett. 8, 1246-1251.

Yang, Z., Shen, W. and Sun, H. (2010) 'Effects of nuclear receptor FXR on the regulation of liver lipid metabolism in patients with non-alcoholic fatty liver disease', *Hepatology International*, 4(4), pp. 741-748. doi: 10.1007/s12072-010-9202-6.

Zhang, Y. et al. (2004) 'Peroxisome proliferator-activated regulates triglyceride metabolism by activation of the nuclear receptor FXR', *Genes & Development*, 18, pp. 157-169. doi: 10.1101/gad.1138104.

Zhang, Y. et al. (2006) 'Activation of the nuclear receptor FXR improves hyperglycemia and hyperlipidemia in diabetic mice.', *Proceedings of the National Academy of Sciences of the United States of America*, 103(4), pp. 1006-1011. doi: 10.1073/pnas.0506982103.

Zhang, Y., Kast-woelbern, H. R. and Edwards, P. A. (2003) 'Natural Structural Variants of the Nuclear Receptor Farnesoid X Receptor Affect Transcriptional Activation', *Journal of Biological Chemistry*, 278(1), pp. 104-110. doi: 10.1074/jbc.M209505200.

The invention claimed is:
1. A compound of general formula (I):
wherein

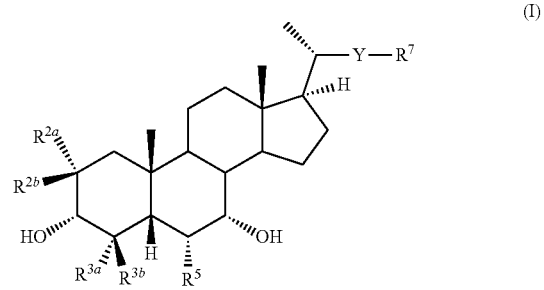

each of $R^{2a}$, $R^{2b}$, $R^{3a}$ and $R^{3b}$ is independently H or F, and provided that at least one of $R^{2b}$ and $R^{3b}$ is F;

$R^5$ is selected from $CR^{6a}R^{6b}R^8$, $OR^8$, $SR^8$ and $NR^{6a}R^8$;
each of $R^{6a}$, $R^{6b}$ and $R^8$ is independently H or methyl
Y is selected from a bond, and a $C_{1-4}$ alkylene, or a $C_{2-4}$ alkenylene linker group, any of which is optionally substituted with one or more $R^{10}$;
wherein each $R^{10}$ is independently halo or OH;
$R^7$ is selected from $C(O)NR^{17}S(O)_2R^{15}$, $NR^{17}C(O)NR^{18}S(O)_2R^{15}$, $NR^{17}C(S)NR^{18}S(O)_2R^{15}$ and $NR^{17}C(NR^{20})NR^{18}S(O)_2R^{15}$;

$R^{15}$ is selected from a 5- to 10-membered aryl ring and a 5- to 10-membered heteroaryl ring,
any of which is optionally substituted with one or more substituents selected from C1-6 alkyl,
$C_{1-6}$ haloalkyl, halo, $O(C_{1-5}$ alkyl), and $O(C_{1-6}$ haloalkyl);
each $R^{17}$ and $R^{18}$ is independently selected from H and methyl;
$R^{20}$ is selected from H, methyl and CN;
or a salt thereof.

2. The compound according to claim 1, wherein $R^{3b}$ is F, and each of $R^{3a}$, $R^{2a}$ and $R^{2b}$ is H.

3. The compound according to claim 1, wherein $R^{2b}$ is F, and each of $R^{2a}$, $R^{3a}$ and $R^{3b}$ is H.

4. The compound according to claim 1, wherein: $R^{3b}$ is F, $R^{3a}$ is H, one of $R^{2a}$ and $R^{2b}$ is F, and the other of $R^{2a}$ and $R^{2b}$ is H; or wherein $R^{3a}$ and $R^{3b}$ are both F, and $R^{2a}$ and $R^{2b}$ are both H.

5. The compound according to claim 1, wherein $R^5$ is ethyl.

6. The compound according to claim 1, wherein Y is selected from a bond, and a $C_{1-3}$ alkylene linker group, which is optionally substituted with one or more OH groups.

7. The compound according to claim 1, wherein $R^7$ is $C(O)NR^{17}S(O)_2R^{15}$, or $NR^{17}C(O)NR^{18}S(O)_2R^{15}$.

8. The compound according to claim 7, wherein, independently or in any combination: each of $R^{17}$ and $R^{18}$ is H; and/or $R^{15}$ is selected from phenyl and a 5- or 6-membered heteroaryl, any of which may be unsubstituted or substituted with one or more substituents selected from $C_{1-6}$ alkyl; $C_{1-6}$ haloalkyl; halo, $O(C_{1-6}$ alkyl), and $O(C_{1-6}$ haloalkyl).

9. The compound according to claim 8, wherein $R^{15}$ is phenyl, which is unsubstituted or is substituted with a single substituent selected from fluoro, $C_{1-4}$ alkyl, $C_{1-4}$ fluoroalkyl, $O(C_{1-4}$ alkyl) and $O(C_{1-4}$ fluoroalkyl).

10. The compound according to claim 1, wherein the compound is selected from:
N,N'-(3α,7α-dihydroxyl-4β-fluoro-6α-ethyl-24-nor-5β-cholan-23-yl)-p-toluene sulfonyl urea (Compound 1);
N,N'-(3α,7α-dihydroxyl-4β-fluoro-6α-ethyl-24-nor-5β-cholan-23-yl)-benzene sulfonyl urea (Compound 2);
N,N'-(3α,7α-dihydroxyl-4β-fluoro-6α-ethyl-24-nor-5β-cholan-23-yl)-4-(tert-butyl) benzene sulfonyl urea (Compound 3);
N,N'-(3α,7α-dihydroxyl-4β-fluoro-6α-ethyl-24-nor-5β-cholan-23-yl)-m-toluene sulfonyl urea (Compound 4);
N,N'-(3α,7α-dihydroxyl-4β-fluoro-6α-ethyl-24-nor-5β-cholan-23-yl)-o-toluene sulfonyl urea (Compound 5);
N,N'-(3α,7α-dihydroxyl-4β-fluoro-6α-ethyl-24-nor-5β-cholan-23-yl)-p-fluorobenzene sulfonyl urea (Compound 6);
N,N'-(3α,7α-dihydroxyl-4β-fluoro-6α-ethyl-24-nor-5β-cholan-23-yl)-m-fluorobenzene sulfonyl urea (Compound 7);
N,N'-(3α,7α-dihydroxyl-4β-fluoro-6α-ethyl-24-nor-5β-cholan-23-yl)-o-fluorobenzene sulfonyl urea (Compound 8);
N,N'-(3α,7α-dihydroxyl-4β-fluoro-6α-ethyl-24-nor-5β-cholan-23-yl)-p-(trifluoromethyl)benzene sulfonyl urea (Compound 9);
N,N'-(3α,7α-dihydroxyl-4β-fluoro-6α-ethyl-24-nor-5β-cholan-23-yl)-m-(trifluoromethyl)benzene sulfonyl urea (Compound 10);
N,N'-(3α,7α-dihydroxyl-4β-fluoro-6α-ethyl-24-nor-5β-cholan-23-yl)-o-(trifluoromethyl)benzene sulfonyl urea (Compound 11);
N,N'-(3α,7α-dihydroxyl-4β-fluoro-6α-ethyl-24-nor-5β-cholan-23-yl)-4-(trifluoromethoxy)benzene sulfonyl urea (Compound 12);
N,N'-(3α,7α-dihydroxyl-4β-fluoro-6α-ethyl-24-nor-5β-cholan-23-yl)-p-methoxybenzene sulfonyl urea (Compound 13);
N-(3α,7α-dihydroxyl-4β-fluoro-6α-ethyl-5β-cholan-24-oyl)-p-trifluoromethoxy benzene sulfonamide (Compound 14);
N-(3α,7α-dihydroxyl-4β-fluoro-6α-ethyl-5β-cholan-24-oyl)-p-fluorobenzene sulfonamide (Compound 15);
N-(3α,7α-dihydroxyl-4β-fluoro-6α-ethyl-5β-cholan-24-oyl)-3-fluorophenyl sulfonamide (Compound 16);
N-(3α,7α-dihydroxyl-4β-fluoro-6α-ethyl-5β-cholan-24-oyl)-2-fluorophenyl sulfonamide (Compound 17);
N-(3α,7α-dihydroxyl-4β-fluoro-6α-ethyl-5β-cholan-24-oyl)-4-trifluoromethylphenyl sulfonamide (Compound 18);
N-(3α,7α-dihydroxyl-4β-fluoro-6α-ethyl-5β-cholan-24-oyl)-3-trifluoromethylphenyl sulfonamide (Compound 19);
N-(3α,7α-dihydroxyl-4β-fluoro-6α-ethyl-5β-cholan-24-oyl)-2-trifluoromethylphenyl sulfonamide (Compound 20);
N,N'-(3α,7α-dihydroxyl-4,4-difluoro-6α-ethyl-24-nor-5β-cholan-23-yl)-benzene sulfonyl urea (Compound 21)
N-(3α,7α-dihydroxyl-4,4-difluoro-6α-ethyl-5β-cholan-24-oyl)-benzene sulfonamide (Compound 22); and salts thereof.

11. A method of treating a metabolic syndrome, the method comprising administering an effective amount of the compound according to claim 1 to a patient.

12. A method for the treatment of nonalcoholic steatohepatitis (NASH); primary biliary cirrhosis; primary sclerosing cholangitis; biliary atresia; cholestatic liver disease; hepatitis C infection; alcoholic liver disease; fibrosis; or liver damage arising from fibrosis, the method comprising administering to a patient in need of such treatment an effective amount of a compound according to claim 1.

13. The method according to claim 12 wherein fibrosis is selected from fibrosis of the liver, kidneys and intestines.

14. The method according to claim 13, wherein the liver fibrosis is associated with NASH, alcoholic liver disease or non-alcoholic fatty liver disease, or is associated with an infection, selected from hepatitis B and hepatitis C, or a parasitic liver disease, or is caused by damage induced by a congenital disorder selected from Wilson's disease, Gaucher's disease, glycogen storage disorders, haemochromatosis, Zellweger syndrome, and congenital hepatic fibrosis, or is induced by a drug selected from chlorpromazine, tolbutamide, methotrexate, isoniazid arid methyldopa; and/or fibrosis of the kidneys is associated with a disease selected from diabetic nephropathy, hypertensive nephrosclerosis, glomerulonephritis, interstitial nephritis, glomerulopathy associated with transplant and polycystic kidney disease; and/or intestinal fibrosis is associated with a bowel disorder.

15. A pharmaceutical composition comprising a compound according to claim 1, and a pharmaceutically acceptable excipient or carrier.

16. The pharmaceutical composition according to claim 15, further comprising one or more additional active agents suitable for the treatment of a metabolic syndrome, wherein the metabolic syndrome is selected from nonalcoholic steatohepatitis (NASH); primary biliary cirrhosis; primary sclerosing cholangitis; biliary atresia; cholestatic liver disease; hepatitis C infection; alcoholic liver disease; fibrosis; and liver damage arising from fibrosis.

17. A process for the preparation of a compound according to claim 1, the process comprising:
A. for a compound of general formula (I) in which $R^7$ is $NHC(O)N(R^{18})S(O)_2R^{15}$: reacting a compound of general formula (III):

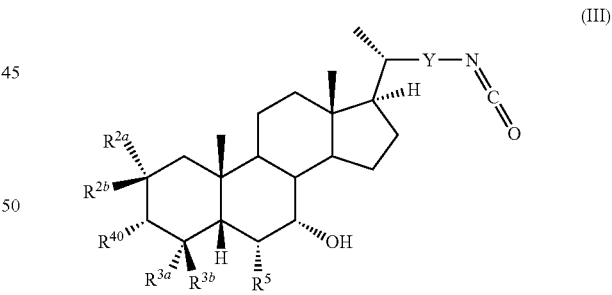

(III)

wherein Y, $R^{2a}$, $R^{2b}$, $R^{3a}$, $R^{3b}$ and $R^5$ are as defined in claim 1 and $R^{40}$ is a protected OH group;
with a sulfonamide of general formula (IV):

(IV)

wherein $R^{15}$ and $R^{18}$ are as defined in claim 1 in the presence of a catalyst;
to form a compound of general formula (II):

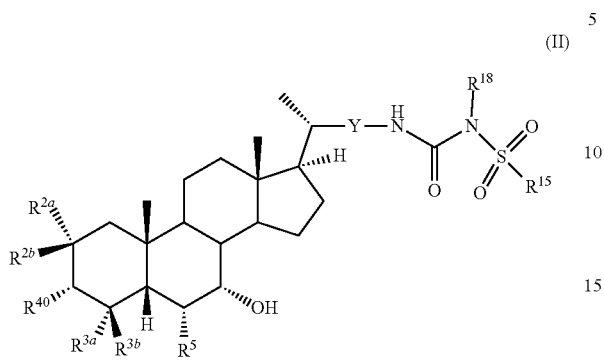
(II)

wherein Y, $R^{2a}$, $R^{2b}$, $R^{3a}$, $R^{3b}$ and $R^5$ are as defined in claim 1 and $R^{40}$ is a protected OH group; and
deprotecting the compound of general formula (II); or
B. for a compound of general formula (I) in which $R^7$ is $NHC(O)N(R^{18})S(O)_2R^{15}$: reacting a compound of general formula (XIII):

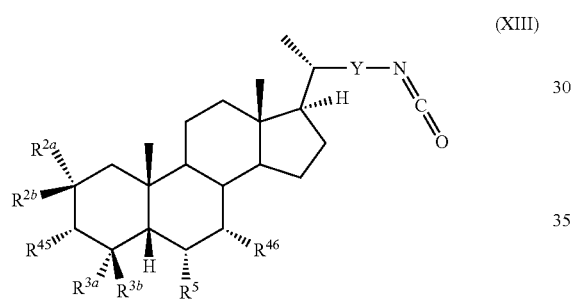
(XIII)

wherein Y, $R^{2a}$, $R^{2b}$, $R^{3a}$, $R^{3b}$ and $R^5$ are as defined in claim 1 and each of $R^{45}$ and $R^{46}$ is independently a protected OH group;
with a sulfonamide of general formula (IV) as defined above in the presence of a catalyst to form a compound of general formula (XII):

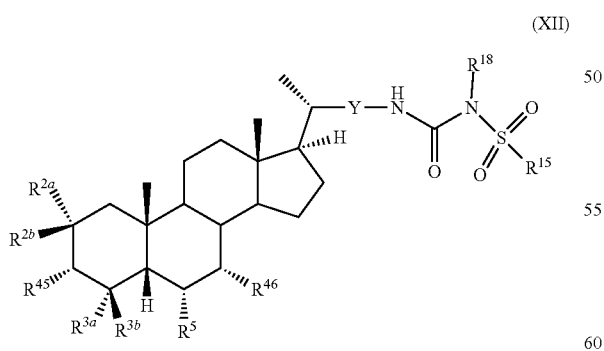
(XII)

wherein Y, $R^{2a}$, $R^{2b}$, $R^{3a}$, $R^{3b}$ and $R^5$ are as defined in claim 1 and each of $R^{45}$ and $R^{46}$ is independently a protected OH group; and
deprotecting the compound of general formula (XII); or
C. for a compound of general formula (I) in which $R^7$ is $C(O)N(R^{17})S(O)_2R^{15}$: reacting a compound of general formula (XIII):

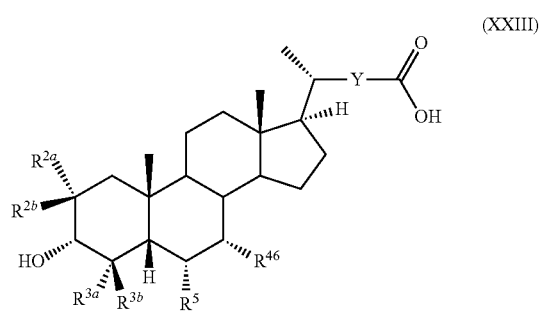
(XXIII)

wherein Y, $R^{2a}$, $R^{2b}$, $R^{3a}$, $R^{3b}$ and $R^5$ are as defined in claim 1 and $R^{46}$ is a protected OH group;
with a sulfonamide of general formula (XXIV):

(XXIV)

wherein $R^{15}$ and $R^{17}$ are as defined in claim 1;
in the presence of a coupling agent and a base;
to give a compound of general formula (XXII);

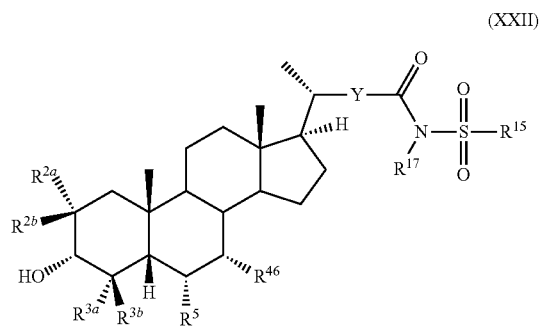
(XXII)

wherein Y, $R^{2a}$, $R^{2b}$, $R^{3a}$, $R^{3b}$, $R^5$, $R^{15}$ and $R^{17}$ are as defined in claim 1 and $R^{46}$ is as defined for general formula (XII); and
deprotecting the compound of general formula (XXII).

* * * * *